United States Patent
Fujii et al.

(10) Patent No.: US 7,176,475 B2
(45) Date of Patent: Feb. 13, 2007

(54) ADJUSTING APPARATUS, PRODUCTION PROCESSING SYSTEM, AND METHOD OF CONTROLLING ADJUSTING APPARATUS

(75) Inventors: Toru Fujii, Kyoto (JP); Manabu Tsuda, Kyoto (JP); Hiroshi Kumamoto, Kyoto (JP)

(73) Assignee: Omron Corporation, Kyoto (JP)

( * ) Notice: Subject to any disclaimer, the term of this patent is extended or adjusted under 35 U.S.C. 154(b) by 0 days.

(21) Appl. No.: 11/274,954

(22) Filed: Nov. 16, 2005

(65) Prior Publication Data

US 2006/0102858 A1    May 18, 2006

(30) Foreign Application Priority Data

Nov. 16, 2004 (JP) ............................. 2004-331901
Jul. 27, 2005 (JP) ............................. 2005-217704

(51) Int. Cl.
*G01N 21/88* (2006.01)
*G01N 21/00* (2006.01)

(52) U.S. Cl. ............................. 250/559.45; 356/237.1

(58) Field of Classification Search ........... 250/559.45; 356/237.1
See application file for complete search history.

(56) References Cited

U.S. PATENT DOCUMENTS

2003/0138978 A1*  7/2003  Tanaka et al. ............... 438/5

FOREIGN PATENT DOCUMENTS

| JP | 2-74852 A | 3/1990 |
| JP | 5-47619 A | 2/1993 |
| JP | 10-132536 A | 5/1998 |
| JP | 10-132914 A | 5/1998 |
| JP | 2005-59070 A | 3/2005 |

* cited by examiner

*Primary Examiner*—Georgia Epps
*Assistant Examiner*—Brian Livedalen
(74) *Attorney, Agent, or Firm*—Foley & Lardner LLP

(57) ABSTRACT

An adjusting apparatus includes a judging unit that receives a characteristic value of an article processed by one of processing machines from one of measuring machines and, on the basis of the characteristic value, judges whether or not the processed article meets regular quality, and an abnormality estimating unit that, when the processed article does not meet regular quality, specifies an device to be adjusted on the basis of whether a characteristic value out of the regular range appears for every two cycles or three cycles.

20 Claims, 29 Drawing Sheets

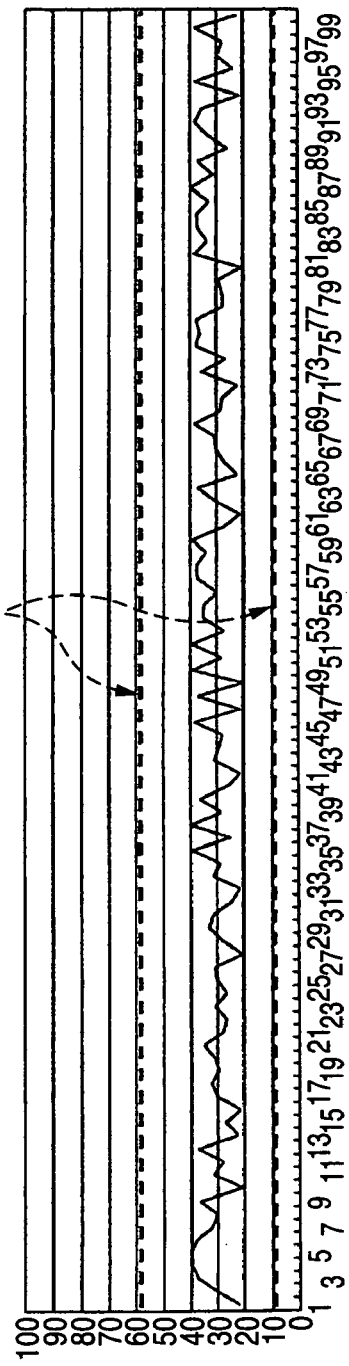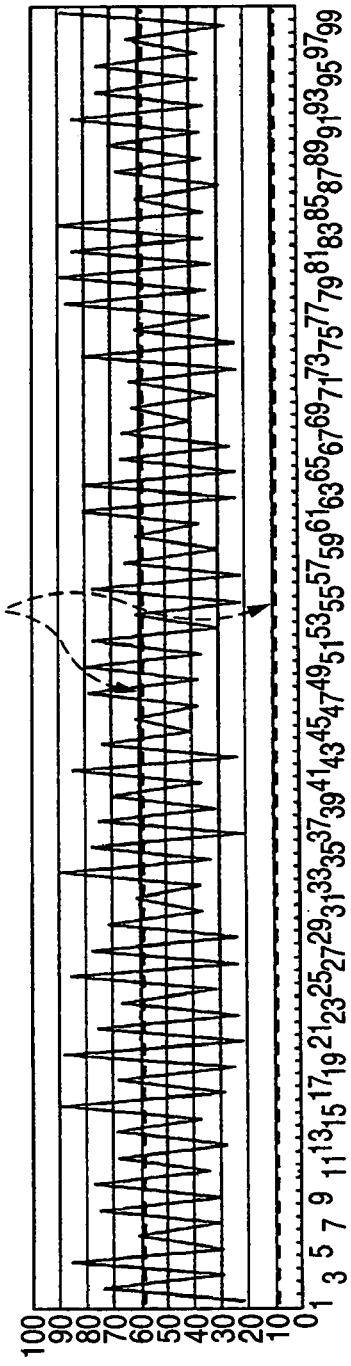
FIG. 3A
FIG. 3B

FIG. 4

| | CHARACTERISTIC VALUE IS WITHIN REGULAR RANGE | CHARACTERISTIC VALUE IS OUT OF REGULAR RANGE FOR EVERY ONE | CHARACTERISTIC VALUE IS OUT OF REGULAR RANGE FOR EVERY TWO | CHARACTERISTIC VALUE IS OUT OF REGULAR RANGE FOR EVERY ELEVEN |
|---|---|---|---|---|
| EQUATION (2) | 5998 | 214833 | 160733 | 37930 |
| EQUATION (3) | 6280 | 14523 | 165419 | 38274 |
| EQUATION (4) | 5675 | 215963 | 8467 | 37789 |

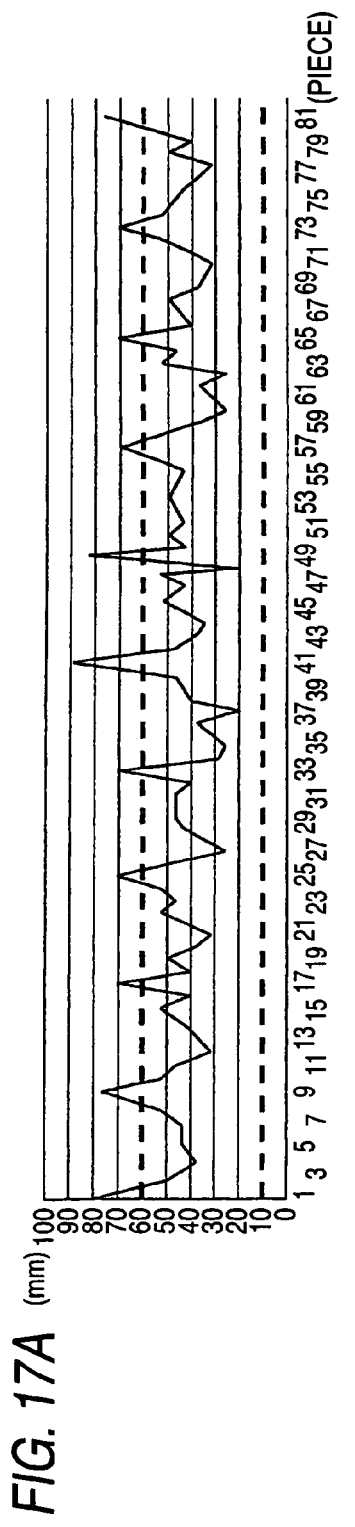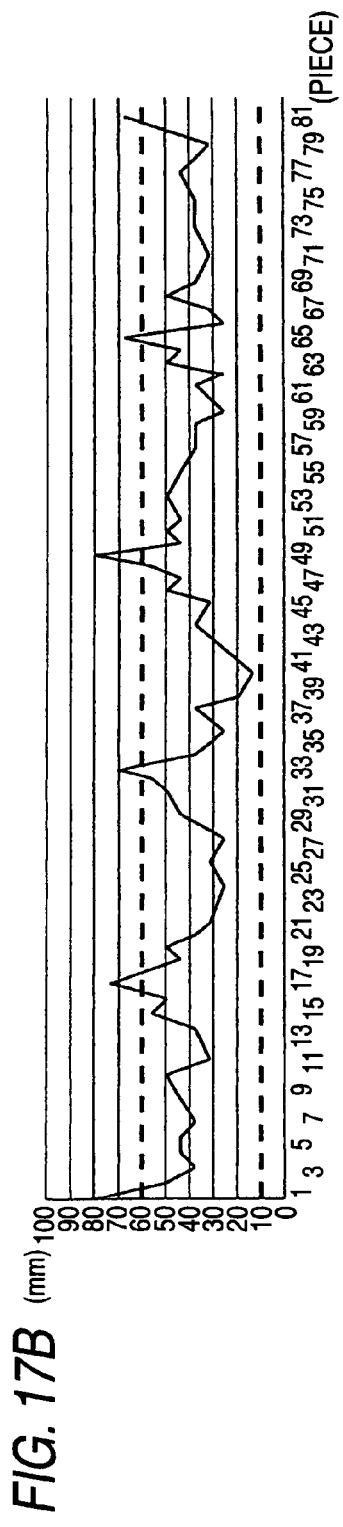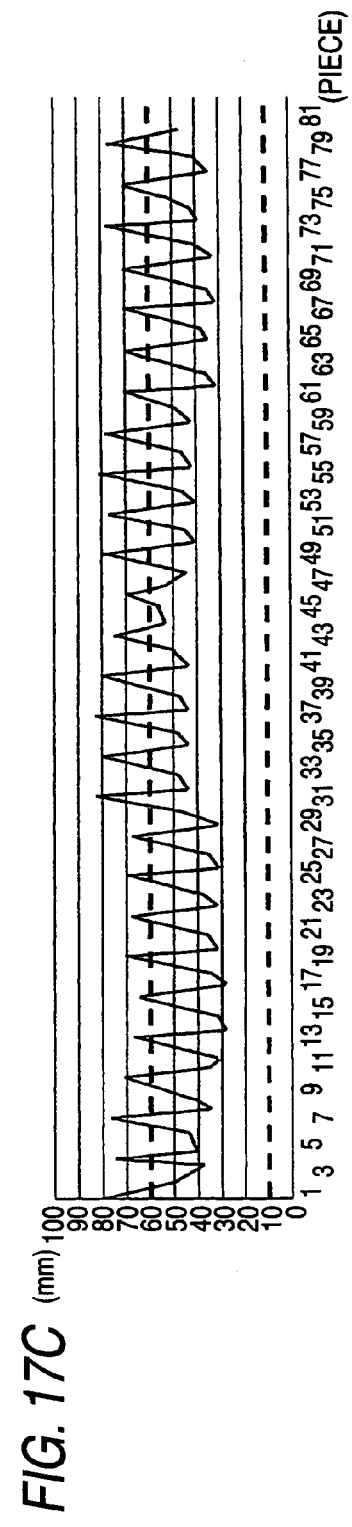

ADJUSTING APPARATUS, PRODUCTION PROCESSING SYSTEM, AND METHOD OF CONTROLLING ADJUSTING APPARATUS

The present application claims foreign priority based on Japanese Patent Application No. 2004-331901, riled Nov. 16, 2005 and Japanese Patent Application No. 2005-217704, filed Jul. 27, 2005, the contents of which are incorporated herein by reference.

BACKGROUND OF THE INVENTION

1. Technical Field

The present invention relates to an adjusting apparatus which receives characteristic values indicating quality of articles processed by one of m production processing devices from one of n measuring devices, and specifies and adjusts the production processing device or measuring device as a device to be adjusted.

2. Related Art

In the related art, in order to enhance productivity of articles, a production method is used in which a plurality of processing machines having the same function or a plurality of processing boards having the same function are provided for each production line, and articles are produced with the operation from the initial process to the last process. In such a production method, generally, a plurality of production lines are provided, and the articles are processed in parallel through the individual production lines.

Then, on the way of each production line or at the last process, in order to examine whether the processed article meets regular quality, a plurality of measuring machines (measuring devices) are provided so as to measure the characteristics of the processed article.

Moreover, for example, the characteristics represent the size of the produced article, the performance of the article, such as bonding strength or the like, or quality, such as precision or the like. Hereinafter, the values indicating the characteristics are referred to as characteristic values.

By the way, in the above-described production method, there may be a case in which a characteristic value obtained by the measuring machine as the measurement result is out of a range of characteristic values when the processed article meets regular quality. The reason for this situation includes an adjustment inconsistency of the processing board, the processing machine, or the like, a measurement error of the measuring machine itself, and the like.

However, in order to produce high-quality articles, the processing board, the processing machine, the measuring machine, and the like need to be adjusted such that the characteristic value measured by the measuring machine falls within the range when the article meet regular quality.

As such, when the processing board, the processing machine, the measuring machine, and the like need to be adjusted, in the related art method, a person who is engaged in the production operation of the article, in particular, a skilled operator, experientially specifies and adjusts a device having the inconsistency according to the state of the characteristic value obtained from the measuring machine.

Moreover, as for the adjustment of the measurement error of the measuring machine, for example, in JP-A No. 10-132914 (published on May 22, 1998) (hereinafter referred as Patent Document 1), a calibration method of a measuring machine for a production line has been disclosed in which the individual measuring machines measure a standard article having the same reference characteristic, and a variation in the measurement results of the individual measuring machines is adjusted by use of the measuring result of the standard article.

In the configuration disclosed in Patent Document 1, when the inconsistency occurs in devices (for example, the processing machine or the like) other than the measuring machine, the skilled operator specifies the device to be adjusted on the basis of the state of the characteristic value measured by the measuring machine.

Further, in JP-A No. 2-74852 (published on Mar. 14, 1990) (hereinafter referred as Patent Document 2) and JP-A No. 10-132536 (published on May 22, 1998) (hereinafter referred as Patent Document 4), methods have been disclosed in which a cycle of defect to be generated in an article to be examined is measured. According to the related art methods, the defect which cyclically occurs can be detected.

Further, in JP-A No. 5-47619 (published on Feb. 26, 1993) (hereinafter referred as Patent Document 3), a meter for availability of a semiconductor device has been disclosed in which operation/non-operation is judged in a reference interval cycle of an operation signal from a semiconductor manufacturing apparatus with an error range and availability is measured. The meter for availability can accurately acquire operation time of the semiconductor manufacturing apparatus. For this reason, in the related art apparatus, the time for execution of a regular maintenance of the semiconductor device or for exchange of degraded parts can be grasped.

Further, in JP-A No. 2005-59070 (published on Mar. 10, 2005) (hereinafter referred as Patent Document 5), a method of manufacturing a copper bar has been disclosed. That is, in a method of manufacturing a copper bar by hot rolling, occurrence of a surface defect is expected from the measurement result of a surface by an alternating current magnetic flux. Then, a manufacturing condition is determined according to the expectation result, and a portion where the expected defect is to be present is removed. Accordingly, the defect can be detected/removed at an upstream process or the defect can be prevented.

However, in the related art method, the device to be adjusted is specified and adjusted depending on an experiential knowledge of the operator. As such, because of the dependency on the experiential knowledge of the operator, the device to be adjusted cannot be immediately specified, and thus productivity of the article is reduced.

However, in the related art configurations, when the article is processed by any one of a plurality of production processing devices, and the characteristic value is measured by any one of a plurality of measuring devices as the processing result, there is no disclosure of the configuration in which a device having an inconsistency is specified with superior accuracy.

Further, in the related art configurations, there is no disclosure of the configuration in which a specified production processing device is easily adjusted so as to reduce the variation of the characteristic values measured by the measuring devices at low cost, the ratio of occurrence of the inconsistency after the adjustment of the specified device is expected, and information in view of production efficiency is provided.

SUMMARY OF THE INVENTION

One or more embodiments of the invention provide an adjusting apparatus which can efficiently specify a device to be adjusted when a characteristic value measured from a produced article is out of a range of characteristic values in which the produced article meets regular quality, a production processing system, and a method of controlling an adjusting apparatus.

According to a first aspect of the present invention, there is provided an adjusting apparatus which receives characteristic values indicating quality of articles processed by one of m processing devices from one of n measuring devices and specifies a device to be adjusted, where m and n are natural numbers different from each other. The adjusting apparatus includes a judging unit that, on the basis of the characteristic values received from the measuring device, judges whether or not the processed articles meet regular quality, and a-specifying unit that, if the judging unit judges that the processed article does not meet regular quality, specifies the device to be adjusted according to whether an abnormal characteristic value, which is a characteristic value out of a range of characteristic values when the processed articles meet regular quality, appears by m cycles or n cycles.

According to this configuration, the adjusting apparatus has the judging unit, and thus it can be judged whether or not the processed article meets regular quality.

Moreover, the processing device includes, for example, devices, which process an article to be processed, such as a processing machine, a processing board, or the like.

As the case in which it is judged by the judging unit that the processed article does not meet regular quality, for example, a case in which the processing device is not normally operated, a case in which the measuring device is not normally operated, and the like can be exemplified.

For example, when the processing device is not normally operated, the characteristic value of the article processed by the corresponding processing device is out of the range of the characteristic values when the processed article meets regular quality. That is, when any one of the m processing devices is not normally operated, the characteristic value received from the measuring device becomes a value out of the range by the m cycles.

On the other hand, when the measuring device is not normally operated, the characteristic value measured by the measuring device is out of the range of the characteristic values in which the processed article meets regular quality. That is, when any one of the n measuring devices is not normally operated, the characteristic value received from the measuring device becomes a value out of the range by the n cycles.

Therefore, the specifying unit can specify either the processing device or the measuring device as the device to be adjusted on the basis of whether the cycle of occurrence of the characteristic value out of the range of the characteristic values, in which the processed article meets regular quality, is the m cycles or the n cycles.

As such, the adjusting apparatus according to the first aspect of the present invention includes the specifying unit, and thus the device to be adjusted can be specified on the basis of the cycle of occurrence of the characteristic value out of the range of the characteristic values in which the processed article meets regular quality. For this reason, in the adjusting apparatus according to the first aspect of the present invention, in order to specify the device to be adjusted, there is no need for manually performing a complex operation, such as setting adjustment of the processing device or the measuring device, and for examining which of the devices has abnormality.

That is, in the adjusting apparatus according to the first aspect of the present invention, the device to be adjusted can be efficiently specified, without changing setting of the processing device or the measuring device, or the like.

Therefore, in the adjusting apparatus according to the first aspect of the present invention, when the characteristic value measured from the processed article is out of the range of the characteristic values when the processed article meets regular quality, the device to be adjusted can be efficiently specified.

Further, the adjusting apparatus according to the first aspect of the present invention may further include a storage device that stores the characteristic values received from the measuring device in association with a sequence number in which the articles having the characteristic values are processed, and a cycle detecting unit that, on the basis of the characteristic values stored in the storage device, detects cyclicity of the abnormal characteristic value indicating whether the abnormal characteristic value appears by m cycles or n cycles. The specifying unit may specify the device to be adjusted on the basis of the detection result by the cycle detecting unit.

According to this configuration, the characteristic values received from the measuring device can be stored in the storage device in association with the sequence number in which the articles having the characteristic values are processed.

For this reason, on the basis of the characteristic values stored in the storage device, the cycle detecting unit can detect the cycle of occurrence of the characteristic value (the abnormal characteristic value) out of the range which is generated when the processing device or the measuring device is not normally operated.

Therefore, the specifying unit can efficiently specify the device to be adjusted on the basis of the detection result by the cycle detecting unit.

Further, the adjusting apparatus according to the first aspect of the present invention may further include a calculating unit that calculates a statistical feature of the characteristic values associated with cyclicity of the abnormal characteristic value on the basis of the characteristic values stored in the storage device. It is preferable that the cycle detecting unit determines to detect either the m cycles or the n cycles from cyclicity of the abnormal characteristic value to be detected on the basis of the statistical feature calculated by the calculating unit.

According to this configuration, the cycle detecting unit can determines whether or not to detect either the m cycles or the n cycles from cyclicity of the abnormal characteristic value to be detected on the basis of the statistical feature calculated by the calculating unit.

As such, the cycle detecting unit can determine cyclicity of the abnormal characteristic value on the basis of the statistical feature, such that the detection of cyclicity can be efficiently performed.

Therefore, in the adjusting apparatus according to the first aspect of the present invention, the cycle detecting unit can efficiently detect cyclicity, such that the device to be adjusted can be efficiently specified.

Further, in the adjusting apparatus according to the first aspect of the present invention, it is preferable that the characteristic values stored in the storage device be also stored in association with a number allocated to the measuring device which measures the characteristic values. The calculating unit may have a distribution feature calculating unit that, on the basis of the characteristic values stored in the storage device, divides the range of the characteristic values into predetermined sections and calculates distribution feature information indicating a feature of frequency distribution information of characteristic values included in a range of each section, and an individual defective fraction calculating unit that calculates an individual defective fraction, which is the ratio of the abnormal characteristic value with respect to the characteristic values measured by the measuring device.

According to this configuration, since the distribution feature calculating unit is provided, the feature of the frequency distribution information of the characteristic values can be calculated. Here, the frequency distribution information of the characteristic values is, for example, a histogram which represents a frequency distribution state of the characteristic value. Further, the distribution feature information is a frequency distribution feature of the characteristic value which appears in the histogram, for example, the number of sections in which the frequency is made larger than the frequency of the characteristic value belonging to the previous or next section.

For example, in a case in which any one of the m processing devices is not normally operated, in the histogram according to the characteristic value of the article processed by the corresponding processing device, the number of above-described sections is two. For this reason, in case of the distribution feature information in which the number of above-described sections is two, the abnormal characteristic value tends to appear by the m cycles. Accordingly, in case of the distribution feature information in which the number of above-described sections is two, the cycle detecting unit may detect whether or not the abnormal characteristic value appears by the m cycles.

Further, since the adjusting apparatus according to the first aspect of the present invention includes the individual defective fraction calculating unit, the ratios of the abnormal characteristic value with respect to the individual characteristic values measured by the measuring devices can be calculated.

For example, when any one of the n measuring devices is not normally operated, one of the ratios of the abnormal characteristic value calculated by the individual defective fraction calculating unit becomes large.

For this reason, when one of the ratios of the abnormal characteristic value calculated by the individual defective fraction calculating unit is made large, any one of the n measuring devices is likely to be not normally operated. Accordingly, when one of the ratios of the abnormal characteristic value becomes large, the cycle detecting unit may detect whether or not the abnormal characteristic value appears by the n cycles.

As such, in the adjusting apparatus according to the first aspect of the present invention, the cycle detecting unit can efficiently detect cyclicity of the abnormal characteristic value.

Therefore, in the adjusting apparatus according to the first aspect of the present invention, when the characteristic value measured from the processed article is out of the range of the characteristic values in which the processed article meets regular quality, the device to be adjusted can be efficiently specified.

Further, the adjusting apparatus according to the first aspect of the present invention may further includes a changing unit that, when the processing device is specified by the specifying unit as the device to be adjusted, changes a set value for defining the operation of the processing device, and a change instructing unit that instructs the changing unit to change the set value so as to cause the frequency distribution information to approximate to frequency distribution information in accordance with the characteristic value of the processed article which meets regular quality. In this case, it is preferable that the changing unit change the set value of one of the m processing devices in accordance with the change instruction by the change instructing unit.

Further, in the adjusting apparatus according to the first aspect of the present invention, the change instructing unit may instruct the changing unit to change the set value until frequency distribution information in accordance with a post-change characteristic value of an article processed after the set value is changed by the changing unit approximates to the frequency distribution information in accordance with the characteristic value to be obtained from the article which meets regular quality.

According to these configurations, the changing unit is provided, and thus, when the processing device is specified by the specifying unit as the device to be adjusted, the set value of the processing device can be changed. Moreover, the set value is a value for defining the operation of the processing device. With the change of the set value, quality of the article processed by the processing device is changed. That is, when the set value is changed, the characteristic value of the processed article is changed.

Further, since the change instructing unit is provided, through the change instructing unit, the adjusting apparatus can instruct the changing unit to change the set value such that the frequency distribution information of the measured characteristic value approximates to the frequency distribution information of the characteristic value of the processed article which meets regular quality. Further, the change instruction is performed with respect to the changing unit until the frequency distribution in accordance with the post-change characteristic value approximates to the frequency distribution information in accordance with the characteristic value to be obtained from the article which meets regular quality.

For this reason, the changing unit can change the set value of one of the m processing devices such that the article processed by the processing device meets regular quality.

Therefore, in the adjusting apparatus according to the first aspect of the present invention, when the characteristic value measured from the processed article is out of the range of the characteristic values in which the processed article meets regular quality, the device to be adjusted can be efficiently specified.

In addition, the device to be adjusted can be adjusted such that the characteristic value measured from the processed article falls within the range of the characteristic values in which the processed article meets regular quality.

Further, the adjusting apparatus according to the first aspect of the present invention may further include an output unit that outputs information indicating the device to be adjusted specified by the specifying unit.

According to this configuration, since the output unit is provided, the operator who is engaged in processing the article can see the device to be adjusted.

As such, the operator can easily see the device to be adjusted, and thus, even when any one of the m processing devices or any one of the n measuring devices is not normally operated, the adjustment of the processing device or the measuring device to be adjusted can be rapidly performed.

Further, the adjusting apparatus according to the first aspect of the present invention may further includes a degree-of-variation calculating unit that calculates a change amount of a degree of variation of the characteristic value before and after the adjustment of the device to be adjusted on the basis of the sum of power spectrum values when time series data, which is data indicating the relationship between the characteristic values measured by the measuring devices and the sequence number in which individual articles corresponding to the characteristic values are processed and the characteristic values thereof are measured, is subjected to frequency translation, a value indicating the degree of variation of all the characteristic values, and a power spectrum value in a frequency band corresponding to a specified cycle in which the abnormal characteristic value appears. The output unit may output information indicating the change amount of the degree of variation calculated by the degree-of-variation calculating unit.

According to this configuration, since the degree-of-variation calculating unit is provided, the change amount of the degree of variation of the characteristic value before and after the adjustment of the device to be adjusted can be calculated. Further, since the output unit outputs the calculation result of the degree-of-variation calculating unit, for example, an operator can see the change of the degree of variation of the characteristic value before and after the adjustment of the device to be adjusted on the basis of the output result by the output unit.

Therefore, the operator can see how the degree of variation is improved through the adjustment of the device specified as the device to be adjusted, and thus can judge whether or not to adjust the device specified by the specifying unit as the device to be adjusted.

Moreover, the calculation of the change amount of the degree of variation of the characteristic value before and after the adjustment of the device to be adjusted can be performed as described below, for example.

That is, when a frequency to be obtained through the arithmetic operation of time series data by an FFT is considered as a sine wave, an FFT power spectrum to be obtained from the arithmetic result by the FFT corresponds to the second power of amplitude of a frequency component for every cycle.

For this reason, the sum of the FFT power spectrums is substantially proportional to the second power of a standard deviation of time series data. Therefore, the relationship described below is established.

$$P\_all = K(\sigma\_all)^2 \quad (a)$$

(P_all is the sum of the FFT power spectrums before the adjustment of the device specified as the device to be adjusted)

(K is an arbitrary constant number)

($\sigma$_all is an overall standard deviation value before the adjustment of the device specified as the device to be adjusted)

Here, when it is assumed that the device specified by the specifying unit as the device to be adjusted is completely adjusted, a reduction amount of the degree of variation of the characteristic value, that is, a reduction amount $\sigma 3$ of the standard deviation to be generated by adjusting the device to be adjusted, can be represented by the following equation.

$$P3 = K(\sigma 3)^2 \quad (b)$$

(P3 is the value of the FFT power spectrum at a specified frequency where the abnormal characteristic value appears)

Here, if $\sigma 3$ is solved from the relationship between the equations (a) and (b), the change amount of the degree of variation of the characteristic value before and after the adjustment can be determined by $(\sigma 3 = \sigma\_all * \sqrt{(P3/P\_all)} \ldots (c))$.

Further, in the adjusting apparatus according to the first aspect of the present invention, it is preferable that the storage device also store variation tolerance information indicating a degree of variation which is judged that the adjustment of the device to be adjusted does not need to be preformed with respect to the characteristic values measured by the measuring device. The adjusting apparatus may further include an adjustment executing judging unit that, on the basis of the variation tolerance information stored in the storage device, a value indicating a degree of variation of all the characteristic values measured by the measuring devices, and the sum of power spectrum values when time series data, which is data indicating the relationship between the characteristic values and the sequence number in which individual articles corresponding to the characteristic values are processed and the characteristic values thereof are measured, is subjected to frequency translation, calculates a threshold value for judging whether or not the device to be adjusted specified by the specifying unit needs to be adjusted, compares the size of a spectrum at a specified frequency, at which the abnormal characteristic value appears when time series data is subjected to frequency translation, with the threshold value, and judges whether or not to perform the adjustment of a device specified by the specifying unit as the device to be adjusted.

Moreover, the variation tolerance information is a value which is acquired according to quality precision of an article to be produced or the like, and represents the change amount of the degree of variation of the measured characteristic value before and after the adjustment of the device to be adjusted specified by the specifying unit. Then, the variation tolerance information is set to a proper value by a user and is stored in the storage device in advance.

According to the above-described configuration, since the adjustment execution judging unit is provided, it can be judged whether or not the adjustment of the device to be adjusted needs to be performed. That is, in consideration of how the degree of variation of the characteristic value is changed through the adjustment of the device specified as the device to be adjusted, it can be automatically judged whether or not to adjust the device specified as the device to be adjusted.

Moreover, the threshold value for judging whether or not the adjustment of the device to be adjusted specified by the specifying unit needs to be performed can be acquired, for example, as described below.

That is, as described above, when the value (standard deviation) indicating the degree of variation of all the characteristic values, the characteristic values measured by the measuring devices, and the sequence number in which the individual articles having the characteristic values are processed and the characteristic values thereof are measured are considered as time series data, the relationship between all the power spectrums at the time of frequency translation by use of the FFT or the like and the power spectrum at a frequency corresponding to a specified cycle where the abnormal characteristic value is generated can be represented by '$\sigma 3 = \sigma\_all * \sqrt{(P3/P\_all)} \ldots (c)$'.

Here, when the value of the variation tolerance information is $\gamma 3$, and P3 (the value of the power spectrum at the frequency corresponding to the specified cycle where the abnormal characteristic value is generated) is Q3, which is the threshold value on whether or not to adjust the device to be adjusted, the following relationship is established from the equation (c) with respect to Q3.

$$Q3 = P\_all * (\gamma 3 / \sigma\_all)^2 \quad (d)$$

The threshold value Q3 calculated in such a manner is, for example, the FFT power spectrum indicating that the degree of variation of the characteristic value falls within a range in which the device to be adjusted does not need to be adjusted.

Here, the adjustment execution judging unit can compare the power spectrum acquired by the TFT or the like with respect to the actually measured characteristic value and judge whether or not the adjustment of the device to be adjusted needs to be performed.

Further, according to a second aspect of the present invention, a processing system includes the above-describe adjusting apparatus, m processing devices, each of which processes the article to be processed, and n measuring devices, each of which measures characteristic values indicating quality of the articles processed by one of the processing devices.

Since the processing system according to the second aspect of the present invention includes the above-described adjusting apparatus, when it is judged that the processed article does not meet regular quality on the measured characteristic value, the device to be adjusted can be efficiently specified.

Further, the device to be adjusted can be adjusted such that the characteristic value measured from the processed article falls within the range of the characteristic values in which the processed article meets regular quality.

Further, according to a third aspect of the present invention, there is provided a method of controlling a adjusting apparatus, which receives characteristic values indicating quality of articles processed by one of m processing devices from one of n measuring devices, and specifies a device to be adjusted, where m and n are natural numbers different from each other. The method includes a judging step of, on the basis of the characteristic values received from the measuring device, judging whether or not the processed articles meet regular quality, and a specifying step of, if it is judged in the judging step that the processed article does not meet regular quality, specifying the device to be adjusted according to whether an abnormal characteristic value, which is a characteristic value out of a range of characteristic values when the processed articles meet regular quality, appears by m cycles or n cycles.

As such, in the method of controlling an adjusting apparatus according to the third aspect of the present invention, when it is judged, on the basis of the measured characteristic value, that the processed article does not meet regular quality, the device to be adjusted can be efficiently specified.

Moreover, the individual units included in the adjusting apparatus can be implemented by a computer. In this case, a computer-readable recording medium on which a control program for an adjusting apparatus is recorded so as to implement the adjusting apparatus by the computer, which is operated as the individual units, also falls within the scope of the present invention.

As described above, according to the first aspect of the present invention, there is provided the adjusting apparatus which receives the characteristic values indicating quality of the articles processed by one of the m processing devices from one of the n measuring devices and specifies the device to be adjusted, where m and n are the natural numbers different from each other. The adjusting apparatus includes the judging unit that, on the basis of the characteristic values received from the measuring device, judges whether or not the processed articles meet regular quality, and the specifying unit that, if the judging unit judges that the processed articles do not meet regular quality, specifies the device to be adjusted according to whether the abnormal characteristic value, which is the characteristic value out of the range of characteristic values when the processed articles meet regular quality, appears by m cycles or n cycles.

Therefore, the specifying unit can specify either the processing device or the measuring device as the device to be adjusted on the basis of whether the cycle of occurrence of the characteristic value out of the range of the characteristic values in which the processed article meets regular quality is the m cycles or the n cycles.

In the adjusting apparatus according to the first aspect of the present invention, when the characteristic value measured from the processed article is out of the range of the characteristic values in which the processed article meets regular quality, the device to be adjusted can be efficiently specified.

Further, as described above, according to the second aspect of the present invention, the processing system includes the above-described adjusting apparatus, the m processing devices, each of which processes the article to be processed, and the n measuring devices, each of which measures the characteristic value indicating quality of the article processed one of the processing devices.

Since the processing system according to the second aspect of the present invention includes the above-described adjusting apparatus, when it is judged, on the basis of the measured characteristic value, that the processed article does not meet regular quality, the device to be adjusted can be efficiently specified.

Further, the device to be adjusted can be adjusted such that the characteristic value measured from the processed article falls within the range of the characteristic values in which the processed article meets regular quality.

Further, as described above, there is provided the method of controlling an adjusting apparatus, which receives the characteristic values indicating quality of the articles processed by one of the m processing devices from one of the n measuring devices, and specifies the device to be adjusted, where m and n are natural numbers different from each other. The method includes a judging step of, on the basis of the characteristic values received from the measuring device, judging whether or not the processed articles meet regular quality, and a specifying step of, if it is judged in the judging step that the processed articles do not meet regular quality, specifying the device to be adjusted according to whether an abnormal characteristic value, which is a characteristic value out of a range of characteristic values when the processed articles meet regular quality, appears by m cycles or n cycles.

As such, in the method of controlling an adjusting apparatus according to the third aspect of the present invention, when it is judged, on the basis of the measured characteristic value, that the processed article does not meet regular quality, the device to be adjusted can be efficiently specified.

Further, according to a fourth aspect of the present invention, there is provided an adjusting apparatus which is included in a production system having at least two kinds of production processing devices for executing a processing of articles to be produced and a measurement processing of characteristic values indicating quality of the processed articles as production processing, and two or more first production processing devices for performing a first production processing and two or more second production processing devices for performing a second production processing. The adjusting apparatus includes a data collecting unit that collects the characteristic values measured by the production processing devices for executing the measurement processing and, when a transfer sequence number of the articles corresponding to the characteristic values is considered as a time axis, creates time series data indicating the change of the characteristic value according to the time axis, a translation calculating unit that performs frequency translation on time series data created by the data collecting unit so as to calculate frequency data, a specifying unit that specifies a device, which can be estimated that an inconsistency occurs, from the production processing device as a device to be adjusted on the basis of frequency data calculated by the translation calculating unit, a setting unit that sets a production processing device in the operation state from the production processing devices corresponding to the individual production processings, and a number-of-devices control . . . unit that, when the number of first production processing devices in the operation state and the number of second production processing devices in the operation state are m and n, respectively, where m<n, controls the setting unit so as to change the number of n and/or the number of m.

Moreover, for example, when the production processing device is a device for processing the article to be produced, the operation in the production processing device represents the execution of the device. Further, for example, when the production processing device is a processing board which fixes the articles for processing, the operation represents the state in which the article is fixed. That is, the operation in the production processing device is broadly used to mean the state of the production processing device when the production processing of the article is executed.

According to this configuration, since the setting unit is provided, the number of first production processing devices in the operation state and the number of second production processing devices in the operation state can be set. That is, in the production system, it is configured such that the number of first production processing devices in the operation state and the number of second production processing devices in the operation state can be changed.

Further, in the adjusting apparatus according to the fourth aspect of the present invention, the number-of-devices control unit is provided. Therefore, when the number of first production processing devices in the operation state and the number of second production processing devices in the operation state are m and n, respectively, where m<n, the number of n and/or the number of m can be changed by controlling the setting unit.

For this reason, in the adjusting apparatus according to the fourth aspect of the present invention, when cyclicity of the change of the characteristic value is analyzed by use of frequency data translated by the translation calculating unit and the device to be adjusted is specified from cyclicity, frequency components in frequency data are prevented from overlapping each other and the device to be adjusted can be specified.

Therefore, in the adjusting apparatus according to the fourth aspect of the present invention, the device to be adjusted can be specified with superior accuracy.

Further, in the adjusting apparatus according to the fourth aspect of the present invention, it is preferable that the setting unit manage setting information indicating the number of first processing devices in the operation state and the number of second processing devices in the operation state, and the number-of-devices control unit acquire the setting information from the setting unit and controls to change the number of first processing devices in the operation state and/or the number of second processing devices in the operation state on the basis of the acquired setting information.

According to this configuration, the setting unit manages the setting information indicating the number of first production processing devices in the operation state and the number of second production processing devices in the operation state. Therefore, from the first production processing devices and the second production processing devices, the number of devices to be currently operated can be grasped.

Further, the number-of-devices control unit can control the setting unit to change the number of first production processing devices and/or the number of second production processing devices on the basis of the setting information acquired from the setting unit.

For this reason, the adjusting apparatus can set the number of first production processing devices and/or the number of second production processing devices such that, from the number of first production processing devices in the operation state and the number of second production processing devices in the operation state, one becomes a double of the other.

Therefore, in the adjusting apparatus according to the fourth aspect of the present invention, the device to be adjusted can be specified with superior accuracy.

Further, in the adjusting apparatus according to the fourth aspect of the present invention, when the change of the number of production processing devices is controlled by decreasing the number of devices in the operation state, the number-of-devices control unit may control the change of the number of devices such that, from the first production processing devices and the second production processing devices, one having a larger number of devices in the operation state has priority over the other. In addition, when the change of the number of production processing devices is controlled by increasing the number of devices in the operation state, the number-of-devices control unit may control the change of the number of devices such that, from the first production processing devices and the second production processing devices, one having a smaller number of devices in the operation state has priority over the other.

According to this configuration, at the time of controlling the change of the number of production processing devices by decreasing the number of devices in the operation state, the number-of-devices control unit can control the change of the number of devices such that, from the first production processing devices and the second production processing devices, one having a larger number of devices in the operation state has priority over the other. For this reason, production efficiency can be suppressed from being decreased, as compared with a case of being decreased from the other having a smaller number of devices in the operation state.

Further, at the time of controlling the change of the number of production processing devices by increasing the number of devices in the operation state, the number-of-devices control unit can control the change of the number of devices such that, from the first production processing devices and the second production processing devices, one having a smaller number of devices in the operation state has priority over the other. For this reason, production efficiency can be further enhanced, as compared with a case of being decreased from the other having a larger number of devices in the operation state.

Further, the adjusting apparatus according to the fourth aspect of the present invention may further include an extracting unit that extracts a power spectrum of a frequency according to the number of production processing devices in the operation state on the basis of frequency data calculated by the translation calculating unit. It is preferable that the specifying unit specify the device to be adjusted on the basis of integral values according to the individual production processing devices extracted by the extracting unit.

According to this configuration, since the extracting unit is provided, the power spectrum of the frequency according to the number of production processing devices in the operation state can be extracted. Further, the adjusting apparatus can specify the device to be adjusted on the basis of the integral value of the power spectrums according to the individual production processing devices.

That is, in the adjusting apparatus according to the fourth aspect of the present invention, only the change of the characteristic values due to the individual production processing devices can be used to specify the device to be adjusted. Therefore, even when other reasons for abnormality, which are not caused by abnormality of any one of the production processing devices, are included, the device to be adjusted can be accurately specified.

Further, in the adjusting apparatus according to the fourth aspect of the present invention, the data collecting unit may receive the characteristic values measured by the production processing devices for executing the measurement processing according to an instruction from the setting unit while delaying by the amount of time lapse from a point of time, at which the production processing device in the operation state is changed, until the articles are produced by the production processing device in the operation state after the change, and may create time series data on the basis of the characteristic values.

Moreover, the change occurring in the production processing device in the operation state is, for example, the change of the number of production processing devices in the operation state or the production processing device in the operation state for production.

Therefore, the data collecting unit can receive the characteristic values of the articles produced from the point of time at which the change in the production processing device in the operation state occurs. That is, the characteristic values of the articles produced before the change in the production processing device in the operation state occurs can be prevented from being received.

For this reason, in the adjusting apparatus according to the fourth aspect of the present invention, reliability of frequency data calculated by the translating unit can be enhanced.

Further, the adjusting apparatus according to the fourth aspect of the present invention may further include an information output unit that outputs the setting information acquired from the setting unit by the number-of-devices control unit.

According to this configuration, since the output unit for outputting the setting information is provided, the production processing device in the operation state or to be stopped can be specified.

Therefore, a user can easily grasp the production processing device to be currently operated, and thus the management of the production processing devices can be efficiently performed.

According to a fifth aspect of the present invention, there is provided an adjusting apparatus which is included in a production system having at least two kinds of production processing devices for executing a processing of articles to be produced and a measurement processing of characteristic values indicating quality of the processed articles as production processing, and two or more first production processing devices for performing a first production processing and two or more second production processing devices for performing a second production processing. The adjusting apparatus includes a data collecting unit that collects the characteristic values measured by the production processing devices for executing the measurement processing and, when a transfer sequence number of the articles corresponding to the characteristic values is considered as a time axis, creates time series data indicating the change of the characteristic value according to the time axis, a translation calculating unit that performs frequency translation on time series data created by the data collecting unit so as to calculate frequency data, an extracting unit that extracts a power spectrum of a frequency according to the number of production processing devices in the operation state on the basis of frequency data calculated by the translation calculating unit, a specifying unit that specifies a device, which can be estimated that an inconsistency occurs, from the production processing device as a device to be adjusted on the basis of the power spectrum of the frequency according to the number of production processing devices in the operation state, which is extracted by the extracting unit, a setting unit that sets a production processing device in the operation state from the production processing devices corresponding to the individual production processings, and a number-of-devices control unit that controls the setting unit on the basis of time series data created by the data collecting unit.

According to this configuration, since the adjusting apparatus according to the fifth aspect of the present invention has the number-of-devices control unit, any one of the first production processing devices or any one of the second production processing devices can sequentially stop on the basis of time series data, for example, until the size of the shift of the characteristic values caused by the first production processing device or the second production processing device specified as the device to be adjusted is reduced.

Further, in the adjusting apparatus according to the fifth aspect of the present invention, as for the first production processing device or the second production processing device specified as the device to be adjusted, the first production processing device or the second production processing device having abnormality can be specified with superior accuracy, and thus the operation thereof can be sequentially stopped.

For this reason, in the adjusting apparatus, by repeating the fine adjustment, the adjustment can be performed such that the size of the shift from a regular value of the characteristic value is reduced, without providing a special adjusting unit.

Further, in the adjusting apparatus according to the fifth aspect of the present invention, it is preferable that the number-of-devices control unit sequentially stop the operation of any one of the production processing devices until the integral value of the power spectrum or the frequency corresponding to the production processing device specified by the specifying unit as the device to be adjusted is equal to or less than a predetermined value.

By the way, the predetermined value is a value set in a tolerance range of the measured characteristic values, and is determined according to desired quality of the article to be produced. Further, it has been known that the integral value of the frequency power spectrums is substantially proportional to the second power of the standard deviation in time series data of the characteristic value. That is, that the integral value of the frequency power spectrums is equal to or less than the predetermined value means that the variation with respect to the regular value in the measurement result of the characteristic value falls within the desired range.

Therefore, by stopping the operation of any one of the production processing devices, when the integral value of the frequency power spectrums is equal to or less then the predetermined value, the operation of the device having abnormality can be considered to be stopped.

According to this configuration, in the adjusting apparatus according to the fifth aspect of the present invention, the number-of-devices control unit can sequentially stop the operation of any one of the production processing devices or any one of the measuring devices until the integral value of the frequency power spectrums corresponding to the production processing device or the measuring device specified as the device to be adjusted is equal to or less than the predetermined value.

That is, in the adjusting apparatus according to the fifth aspect of the present invention, as for the production processing device specified as the device to be adjusted, the production processing device having abnormality can be specified with superior accuracy, and thus the operation thereof can be stopped.

For this reason, in the adjusting apparatus, by repeating the fine adjustment, the adjustment can be performed such that the variation of the characteristic value measured by the measuring device with respect to the regular value is reduced, without providing a special adjusting unit.

Further, in the adjusting apparatus according to the fifth aspect of the present invention, the number-of-devices control unit may calculate a standard deviation of the characteristic values on the basis of time series data created by the data collecting unit and may sequentially stop the operation of any one of the production processing devices until the calculated standard deviation is equal to or less then the predetermined value.

By the way, the predetermined value is a value set within the tolerance range of the variation of the measured characteristic value, and is determined according to desired quality of the article to be produced.

Therefore, when the standard deviation is equal to or less than the predetermined value by stopping the operation of any one of the production processing devices, the variation of the characteristic value can be reduced, and the operation of the device having abnormality can be stopped.

According to this configuration, in the adjusting apparatus according to the fifth aspect of the present invention, the number-of-devices control unit can sequentially stop the operation of any one or the production processing devices until the standard deviation of the measured characteristic values is equal to or less than the predetermined value.

That is, in the adjusting apparatus, as for the production processing device or the measuring device specified as the device to be adjusted, the production processing device or the measuring device having abnormality can be specified with superior accuracy, and thus the operation thereof can be stopped.

For this reason, in the adjusting apparatus, by repeating the fine adjustment, the adjustment can be performed such that the variation of the characteristic value measured by the measuring device with respect to the regular value is reduced, without providing a special adjusting unit.

Further, the adjusting apparatus according to the fifth aspect of the present invention may further include a masking unit that divides a mask component which is a power spectrum of a frequency according to m or n or a power spectrum of a frequency of an integer multiple of the frequency from frequency data, and a non-mask component which is a power spectrum excluding the power spectrum, from frequency data, and a inverse-translating unit that performs frequency inverse-translation on any one of the mask component and the non-mask component divided by the masking unit so as to calculate the value of time series data. The number-of-devices control unit may sequentially stop the operation or any one of the production processing devices specified by the specifying unit as the article to the adjusted until the value of time series data obtained by performing frequency inverse-translation on the mask component by the inverse-translating unit is equal to or less than a predetermined value.

By the way, the mask component does not include the offset component, and show only the variation of the characteristic value corresponding to a frequency band extracted as the mask component. Therefore, with time series data obtained as the result of a reverse FFT of the mask component, only the shift width of the characteristic value due to abnormality of the device is shown.

Then, when the value of time series data is equal to or less than the predetermined value by stopping the operation of any one of the production processing devices, the operation of the device having abnormality can be considered to be stopped.

According to this configuration, in the adjusting apparatus according to the fifth aspect of the present invention, the number-of-devices control unit can sequentially stop the operation of any one of the production processing devices or any one of the measuring devices until the value of time series data subjected to a frequency inverse-translation by the inverse-translating unit is equal to or less than the predetermined value.

That is, in the adjusting apparatus according to the fifth aspect of the present invention, as for the production processing device specified as the device to be adjusted, the production processing device having abnormality can be specified with superior accurately, and thus the operation thereof can be stopped.

For this reason, in the adjusting apparatus, by repeating the fine adjustment, the adjustment can be performed such that the variation of the characteristic value measured by the measuring device with respect to the regular value is reduced, without providing a special adjusting unit.

Further, the adjusting apparatus according to the fifth aspect of the present invention may further include a first data output unit that output a value obtained by the inverse-translating unit on the basis of the non-mask component. The value outputted from the first data output unit may be the number of values out of a regular range of characteristic values, in which the produced articles meet regular quality, from the values of time series data obtained on the basis of the non-mask component or a standard deviation of the values of time series data obtained on the basis of the non-mask component.

By the way, the non-mask component is the residual when the mask component is extracted from the value obtained by performing frequency translation on time series data on the basis of the measured characteristic values. Further, as described above, the mask component shows only the variation of the characteristic value caused by the specified device. To the contrary, in the non-mask component, the variation of the characteristic value can be shown when the variation of the characteristic value caused by the device is solved.

According to this configuration, since the first data output unit is provided, from the values of time series data obtained on the basis of the non-mask component, the number of values out of the regular range of the characteristic values in which the produced article meets regular quality or the standard deviation of the values of time series data obtained on the basis of the non-mask component can be outputted.

Then, in the adjusting apparatus according to the fifth aspect of the present invention, the first data output unit can output the number of values out of the regular range of the characteristic values from the values of time series data obtained on the basis of the non-mask component.

In this case, in the adjusting apparatus according to the fifth aspect of the present invention, when it is assumed that the variation of the characteristic value caused by the device specified as the device to be adjusted is solved, the number of characteristic values exceeding the range of the characteristic values when the produced article meets regular quality can be outputted.

That is, in the adjusting apparatus according to the fifth aspect of the present invention, through the adjustment of abnormality of the production processing device or the measuring device, it can be expected that the shift of the characteristic value from the regular value range is improved to some extend.

As such, with the adjustment of abnormality of the production processing device or the measuring device, it can be expected how the shift of the characteristic value is improved. Therefore, before performing an actual adjustment processing, it is possible to determine whether or not to perform the adjustment of the production processing device or the measuring device specified as the device to be adjusted.

Further, when the values of time series data are shown, together with information indicating the range when the characteristic value is recognized to be normal, the shift of the characteristic value from the regular range when it is assumed that abnormality of the production processing device specified as the device to be adjusted is adjusted can be grasped.

That is, with the adjustment of abnormality of the production processing device, it can be expected how the shift the characteristic value from the regular range is improved.

Further, in the adjusting apparatus according to the fifth aspect of the present invention, the standard deviation of the values of time series data obtained on the basis of the non-mask component can be outputted. For this reason, in the adjusting apparatus according to the fifth aspect of the present invention, when it is assumed that the variation of the characteristic value caused by the device specified as the device to be adjusted is solved, the variation of the characteristic value can be expected.

That is, in the adjusting apparatus according to the fifth aspect of the present invention, it can be expected how the variation of the characteristic value is improved, after the adjustment of abnormality of the production processing device or the measuring device.

As such, with the adjustment of abnormality of the production processing device, it can be expected how the shift of the characteristic value is improved. Therefore, before performing the actual adjustment processing, it is possible to determine whether or not to perform the adjustment of the production processing device specified as the device to be adjusted.

For example, even when the production processing device is adjusted, when it is expected that the shift of the characteristic value from the regular range cannot be significantly improved, the adjustment processing is not performed. That is, in view of production efficiency of the article to be produced, necessity for the adjustment of the production processing device can be determined.

Therefore, in the adjusting apparatus according to the fifth aspect of the present invention, in view of production efficiency, the information for determining whether or not to perform the adjustment of the device to be adjusted can be provided.

Further, the adjusting apparatus according to the fifth aspect may further include a second data output unit that outputs the values of time series data obtained by the inverse-translating unit on the basis of the mask component.

According to this configuration, the values of time series data obtained on the basis of the mask component can be outputted.

By the way, the values of time series data obtained through frequency inverse-translation of the mask component can show the shift of the characteristic value, excluding the offset component, such as white noise or the like.

For this reason, in the adjusting apparatus according to the fifth aspect of the present invention, the shift of the characteristic value of the article to be produced due to the production processing device or the measuring device specified as the device to be adjusted can be shown.

As such, by outputting data generated through inverse-translation of only frequency data of the mask component, the mode of the shift of an individual device can be shown with high precision.

According to a sixth aspect of the present invention, there is provided a method of controlling an adjusting apparatus which is included in a production system having at least two kinds of production processing devices for executing a processing of articles to be produced and a measurement processing of characteristic values indicating quality of the processed articles as production processing, and two or more first production processing devices for performing a first production processing and two or more second production processing devices for performing a second production processing. The method of controlling an adjusting apparatus includes a step of collecting the characteristic values measured by the production processing devices for executing the measurement processing and, when a transfer sequence number of the articles corresponding to the characteristic values is considered as a time axis, creating time series data indicating the change of the characteristic value according to the time axis, a step of performing frequency translation on created time series data so as to calculate frequency data, a step of specifying a device, which can be estimated that an inconsistency occurs, from the production processing device as a device to be adjusted on the basis of calculated frequency data, a step of setting a production processing device in the operation state from the production processing devices corresponding to the individual production processings, and a step of, when the number of first production processing devices in the operation state and the number of second production processing devices in the operation state are m and n, respectively, where m<n, controlling so as to change the number of n and/or the number of m.

According to this method, in the step of setting the production processing device in the operation state, the number of first production processing devices in the operation state and the number of second production processing devices in the operation state can be set. That is, in the method of controlling an adjusting apparatus according to the sixth aspect of the present invention, the number of first production processing devices in the operation state and the number of second production processing devices in the operation state can be changed.

Further, in the method of controlling an adjusting apparatus according to the sixth aspect of the present invention, when the number of first production processing devices in the operation state and the number of second production processing devices in the operation state are m and n, respectively, where m<n, and when n is the double of m, the number of n and/or the number of m can be changed.

For this reason, when cyclicity of the change of the characteristic value is analyzed by use of translated frequency data and the device to be adjusted is specified from cyclicity, frequency components in frequency data are prevented from overlapping each other and the device to be adjusted can be specified.

Therefore, in the method of controlling an adjusting apparatus according to the sixth aspect of the present invention, the device to be adjusted can be specified with superior accuracy.

According to a seventh aspect of the present invention, a production system includes the above-described adjusting apparatus, production processing devices that produces articles to be produced; and measuring devices that measure characteristic values indicating quality of the articles produced by the production processing devices.

For this reason, in the production system according to the seventh aspect of the present invention, the device to be adjusted can be specified with superior accuracy.

Moreover, the adjusting apparatus can be implemented by a computer. In this case, a computer-readable recording medium on which a control program for an adjusting apparatus is recorded so as to implement the adjusting apparatus by the computer, which is operated as the individual units, also falls within the scope of the present invention.

As described above, according to the seventh aspect of the present invention, there is provided the adjusting apparatus which is included in the production system having at least two kinds of production processing devices for executing the processing of articles to be produced and the measurement processing of characteristic values indicating quality of the processed articles as production processing, and two or more first production processing devices for performing the first production processing and two or more second production processing devices for performing the second production processing. The adjusting apparatus includes the data collecting unit that collects the characteristic values measured by the production processing devices for executing the measurement processing and, when the transfer sequence number of the articles corresponding to the characteristic values is considered as the time axis, creates time series data indicating the change of the characteristic value according to the time axis, the translation calculating unit that performs frequency translation on time series data created by the data collecting unit so as to calculate frequency data, the specifying unit that specifies the device, which can be estimated that the inconsistency occurs, from the production processing device as the device to be adjusted on the basis of frequency data calculated by the translation calculating unit, the setting unit that sets the production processing device in the operation state from the production processing devices corresponding to the individual production processings, and the number-of-devices control unit that, when the number of first production processing devices in the operation state and the number of second production processing devices in the operation state are m and n, respectively, where m<n, controls the setting unit so as to change the number of n and/or the number of m.

Therefore, in the adjusting apparatus according to the fourth aspect of the present invention, the device to be adjusted can be specified with superior accuracy.

As described above, according to the fifth aspect of the present invention, there is provided the adjusting apparatus which is included in the production system having at least two kinds of production processing devices for executing the processing of articles to be produced and the measurement processing of characteristic values indicating quality of the processed articles as production processing, and two or more first production processing devices for performing the first production processing and two or more second production processing devices for performing the second production processing. The adjusting apparatus includes the data collecting unit that collects the characteristic values measured by the production processing devices for executing the measurement processing and, when the transfer sequence number of the articles corresponding to the characteristic values is considered as the time axis, creates time series data indicating the change of the characteristic value according to the time axis, the translation calculating unit that performs frequency translation on time series data created by the data collecting unit so as to calculate frequency data, the extracting unit that extracts the power spectrum of the frequency according to the number of production processing devices in the operation state on the basis of frequency data calculated by the translation calculating unit, the specifying unit that specifies the device, which can be estimated that the inconsistency occurs, from the production processing device as the device to be adjusted on the basis of the power spectrum of the frequency according to the number of production processing devices in the operation state, which is extracted by the extracting unit, the setting unit that sets the production processing device in the operation state from the production processing devices corresponding to the individual production processings, and the number-of-devices control unit that controls the setting unit on the basis of time series data created by the data collecting unit.

Therefore, in the adjusting apparatus, by repeating the fine adjustment, the adjustment can be performed such that the size of the shift from the regular value of the characteristic value is reduced, without providing the special adjusting unit.

As described above, according to the sixth aspect of the present invention, there is provided the method of controlling an adjusting apparatus which is included in the production system having at least two kinds of production processing devices for executing the processing of articles to be produced and the measurement processing of characteristic values indicating quality of the processed articles as production processing, and two or more first production processing devices for performing the first production processing and two or more second production processing devices for performing the second production processing. The method of controlling an adjusting apparatus includes a step of collecting the characteristic values measured by the production processing devices for executing the measurement processing and, when the transfer sequence number of the articles corresponding to the characteristic values is considered as the time axis, creating time series data indicating the change of the characteristic value according to the time axis, a step of performing frequency translation on created time series data so as to calculate frequency data, a step of specifying the device, which can be estimated that the inconsistency occurs, from the production processing device as the device to be adjusted on the basis of calculated frequency data, a step of setting the production processing device in the operation state from the production processing devices corresponding to the individual production processings, and a step of, when the number of first production processing devices in the operation state and the number of second production processing devices in the operation state are m and n, respectively, where m<n, controlling so as to change the number of n and/or the number of m.

Therefore, in the method of controlling an adjusting apparatus according to the sixth aspect of the present invention, the device to be adjusted can be specified with superior accuracy.

BRIEF DESCRIPTION OF THE DRAWINGS

FIGS. 3A to 3D are diagrams showing the relationship between a sequence number of articles, the characteristic values of which are measured, and the characteristic values of the individual articles.

FIG. 4 is a table showing the results of arithmetic operations of equations (2), (3), and (4) when the characteristic values are within a regular range, when the characteristic values are out of the regular range for every one, when the characteristic values are out of the regular range for every two, and when the characteristic values are out of the regular range for every eleven.

FIG. 17A shows a diagram showing an example of the relationship between the characteristic values measured from the articles, and a transfer sequence number of the articles corresponding to the individual characteristic values in a case in which any one of eight processing machines is not normally operated.

FIG. 17B shows a diagram showing an example of the relationship between the characteristic values measured from the articles, and a transfer sequence number of the articles corresponding to the individual characteristic values in a case in which any one of sixteen processing boards is not normally operated.

FIG. 17C shows a diagram showing an example of the relationship between the characteristic values measured from the articles, and a transfer sequence number of the articles corresponding to the individual characteristic values in a case in which any one of three measuring machines is not normally operated.

FIG. 18A is a diagram showing an example in which the association relationship between the characteristic values and the transfer sequence number of the articles corresponding to the characteristic values, and FIG. 18B is a diagram showing an example of frequency data obtained through frequency translation by a fast Fourier translation on the basis of time series data.

FIG. 19A is a diagram showing an example in which the association relationship between the characteristic values and the transfer sequence number of the articles corresponding to the characteristic values, and FIG. 19B is a diagram showing an example of frequency data obtained through frequency translation by a fast Fourier translation on the basis of time series data.

FIG. 20A is a diagram showing an example in which the association relationship between the characteristic values and the transfer sequence number of the articles corresponding to the characteristic values, and FIG. 20B is a diagram showing an example of frequency data obtained through frequency translation by a fast Fourier translation on the basis of time series data.

FIG. 23A shows an example in which the relationship between the characteristic values and the transfer sequence number of the articles corresponding to the characteristic values, and FIG. 23B is a histogram showing a variation rating of the characteristic values.

DETAILED DESCRIPTION OF THE INVENTION

Figure 1:
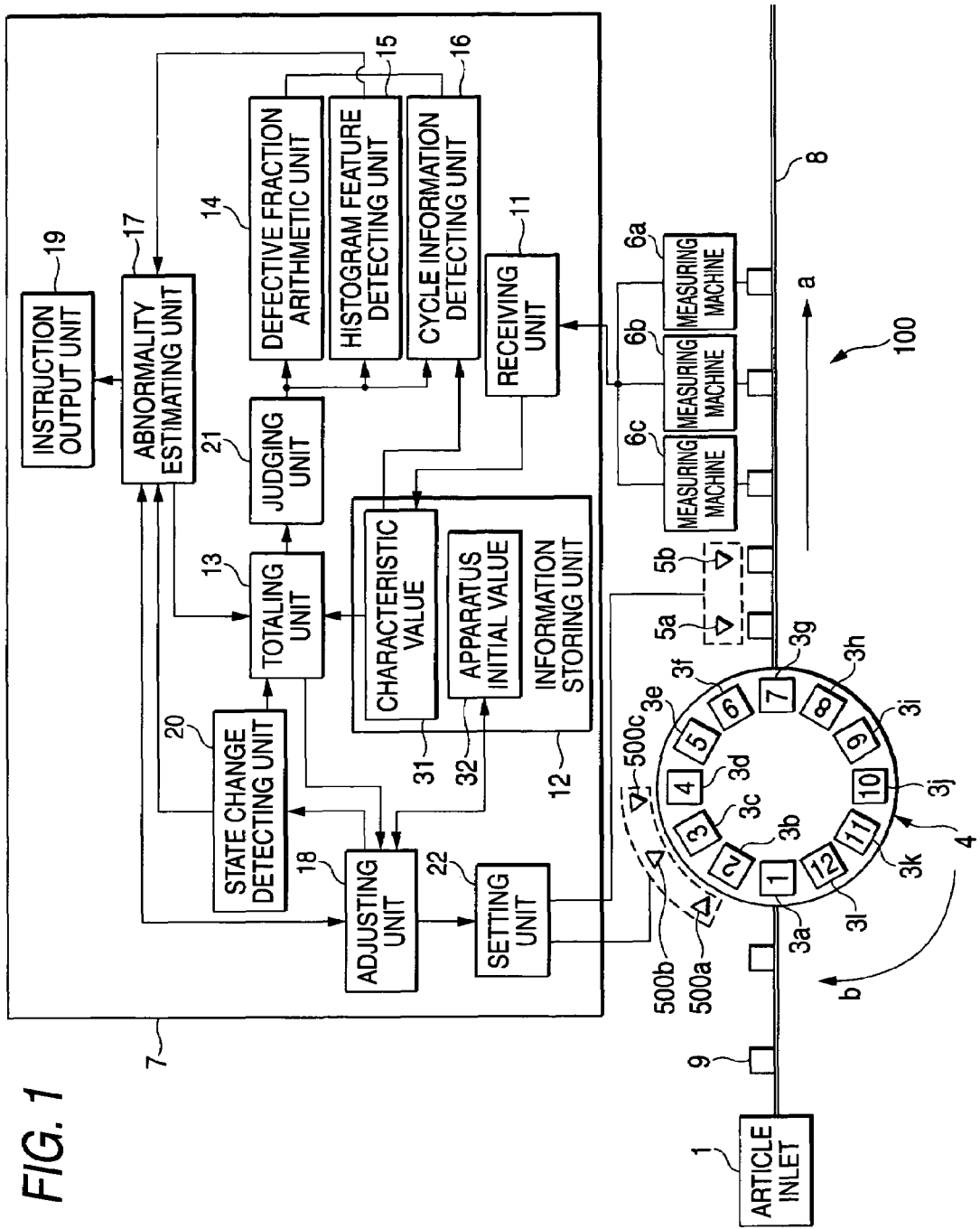
FIG. 1 is a block diagram showing an essential configuration of a manufacturing line system, which relates to a first embodiment of the present invention.

Hereinafter, an embodiment of the present invention will be described with reference to FIGS. 1 to 13. As shown in FIG. 1, a manufacturing line system (processing system) 100 according to the present embodiment executes a first processing by three first processing machines 500a to 500c, which perform different processings on an article 9 to be processed (article to be produced). Further, the manufacturing line system 100 executes a second processing by any one of two second processing machines (production processing devices) 5a to 5b, which execute the same processing on the article 9. Further, the manufacturing line system 100 is configured to examine quality of the article 9 processed by any one of three measuring machines (measuring devices) 6a to 6c. That is, in the manufacturing line system 100, different processings are executed by the first processing machines 500a to 500c. Then, two second processing machines 5a to 5b can process two articles 9 in parallel, and three measuring machines 6a to 6c can measure the characteristic values of three articles 9 in parallel. Further, as for different processings, for example, the first processing machine 500a performs a processing for inserting parts into the article 9, the first processing machine 500b performs a processing for bending the article 9, and the first processing machine 500c performs a processing for welding the article 9.

Moreover, FIG. 1 is a block diagram showing an essential configuration of the manufacturing line system according to the first embodiment of the present invention.

As shown in FIG. 1, the manufacturing line system 100 according to the first embodiment has an article inlet 1, a transfer belt 8, the first processing machines 500a to 500c, processing boards (production processing devices) 3a to 3l, a turntable 4, the second processing machines (production processing devices) 5a and 5b, the measuring machines (measuring devices) 6a to 6c, and an adjusting apparatus 7.

An operator, who operates the manufacturing line system 100 according to a first aspect of the present invention, drops the article 9 in to the article inlet 1 in order to process the articles 9. And, the inlet article is transferred as the way of the processing boards (production processing devices) 3a to 3l.

The transfer belt 8 is provided to transfer the articles 9 to be processed. Specifically, the transfer belt 8 transfers the articles 9 inputted to the inlet 1 up to the processing board 3a to 3l or transfers the processed articles 9 after the first processing from the processing board 3a to 3l up to a position fading the second processing machine 5a to 5b which executes the second processing, or transfers the processed articles 9 after the second processing up to a position facing the measuring machine 6a to 6c. Further, when an additional process is required, the transfer belt 8 transfers the articles, which are measured by the measuring machines 6a to 6c, up to a place where a device for executing a next process is provided. Moreover, the transfer direction of the transfer belt 8 at the time of working is a direction of an arrow a shown in FIG. 1.

Further, when a characteristic value 31 measured by each of the measuring machines 6a to 6c is out of a range of characteristic values in which the processed article meets regular quality, the transfer belt 8 moves the article having the characteristic value 31 so as to be removed from a manufacturing line.

The processing boards 3a to 3l are provided to fix the articles so as to be processed by the first processing machines 500a to 500c. In the manufacturing line system 100 according to the present embodiment, the twelve processing boards 3a to 3l are provided along the outer circumference of the circular turntable 4, as shown in FIG. 1. Then, the processing boards 3a to 3l are configured to be moved in a direction of an arrow b (a clockwise direction) according to the rotation of the turntable 4.

That is, the article transferred by the transfer belt 8 is provided in one of the processing boards 3a to 3l. If the article is provided in one of the processing boards 3a to 3l, the processing board with the article provided therein is moved in the direction of the arrow b by the amount corresponding to one processing board. Then, a newly transferred article is provided in a processing board which is aligned with the transfer belt 8.

The turntable 4 rotates in the direction of the arrow b so as to move the processing board 3a to 3l up to a processing place by the first processing machine 500a to 500c. Further, the turntable 4 can move the article 9, which is subjected to the first processing by the first processing machine 500a to 500c, up to the transfer belt 8, which transfers the article up to a processing position by the second processing machine 5a to 5b, which executes the second processing.

That is, the turntable 4 can provide the articles 9 transferred by the transfer belt 8 in the processing boards 3a to 3l one by one, and move the processing boards 3a to 3l at a speed at which the first processing machines 500a to 500c can process the articles 9. In addition, in order to load the article 9 after the first processing on the transfer belt 8 so as to be transferred up to the second processing machine 5a to 5b, which executes the second processing, the turntable 4 rotates so as to move the article 9 from the processing position of the first processing machine 500a to 500c up to the transfer belt 8.

Moreover, the rotation speed of the turntable 4 meets the following conditions. That is, the rotation speed is set such that the articles transferred by the transfer belt 8 can be correspondingly provided in the processing boards 3a to 3l. Further, the rotation speed is set such that the provided articles can be processed by the first processing machines 500a to 500c. In addition, the rotation speed is adjusted such that the processed articles can be moved to the transfer belt 8 which transfers the processed articles up to the second processing machines 5a to 5b.

The individual first processing machines 500a to 500c perform a predetermined processing with respect to the individual articles provided in the processing boards 3a to 3l. In the manufacturing line system 100 according to the present embodiment, as shown in FIG. 1, the three first processing machines 500a to 500c are provided so as to perform the different processing on the individual articles to be disposed in front of the first processing machines 500a to 500c in parallel.

That is, in the manufacturing line system 100 according to the present embodiment, the processing can be simultaneously performed on the three articles by the three first processing machines 500a to 500c.

The individual second processing machines 5a to 5b perform a predetermined processing with respect to the individual articles. In the manufacturing line system 100 according to the present embodiment, as shown in FIG. 1, the two second processing machines 5a to 5b are provided so as to perform the same processing on the transferred articles.

The individual measuring machines 6a to 6c measure the characteristic values 31 of the individual articles in order to examine quality of the processed article. In the manufacturing line system 100, as shown in FIG. 1, the three measuring machines 6a to 6c are individually provided so as to simultaneously measure the characteristic values 31 of the transferred articles. That is, in the manufacturing line system 100 according to the present embodiment, the characteristic values 31 of three articles can be measured by the three measuring machines 6a to 6c at one time.

Further, channel numbers are allocated to the individual measuring machines 6a to 6c so as to identity which of the measuring machines 6a to 6c measures the characteristic value 31.

Then, the individual measuring machines 6a to 6c transmit the allocated channel number, together with the measured characteristic value 31.

The adjusting apparatus 7 estimates a device to be adjusted on the basis of the characteristic values 31 of the individual articles measured by the individual measuring machines 6a to 6c and instructs adjustment with respect to the device to be adjusted or changes a set value of the device to be adjusted.

Moreover, in the manufacturing line system 100 according to the present embodiment, the device to be adjusted is one of the processing machines 5a and 5b, one of the processing boards 3a to 3l, or one of the measuring machines 6a to 6c. Moreover, the detailed configuration of the adjusting apparatus 7 will be described below.

(Configuration of Adjusting Apparatus)

As shown in FIG. 1, the adjusting apparatus 7 according to the present embodiment has an information storing unit 12 (storage device), a receiving unit 11, a totaling unit 13, a judging unit (judging unit) 21, a histogram feature detecting unit (distribution feature calculating unit) 15, a defective fraction arithmetic unit (individual defective fraction calculating unit) 14, a cycle information detecting unit (cycle detecting unit) 16, an abnormality estimating unit (specifying unit) 17, an instruction output unit (output unit) 19, an adjusting unit (change instructing unit) 18, a state change detecting unit 20, and a setting unit (changing unit) 22.

The information storing unit 12 is a readable/writable recording medium and, for example, can be implemented by a flash EEPROM (Electrically Erasable Programmable Read Only Memory) or the like. In the information storing unit 12, the characteristic value 31 received by the receiving unit 11 and an apparatus initial value 32, which is the set value set in each of the processing machines 5a and 5b in advance, are recorded.

Moreover, the set value is a value for defining the operation of each of the processing machines 5a and 5b, and the processing result of the article is changed by changing the set value. For this reason, when the set value is changed, the characteristic value 31 of the article processed by the processing machine 5a or the processing machine 5b, the set value of which is changed, is changed.

Further, in the information storing unit 12, though not shown in FIG. 1, predetermined threshold value information, which is used for performing an estimation processing a reason for abnormality, is also recorded.

Further, in the information storing unit 12, though not shown, a warning flag, which is used when the abnormality estimating unit 17 performs the estimation processing described below of the reason for abnormality, is also recorded.

In addition, in the information storing unit 12, though not shown, information of a histogram in accordance with the characteristic value of the article processed by the processing machine 5a or the processing machine 5b before the set value is changed, information of a histogram in accordance with the characteristic value of the article processed by the processing machine 5a or the processing machine 5b after the set value is changed, and the like are recorded. The histogram information is information required for an adjustment processing of the set value described below so as to change the set value of one of the processing machine 5a and 5b.

Moreover, the above-described characteristic value 31, the apparatus initial value 32, the threshold value information, the warning flag, and the histogram information may be stored in a single information storing unit 12 or may be stored in individual recording mediums, such as memories, which are separately provided.

In addition, if the adjusting apparatus 7 according to the present embodiment can communicate with an external device through a communication network, it can be configured such that the above-described information is acquired from the external device.

The receiving unit 11 receives the measured characteristic value 31 of the articles from the individual measuring machines 6a to 6c. The receiving unit 11 causes the received characteristic values 31 to be stored in the information storing unit 12 in association with the channel numbers allocated to the individual measuring units 6a to 6c, which are the sources of the characteristic values 31, and measurement time at which the characteristic values 31 are measured by the individual measuring machines 6a to 6c.

The totaling unit 13 reads out the characteristic values 31 from the information storing unit 12 and totals the characteristic values 31 for the individual measuring machines 6a to 6c or totals the measured characteristic value 31 of all the articles. That is, the totaling unit 13 calculates the number of articles and the number of defectives on the basis of the totaling result of the characteristic values 31 for each channel number in the measuring machines 6a to 6c, and creates a histogram. Further, with respect to all the measured characteristic values 31, the totaling unit 13 calculates the number of measured articles and the number of detectives and creates a histogram.

The judging unit 21 judges, on the basis of the totaling result of all the characteristic values 31 by the totaling unit 13, whether or not to perform the estimation processing for the reason for abnormality. That is, the judging unit 21 confirms, on the basis of the characteristic value 31, presence/absence of the characteristic value 31 out of a range of characteristic values (hereinafter, referred to as regular range) in which the article meets regular quality, and judges whether or not to perform the estimation processing for the reason for abnormality. Moreover, the details of the estimation processing for the reason for abnormality will be described below.

Moreover, as for the judgment, if even one characteristic value 31 out of the regular range exists, the judging unit 21 may judge to perform the estimation processing of the reason for abnormality. Further, when it is confirmed that the characteristic value 31 out of the regular range exists at a certain ratio, the judging unit 21 may judge to perform the estimation processing of the reason for abnormality. Preferably, the judgment reference is determined according to quality acquired from the processed article.

Here, the number of measured articles is the number of articles, the characteristic values 31 of which are measured by the measuring machines 6a to 6c in a predetermined period. For example, it is assumed that 300 articles are processed in the predetermined period. In this case, the measuring machines 6a to 6c simultaneously measure the characteristic values 31 from the processed articles three by three. Therefore, the number of measured articles by each of the measuring machines 6a to 6c is 100. Further, the number of measured articles obtained from all the measuring machines 6a to 6c is 300.

Further, the number of defectives is the number of articles, the measured characteristic values of which are confirmed to be abnormal. That is, in the manufacturing line system 100, the range of the characteristic values in which the processed article meets regular quality, that is, the regular range, is determined in advance. Then, from the measured characteristic values 31, the number of articles corresponding to the characteristic values 31 out of the range becomes the number of defectives.

The histogram shows a frequency (frequency n) distribution of the characteristic value 31 of the article measured by one of the measuring machines 6a to 6c. That is, referring to FIGS. 2A and 2B, the range of the characteristic values is divided into a plurality of sections (y), and the frequency (frequency n) of the characteristic value 31 to be included in each divided section is shown.

When it is judged by the judging unit 21 that the characteristic value 31 out of the regular range exists, the histogram feature detecting unit 15 detects, on the basis of the histogram created by the totaling unit 13, a distribution feature of the corresponding histogram.

Figure 2A:
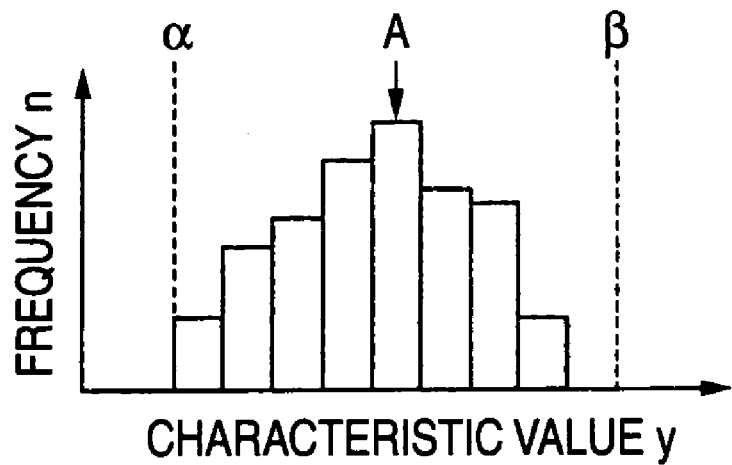
FIG. 2A shows an example of a histogram on the basis of all characteristic values which are normally processed and measured.

For example, when all the articles are normally processed by one of the processing machines 5a to 5b, and the measurement processing of the characteristic values 31 for the processed articles are normally performed, that is, in case of a normal state, as shown in FIG. 2A, all the characteristic values 31 exist in a range of α to β Moreover, the range of α to β represents the regular range, in which α is a lower limit value of the regular range and β is an upper limit value of the regular range.

Then, in the distribution of the histogram created by totaling the characteristic values 31, there occurs one section (in FIG. 2, a point A) in which the number of articles is increased, as compared with the previous or next section. That is, in general, when the processed article meets regular quality, the frequency has the maximum in the vicinity of a median of the regular range α–β. Moreover, hereinafter, in the histogram distribution, like the point A, a section in which the number of articles is increased, as compared with the previous or next section, is referred to as peak.

Figure 2B:
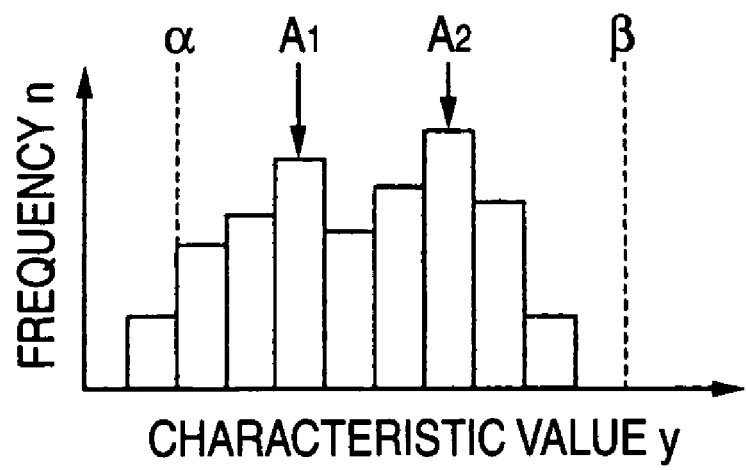
FIG. 2B shows an example of a histogram on the basis of all characteristic values which are processed and measured in an abnormal state.

On the other hand, when the article is not normally processed or when the characteristic value 31 of the processed article is not accurately measured, that is, in case of an abnormal state, the histogram distribution is as shown in FIG. 2B. That is, in case of the abnormal state, as shown in FIG. 2B, a plurality of peaks occur (peaks $A_1$ peak $A_2$) or an article having the characteristic value 31 out of the regular range α–β exists.

For example, when neither the processing machine 5a nor the processing machine 5b is normally operated, in the characteristic value 31 of the article processed by the processing machine to be not normally operated, the frequency of the section shifted from the median of the regular range α–β is the maximum. For this reason, in the histogram formed in accordance with the characteristic value 31 of the article processed by the processing machine to be normally operated and the histogram formed in accordance with the characteristic value 31 of the article processed by the processing machine to be not normally operated, the sections in which the peaks appear are not aligned with each other, but shifted from each other.

Therefore, in case of the abnormal state, as shown in FIG. 2B, two peaks appear in the histogram.

As such, the created histogram has a characteristic distribution in accordance with the characteristic value 31 of the article in the normal state or the characteristic value 31 of the article in the abnormal state.

Here, the histogram feature detecting unit 15 analyzes the number of peaks on the basis of the histogram created by the totaling unit 13 in accordance with the instruction from the judging unit 21. Then, the histogram feature detecting unit 15 transmits the analyzed number of peaks to the abnormality estimating unit 17.

When it is judged by the judging unit 21 that the characteristic value 31 out of the regular range exists, the defective fraction arithmetic unit 14 calculates a defective fraction of the measured characteristic value 31. That is, the defective fraction arithmetic unit 14 calculates the defective fraction of each of the characteristic values 31 measured by the individual measuring machines 6a to 6c and the defective fraction for all the measured characteristic values 31.

Moreover, the defective fraction arithmetic unit 14 can perform an arithmetic operation represented by the following equation (1) with respect to all the characteristic values 31 and the characteristic values 31 of each measuring machine so as calculate the defective fraction.

$$NGRation = (N\_i - OK\_Num\_i)/N\_i \qquad (1)$$

NGRation: the defective fraction

OK_Num_i: the number of characteristic values 31 within the regular range in the measurement result by the measuring machine having the channel number i or the number of characteristic values 31 within an expected range in the measurement result by all the measuring machines N_i: the number of characteristic values 31 measured by the measuring machine having the channel number i or the number of characteristic values 31 measured by all the measuring machines Then, the defective fraction arithmetic unit 14 transmits the defective fraction obtained by performing the arithmetic operation according to the above-described equation (1) to the abnormality estimating unit 17.

The cycle information detecting unit 16 examines the relationship between a sequence number of the processed and measured articles, and the characteristic values 31 of the articles. More specifically, the cycle information detecting unit 16 detects cyclicity in the relationship between the sequence number of the processed and measured articles, and the characteristic values 31 of the articles by performing an arithmetic operation according to an equation described below.

In the manufacturing line system 100 according to the present embodiment, the articles inputted from the article inlet 1 are constantly transferred in sequence. Further, the three measuring machines 6a to 6c are configured to measure the articles according to an input sequence number in an order of the measuring machine 6a, the measuring machine 6b, and the measuring machine 6c.

Further, as described above, in the information storing unit 12, the channel number allocated to each of the measuring machines 6a to 6c and the measurement date of the characteristic value 31 are recorded in association with the measured characteristic value 31.

Therefore, the sequence number of the characteristic values 31 of the processed articles can be grasped with reference to the date and the channel number of each of the measuring machines 6a to 6c. Moreover, the channel number 1, the channel number 2, and the channel number 3 are allocated to the measuring machine 6a, the measuring machine 6b, and the measuring machine 6c, respectively.

That is, in the manufacturing line system 100 according to the present embodiment, as for the sequence number of the articles to be transferred, the processing machines 5a and 5b which process the articles, the processing boards 3a to 3l which fix the articles for processing, and the measuring machines 6a to 6c which measure the characteristic values of the processed articles, the following relationship is established.

Articles which are processed and the characteristic values of which are measured: $OB_1, OB_2, OB_3, \ldots$ Processing machine 5a, Processing machine 5b: $W_1, W_2$ Processing boards 3a to 3l: $P_1, P_2, P_3, \ldots, P_{12}$ Measuring machines 6a to 6c: $M_1, M_2, M_3$ The sequence number of the articles $OB_1, OB_2, OB_3, \ldots$ to be processed by the processing machines $W_1$ and $W_2$ is as follows.

$W_1$: $OB_1, OB_{(x+1)}, OB_{(2x+1)}, \ldots$
$W_2$: $OB_2, OB_{(x+2)}, OB_{(2x+2)}, \ldots$ Further, the sequence number of the articles $OB_1, OB_2, OB_3, \ldots$, the characteristic values of which are measured by the measuring machines $M_1, M_2$, and $M_3$, is as follows.

$M_1$: $OB_1, OB_{(y+1)}, OB_{(2y+1)}, \ldots$
$M_2$: $OB_2, OB_{(y+2)}, OB_{(2y+2)}, \ldots$
$M_3$: $OB_3, OB_{(y+3)}, OB_{(2y+3)}, \ldots$ Similarly, the sequence number of the articles $OB_1, OB_2, OB_3, \ldots$ to be fixed by the processing boards 3a to 3l is as follows.

$P_1$: $OB_1, OB_{(z+1)}, OB_{(2z+1)}, \ldots$
$P_2$: $OB_2, OB_{(z+2)}, OB_{(2z+2)}, \ldots$
$P_3$: $OB_3, OB_{(z+3)}, OB_{(2z+3)}, \ldots$
$\ldots$
$P_{12}$: $OB_{12}, OB_{(z+12)}, OB_{(2z+12)}, \ldots$ Then, with the predetermined number of measured articles, when a horizontal axis represents a transfer sequence number of the processed and measured articles, and a vertical axis represents the value of a natural number obtained by normalizing the characteristic values 31 of the individual articles corresponding to the second number, the measured characteristic values 31 are dotted as shown FIG. 3A to 3D.

Moreover, FIGS. 3A to 3D are diagrams showing the relationship between the transfer sequence number of the articles which are processed and the characteristic values of which are measured, and the characteristic values 31 of the individual articles.

FIG. 3A shows the relationship between the transfer sequence number of the articles which are processed and the characteristic values of which are measured, and the characteristic values 31 of the individual articles in the normal state.

Further, FIG. 3B shows the relationship between the transfer sequence number of the articles which are processed and the characteristic values of which are measured, and the characteristic values 31 of the individual articles when any one of the processing machines 5a and 5b is not normally operated.

Figure 3C:
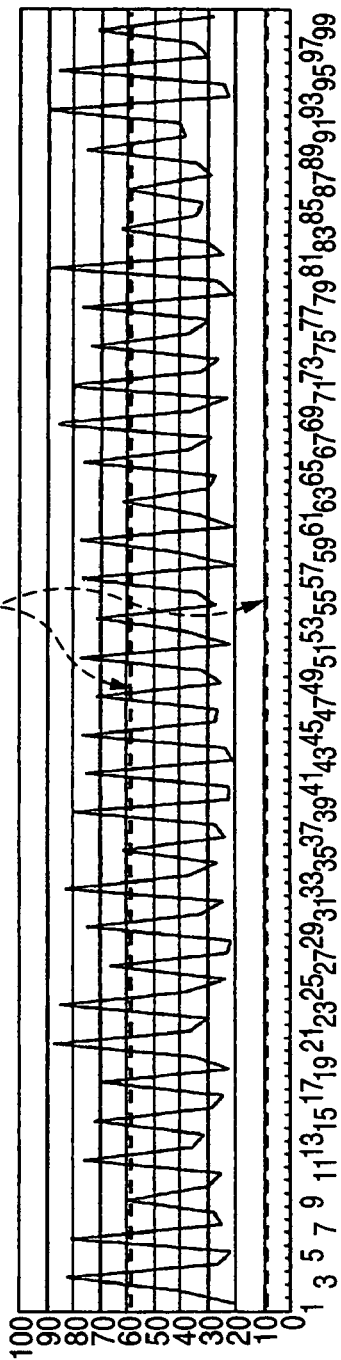

Further, FIG. 3C shows the relationship between the transfer sequence number of the articles which are processed and the characteristic values of which are measured, and the characteristic values 31 of the individual articles when any one of the measuring machines 6a to 6c is not normally operated.

Figure 3D:
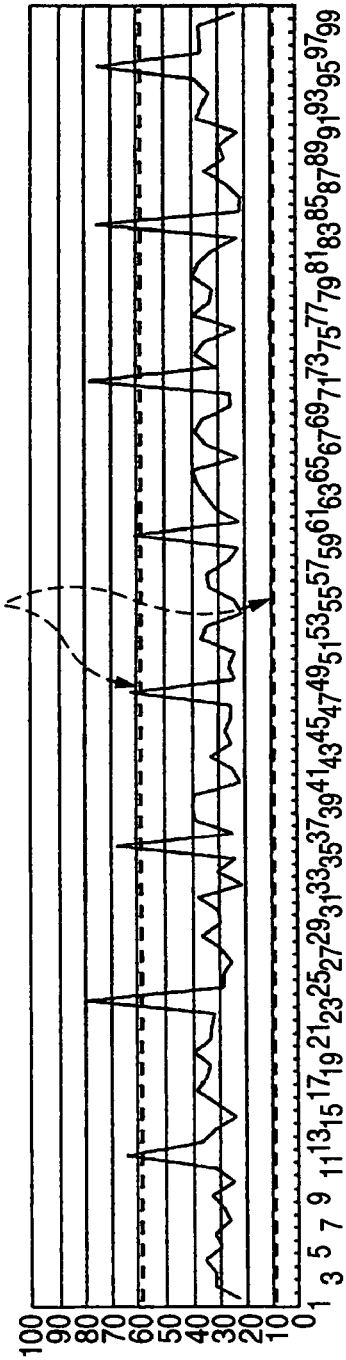

Further, FIG. 3D shows the relationship between the transfer sequence number of the articles which are processed and the characteristic values of which are measured, and the characteristic values 31 of the individual articles when any one of the processing boards 3a and 3l is not normally operated.

For example, when all the 100 articles are normally processed, and the characteristic values 31 thereof are normally measured, as shown in FIG. 3A, the values of 1 to 100 indicating the characteristic values 31 constantly fall within the regular range. In this case, as for the relationship between the sequence number of the processed articles and the characteristic values 31 of the articles, no cyclicity is particularly observed.

On the other hand, when any one of the processing machines 5a and 5b is not normally operated, as shown in FIG. 3B, the measured characteristic values 31 are out of the regular range for every one. That is, as for the predetermined number of measured articles, the characteristic values 31 out of the regular range are generated by the two cycles.

Further, when any one of the measuring machines 6a to 6c is not normally operated, as shown in FIG. 3C, the measured characteristic values 31 are out of the regular range for every two. That is, as for the predetermined number of measured articles, the characteristic values 31 out of the regular range are generated by the three cycles.

Further, when any one of the processing boards 3a to 3l is not normally operated, as shown in FIG. 3D, the measured characteristic values 31 are out of the regular range for every eleven. That is, as for the predetermined number of measured articles, the characteristic values 31 out of the regular range are generated by the twelve cycles.

As such, when any one of the processing machines 5a and 5b, any one of the measuring machines 6a to 6c, or any one of the processing boards 3a to 1l is not normally operated, from the relationship between the sequence number of the processed and measured articles and the characteristic values 31 of the individual articles, constant cyclicity appears.

Moreover, in FIGS. 3A to 3D, the measured characteristic values 31 are out of the regular range for every one, two, or eleven, but, cyclicity in which the characteristic values 31 out of the regular range are generated is not limited thereto.

That is, cyclicity is determined by the number of processing machines, processing boards, or measuring machines included in the above-described manufacturing line system 100. Then, the number of processing machines, processing boards, or measuring machines is changed, cyclicity is also changed.

As such, cyclicity is made different according to the number of devices, such as the number of processing machines 5a and 5b included in the manufacturing line system 100 according to the present embodiment or the number of devices to be adjusted.

Here, the detection method of cyclicity by the cycle information detecting unit 16 will be described.

Specifically, by performing arithmetic operations according to the following equations (2) to (4), the cycle information detecting unit 16 can detect which cyclicity is recognized with respect to the relationship between the sequence number of the processed and measured articles and the characteristic values 31 of the individual articles.

That is, when the number of measured articles is 100, and when it is examined whether or not the measured characteristic values are out of the regular range for every one (by the two cycles), the arithmetic operation according to the following equation (2).

$$\Sigma((x(t)-x(t-1))^2) \quad (2)$$

x(t): the characteristic value of the t-th article x(t−1): the characteristic value of the (t−1)th article Moreover, t: $1 \leq t \leq 100$ Further, when the number of measured articles is 100, and when it is examined whether or not the measured characteristic values are out of the regular range for every two (by the three cycles), the arithmetic operation according to the following equation (3).

$$\Sigma((x(t)-x(t-2))^2) \quad (3)$$

x(t−2): the characteristic value of the (t−2)th article

Further, when the number of measured articles is 100, and when it is examined whether or not the measured characteristic values are out of the regular range for every eleven (by the twelve cycles), the arithmetic operation according to the following equation (4).

$$\Sigma((x(t)-x(t-11))^2) \quad (4)$$

x(t−11): the characteristic value of the (t−11)th article

Here, as the results of the arithmetic operations according to the equations (2) to (4), the results of the case in which all the characteristic values 31 of the measured articles are normal, the case in which the characteristic values 31 are out of the regular range for every one, and the case in which the characteristic values 31 are out of the regular range for every two, and the case in which the characteristic values 31 are out of the regular range for every eleven are shown in FIG. 4.

As shown in FIG. 4, as compared the case in which the arithmetic operation according to the equation (2) is performed on the characteristic values in the normal state and the case in which the arithmetic operation according to the equation (2) is performed on the characteristic values which are out of the regular range for every one, it can be understood that the latter has the value larger than the former.

Then, the adjusting apparatus 7 according to the present embodiment can judge whether or not the result of the arithmetic operation of the equation (2) by the cycle information detecting unit 16, so as to examine whether or not cyclicity in which the characteristic values 31 are out of the regular range for every one appears.

Further, as compared the case in which the arithmetic operation according to the equation (3) is performed on the characteristic values in the normal state and the case in which the arithmetic operation according to the equation (3) is performed on the characteristic values which are out of the regular range for every two, it can be understood that the latter has the value larger than the former.

Then, the adjusting apparatus 7 according to the present embodiment can judge whether or not the result of the arithmetic operation of the equation (3) by the cycle information detecting unit 16 is equal to or larger than a predetermined threshold value, so as to examine whether or not cyclicity in which the characteristic values 31 are out of the regular range for every two appears.

Further, as compared the case in which the arithmetic operation according to the equation (4) is performed on the characteristic values in the normal state and the case in which the arithmetic operation according to the equation (4) is performed on the characteristic values which are out of the regular range for every eleven, it can be understood that the latter has the value larger than the former.

Then, the adjusting apparatus 7 according to the present embodiment can judge whether or not the result of the arithmetic operation of the equation (4) by the cycle information detecting unit 16, so as to examine whether or not cyclicity in which the characteristic values 31 are out of the regular range for every eleven appears.

Then, the cycle information detecting unit 16 transmits the results of the arithmetic operations of the equations (2) to (4) on the measuring characteristic values 31 to the abnormality estimating unit 17.

In the manufacturing line system 100 according to the present embodiment, for example, if the articles are continuously inputted from the article inlet 1, the articles may be missed. However, in such a case, since the cycle information detecting unit 16 is configured to perform the equations (2) to (4) for a predetermined relatively large number of characteristic values 31, as for the characteristic values 31 to be subjected to the arithmetic operation, cyclicity are mainly maintained.

Therefore, even when missing occurs in the sequence number of the processed articles in such a manner, through the arithmetic operations by the cycle information detecting unit 16, the values which approximate to the values shown in FIG. 4 can be obtained.

The abnormality estimating unit 17 estimates a reason for abnormality on the basis of following information. The information is a defective fraction for all the measured characteristic values 31 received from the defective fraction arithmetic unit 14 and a defective fraction in each of the characteristic values 31 measured by the individual measuring machines 6a to 6c. Further, the information is information indicating the histogram received from the histogram feature detecting unit 16. In addition, the information is information indicating cyclicity received from the cycle information detecting unit 16.

Then, the abnormality estimating unit 17 transmits information indicating an instruction for an operator to the instruction output unit 19 or information indicating an adjustment instruction for the adjusting apparatus 7 according to the estimated reason for abnormality.

The instruction output unit 19 operates the manufacturing line system 100 according to the present embodiment so as to output the adjustment instruction of the processing boards or the measuring machines 6a to 6c to the operator. The adjusting apparatus 7 according to the present embodiment has a display device (not shown), and the instruction output unit 19 transmits adjustment instruction information received from the abnormality estimating unit 17 to the display device and instructs the display device to display the adjustment instruction information.

As such, by causing the display device to display the adjustment instruction, a member to be adjusted can be can be instructed to the operator. Moreover, the information of the adjustment instruction to the operator is not limited thereto. For example, when each operator may have a portable terminal device, and the portable terminal device is communicatably connected to the adjusting apparatus 7, the adjustment instruction may be transmitted from the instruction output unit 19 to the portable terminal device. Further, when the adjusting apparatus 7 according to the present embodiment has a print device, the adjustment instruction may be outputted to the print device and then is printed onto a paper so as to notify the operator of the adjustment instruction.

If the abnormality estimating unit 17 is estimated that any one of the processing machines 5a and 5b has the reason for abnormality, the adjusting unit 18 adjusts the set value of the processing machine having the reason for abnormality. The adjusting unit 18 instructs the setting unit 22 to change the set value of the processing machine having the reason for abnormality.

Moreover, the adjustment processing of the set value of any one of the processing machines 5a and 5b by the adjusting unit 18 will be described below.

The setting unit 22 changes the set value of the processing machine 5a or the processing machine 5b according to the instruction from the adjusting unit 18.

The state change detecting unit 20 receives the instruction from the adjusting unit 18 and instructs the totaling unit 13 to total the characteristic values 31 or the articles processed after the set value of any one of the processing machines 5a and 5b is changed. Further, the state change detecting unit 20 instructs the abnormality estimating unit 17 to stop the estimation processing of the reason for abnormality.

Figure 5:
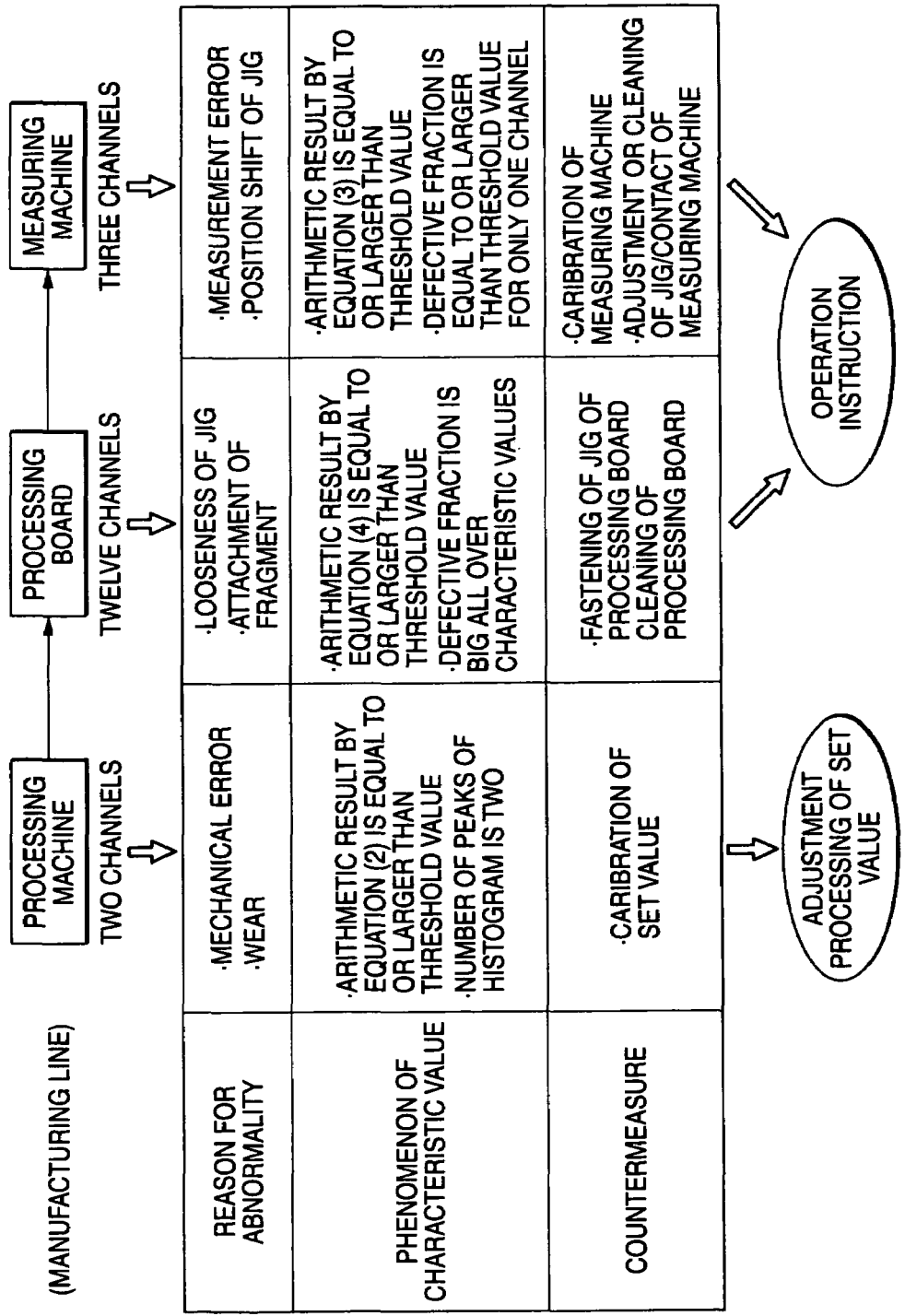
FIG. 5 is a diagram illustrating an example of reasons for abnormality in the processing machines, the processing boards, and the measuring machines, the phenomenon obtained from the characteristic values, and countermeasures against abnormal states.

Here, in the manufacturing line system 100 according to the present embodiment, the reasons for abnormality of the characteristic values 31 measured from the processed articles will be described with reference to FIG. 5. Moreover, FIG. 5 is a diagram showing the reasons for abnormality of the individual measuring machines 6a to 6c, phenomena introduced by the characteristic values when the reasons for abnormality are generated, and countermeasures against the reasons for abnormality.

As described above, the manufacturing line system 100 according to the present embodiment has the processing machines 5a and 5b, the processing boards 3a to 3l, and the measuring machines 6a to 6c. For this reason, when any one of the individual members is not normally operated, the measured characteristic value 31 becomes abnormal.

As the reason when the processing machine 5a or the processing machine 5b is not normally operated, a mechanical error of the processing machine 5a or the processing machine, and wear caused by the processing of the processing machine 5a or the processing machine 5b can be exemplified.

Further, as the reason when any one of the processing boards 3a to 3l is not normally operated, looseness of a jig serving as a member used for installing the articles in the processing boards 3a to 3l, fragment attachment to an installment place of the article, and the like can be exemplified.

Further, as the reason when any one of the measuring machines 6a to 6c is not normally operated, a measurement error of any one of the measuring machines 6a to 6c, and a position shift of a jig used for fixing the article when the corresponding measuring machine measures the characteristic value 31 can be exemplified.

Therefore, when the article is processed in a state in which any one of the processing machines 5a and 5b, any one of the processing boards 3a to 3l, or any one of the measuring machines 6a to 6c is not normally operated, the following phenomena in the characteristic values 31 measured from the processed articles are observed.

That is, when any one of the two processing machines 5a and 5b is not normally operated, as for the relationship between the sequence number of the processed and measured articles and the characteristic values 31 of the individual articles, the characteristic values 31 become abnormal for every one. That is, the value to be obtained by the arithmetic operation of the equation (2) is made larger than a predetermined threshold value.

Further, as the feature of the characteristic value 31 when any one of the two processing machines 5a and 5b is not normally operated, in the histogram created by the totaling unit 13 in accordance with all the characteristic values 31, two peaks appear, as shown in FIG. 2B.

For this reason, when the two peaks appear in the histogram, if the result of the arithmetic operation by the equation (2) of the cycle information detecting unit 16 is made larger than the predetermined threshold value, it can be judged that any one of the processing machines 5a and 5b is not normally operated.

Further, when any one of the processing boards 3a to 3l is not normally operated, the defective fraction for all the characteristic values 31 of the measured articles becomes a predetermined threshold value.

Further, when any one of the processing boards 3a to 3l is not normally operated, the characteristic values 31 become abnormal for every eleven. That is, the value to be obtained by the result of the arithmetic operation of the equation (4) is made larger than the predetermined threshold value.

Further, when any one of the measuring machines 6a to 6c is not normally operated, the characteristic values 31 acquired from any of the measuring machines 6a to 6c include a large number of abnormal characteristic values, as compared with other measuring machines. That is, as shown in FIG. 7, the defective fraction of the characteristic values 31 measured by the measuring machine having a specified channel number from the measuring machines 6a to 6c is made larger than the defective fraction of the characteristic values 31 measured by the measuring machines having other channel number from the measuring machines 6a to 6c.

Figure 7:
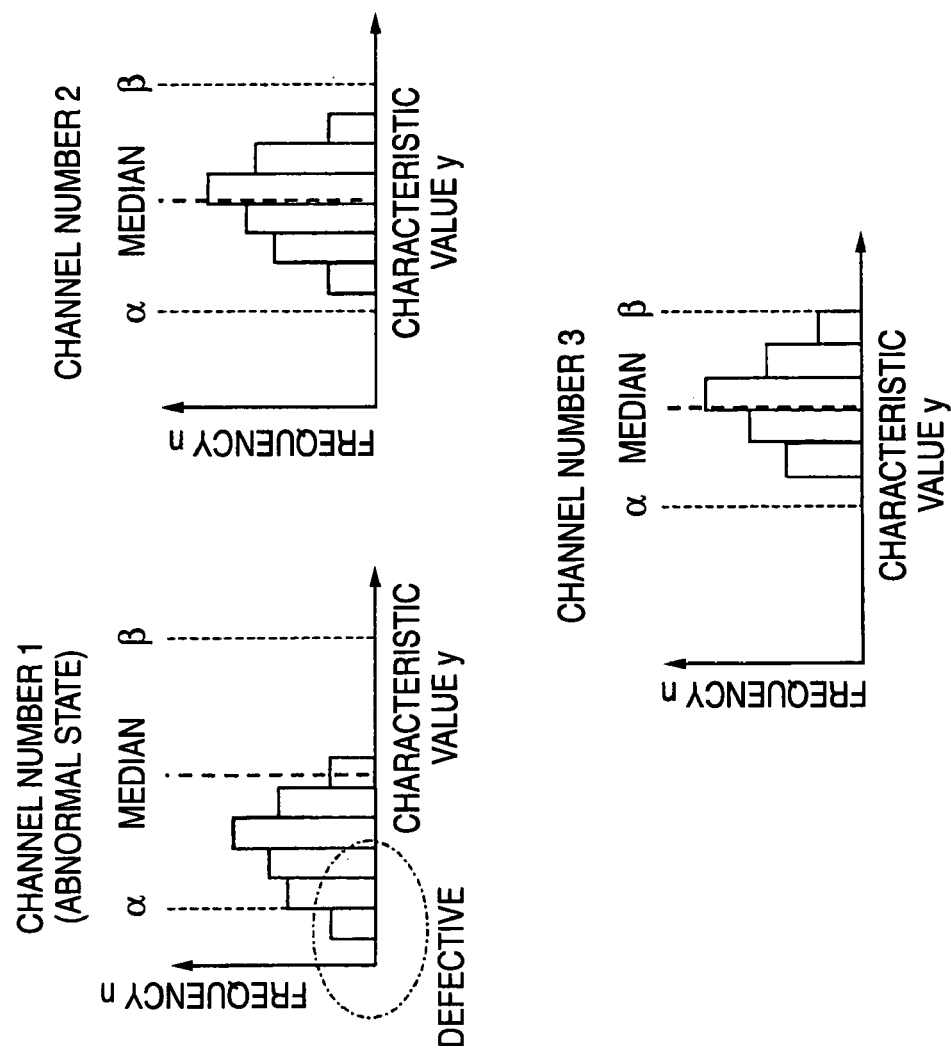
FIG. 7 is a diagram showing histograms on the basis of the individual characteristic values measured by the individual measuring machines when any one of three measuring machines is in an abnormal state.

Moreover, FIG. 7 is a diagram showing the histogram according to the characteristic values 31 measured by each of the measuring machines 6a to 6c. As shown in FIG. 7, when abnormality is generated in the measuring machine 6a having the channel number 1, the distribution of the characteristic values 31 measured by the measuring machine 6a appears in a range other than the regular range α–β. Further, the peak appears at a position significantly shifted from the median of the regular range.

Further, when any one of the measuring machines 6a to 6c is not normally functioned, as for the relationship between the sequence number of the measured articles and the characteristic values 31 of the individual articles, the characteristic values 31 become abnormal for every two. That is, the value to be obtained by the result of the arithmetic operation of the equation (3) is made larger than a predetermined threshold value.

When any one of the twelve processing boards is abnormal, the defective fraction of the characteristic values 31 measured by the measuring machine having the specified channel number from the measuring machines 6a to 6c may be made larger than the defective fraction of the characteristic values 31 measured by the measuring machines having other channel numbers from the measuring machines 6a to 6c.

In this case, however, a probability that abnormality is confirmed in the characteristic values 31 measured by the measuring machine having the specified channel number from the measuring machines 6a to 6c is substantially 25 percent.

Then, the configuration, which further includes the following conditions, may be provided such that the case in which any one of the twelve processing boards 3a to 3l is abnormal can be distinguished from the case in which abnormality is generated in any one of the measuring machines 6a to 6c. That is, the defective fraction of the characteristic values 31 measured by the measuring machine having the specified channel number from the measuring machines 6a to 6c is made larger than the defective fraction of the characteristic values 31 measured by the measuring machines having other channel numbers from the measuring machines 6a to 6c, and the defective fraction is a predetermined threshold value (the value larger than 25 percent).

Moreover, the predetermined threshold value with respect to the values to be obtained by the results of the arithmetic operations of the individual equation (2) and (4) may be provided individually for each arithmetic operation or may be provided in common.

For example, when the common value is provided as the predetermined threshold value with respect to the values to be obtained by the results of the arithmetic operations of the individual equations (2) to (4), the predetermined threshold value is larger than the results of the arithmetic operations of the individual equations (2) to (4) which are performed on the characteristic values in the normal state. The common value is suitably set with respect to the relationship among candidates to be adjusted, that is, the relationship among the processing machines 5a and 5b, the processing boards 3a to 3l, and the measuring machines 6a and 6c.

Further, when the predetermined threshold values with respect to the values to be obtained by the results of the arithmetic operations of the equations (2) to (4) are individually provided, the threshold values are determined as follows.

That is, the predetermined threshold value with respect to the value to be obtained by the result of the arithmetic operation of the equation (2) can be set from the result obtained by performing the arithmetic operation of the equation (2) when the normal state, when the characteristic values 31 of the articles are abnormal for every one, when the characteristic values 31 of the articles are abnormal for every two, and when the characteristic values 31 of the articles are abnormal for every eleven. Moreover, as described above, the result of the arithmetic operation is as shown in FIG. 4, for example. For this reason, with reference to the result of the arithmetic operation shown in FIG. 4, the threshold value is set to the value equal to or less than '214833' which is larger than '160733' and is a range to be obtained as the result of the arithmetic operation when the characteristic values 31 becomes abnormal for every one.

Further, the predetermined threshold value with respect to the value to be obtained by the result of the arithmetic operation of the equation (3) can be set from the result obtained by performing the arithmetic operation of the equation (3) when the normal state, when the characteristic values 31 of the articles are abnormal for every one, when the characteristic values 31 of the articles are abnormal for every two, and when the characteristic values 31 of the articles are abnormal for every eleven. Moreover, as described above, the result of the arithmetic operation is as shown in FIG. 4, for example. For this reason, with reference to the result of the arithmetic operation shown in FIG. 4, the threshold value is set to the value equal to or less than '165419' which is a range to be obtained as the result of the arithmetic operation when the characteristic values 31 becomes abnormal for every two.

Further, the predetermined threshold value with respect to the value to be obtained by the result of the arithmetic operation of the equation (4) can be set from the result obtained by performing the arithmetic operation of the equation (4) when the normal state, when the characteristic values 31 of the articles are abnormal for every one, when the characteristic values 31 of the articles are abnormal for every two, and when the characteristic values 31 of the articles are abnormal for every eleven. Moreover, as described above, the result of the arithmetic operation is as shown in FIG. 4, for example. For this reason, with reference to the result of the arithmetic operation shown in FIG. 4, the threshold value is set to the value equal to or less than '37789' which is larger than '8467' and is a range to be obtained as the result of the arithmetic operation when the characteristic values 31 becomes abnormal for every eleven.

Further, the predetermined threshold value 31 with respect to the defective fraction for all the characteristic values is set, for example, as described below. That is, among the candidates to be adjusted, the processing boards 3a to 3l have the minimum defective fraction. Therefore, as the threshold value of the defective fraction, when the characteristic values 31 of the 100 articles are measured, and when any one of the processing boards 3a to 3l is not normally operated, abnormality is confirmed in the measured characteristic values 31 at a ratio of one per twelve times. For this reason, the defective fraction becomes about 8 percent. Then, the threshold value of the defective fraction is set to 8 percent.

Further, actually, since the measurement error of the measuring machine or the variation in the measured characteristic values is generated, the predetermined threshold value is preferably set to have a slight width as a range of possible threshold values in consideration of the measurement error or the variation in the measured characteristic values.

Moreover, in the adjusting apparatus 7 according to the present embodiment, the information on the threshold values is stored in the information storing unit 12 as threshold value information (not shown) in advance.

When the member to be adjusted is specified by use of the abnormality detection condition, in the manufacturing line system 100 according to the present embodiment, the following countermeasures are performed.

For example, when abnormality is confirmed in any one of the processing machines 5a and 5b, the set value of any one of the processing machines 5a and 5b is changed.

On the other hand, when abnormality is confirmed in any one of the processing boards 3a to 3l or the measuring machines 6a to 6c, the operator is instructed to fasten the jigs of the processing boards 3a to 3l or clean the processing boards 3a to 3l or the operator is instructed to adjust the measuring machines 6a to 6c, adjust contacts of jigs of the measuring machines 6a to 6c, and clean the jigs.

Figure 6:
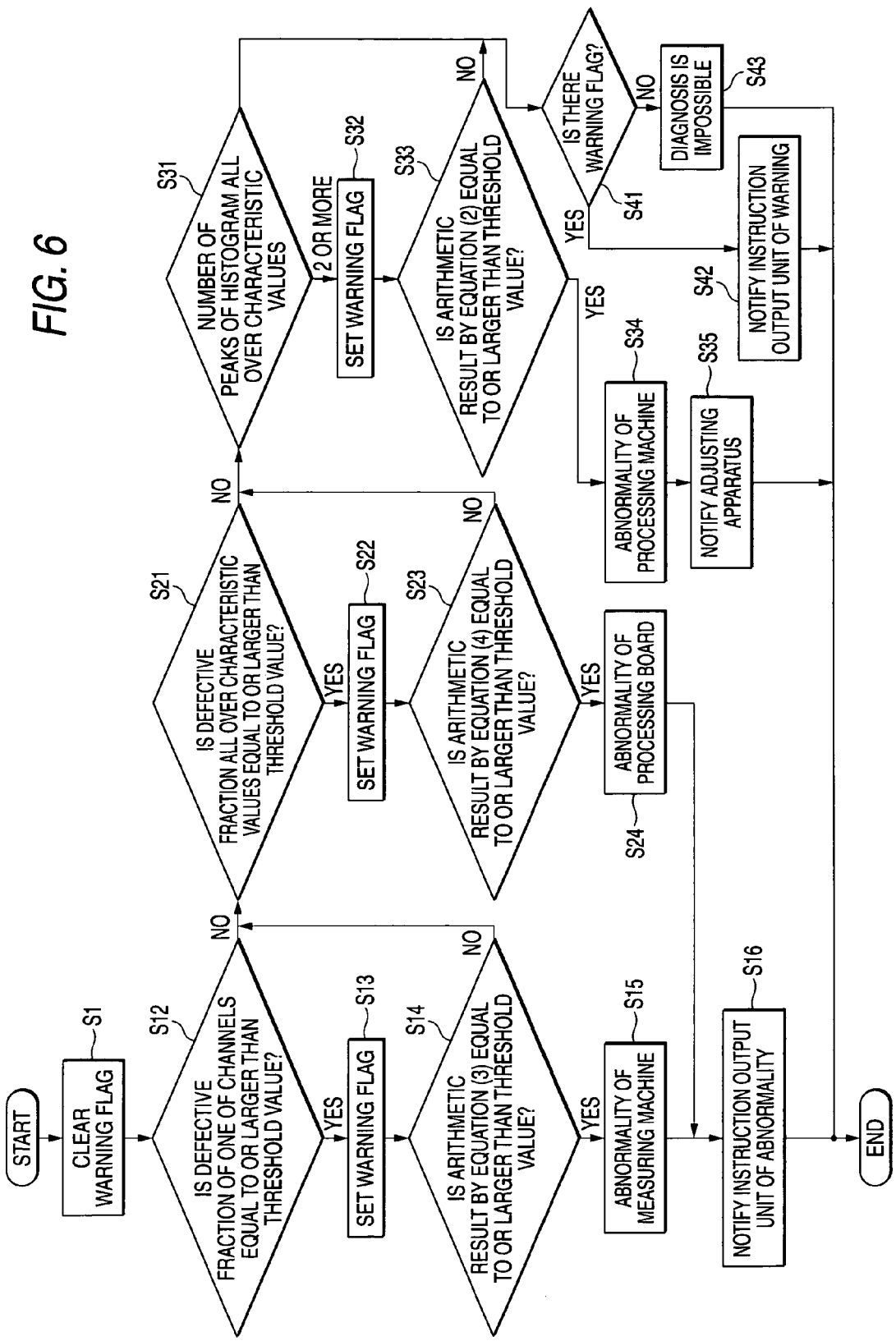
FIG. 6 is a flowchart showing an example of an estimation processing of the reason for abnormality in an adjusting apparatus according to the present embodiment.

Next, how the reason for abnormality is estimated by use of the above-described abnormality detection conditions will be described below with reference to FIG. 6.

(Estimation Processing of Reason for Abnormality)

Next, when it is judged by the judging unit 21 that the characteristic value 31 out of the regular range exists, the estimation processing of the reason for abnormality to be performed by the adjusting apparatus 7 according to the present embodiment will be described.

Here, it is assumed that the defective fraction of all the measured characteristic values is 5 percent, the defective fractions of the characteristic values 31 measured by the individual measuring machines 6a to 6c are 10 percent, respectively, and the threshold value to be set with respect to the results of the arithmetic operations of the equations (2) to (4) is 10000. Moreover, the threshold values are stored in the information storing unit 12 (not shown) in advance.

Further, the histogram distribution feature (the number of peaks) is received from the histogram feature detecting unit 15, the defective fractions of the characteristic values 31 measured by the individual measuring machines 6a to 6c and the defective fraction of all the characteristic values are received from the defective fraction arithmetic unit 14, and the information of cyclicity is received from the cycle information detecting unit 16.

First, the abnormality estimating unit 17 clears setting of the warning flag before the estimation processing of the reason for abnormality is performed (Step S11) (hereinafter, referred to as S11). Moreover, the warning flag is a flag which is used to indicate which estimation processing is performed and is stored in the information storing unit 12 (not shown) in advance.

Further, the warning flag is provided for judgment whether or not any one of the processing boards 3a to 3l is abnormal, whether or not any one of the processing machines 5a and 5b is abnormal, or whether or not any one of the measuring machines 6a to 6c.

Accordingly, when the estimation processing of the reason for abnormality is not performed yet, the warning flag must be not set in the information storing unit 12. For this reason, before the estimation processing of the reason for abnormality is performed, the abnormality estimating unit 17 clears setting of the warning flag. Specifically, the abnormality estimating unit 17 sets the flag to '0' when '1' is set as the warning flag recorded in the information storing unit 12.

Next, the abnormality estimating unit 17 compares the defective fractions of the characteristic values 31 of the individual measuring machines 6a to 6c from the defective fractions received from the defective fraction arithmetic unit 14. Then, the abnormality estimating unit 17 judges whether or not there is a defective fraction equal to or larger than the predetermined threshold value (defective fraction 5 percent) from the defective fractions of the characteristic values 31 correlated with the channel numbers of the individual measuring machines 6a to 6c (S12).

Here, as the judgment result, when only one of the defective fractions is equal to or larger than the predetermined threshold value ('YES' in S12), the abnormality estimating unit 17 sets the warning flag (S13). That is, the abnormality estimating 17 sets 1 in the information storing unit 12 as the warning flag according to the judgment whether or not any one of the measuring machines 6a to 6c is abnormal.

On the other hand, in case of 'NO' in the step S12, it is judged whether or not the defective fraction for all the measured characteristic values 31 is equal to or larger than a predetermined threshold value (8 percent) (S21).

If setting of the warning flag is completed, the abnormality estimating unit 17 judges whether or not the result of the arithmetic operation is equal to or larger than a predetermined threshold value (1000) on the basis of the result of the arithmetic operation of the equation (3) by the cycle information detecting unit 16 (S14). Here, when any one of the measuring machines 6a to 6c is abnormal, as shown in FIG. 4, the result of the arithmetic operation of the equation (3) becomes '165419'. For this reason, the result of the arithmetic operation is equal to or larger than the threshold value '10000' set in advance.

Therefore, as the judgment result, when it is judged that the result of the arithmetic operation is equal to or larger than the predetermined threshold value ('YES' in S14), the abnormality estimating unit 17 estimates that any one of the measuring machines 6a to 6c is in the abnormal state.

On the other hand, in case of 'NO' in the judgment of the step S14, it is judged whether or not the defective fraction of all the measured characteristic values 31 is equal to or larger than the predetermined threshold value (8 percent) (S21).

Here, when any one of the measuring machines 6a to 6c is in the abnormal state, in the step S15, in order to notify a purport that any one of the measuring machines 6a to 6c is in the abnormal state, the abnormality estimating unit 17 outputs information indicating the notification to the instruction output unit 19.

In such a manner, when any one of the measuring machines 6a to 6c is in the abnormal state, the abnormality estimating unit 17 can specify the measuring machine to be adjusted and notify the operator of the measuring machine to be adjusted.

Next, in case of 'NO' in the step S12 or in case of 'NO' in the step S14, the abnormality estimating unit 17 judges whether or not the defective fraction for all the measured characteristic values 31 is the predetermined threshold value (S21). Moreover, when any one of the processing boards 3a to 3l is in the abnormal state, the defective fraction for all the characteristic values becomes 8.3 percent or more, and thus is equal to or larger than the predetermined threshold value (8 percent).

As the judgment result, when the defective fraction for all the characteristic values 31 is equal to or larger than the predetermined threshold value (10000) ('YES' in S21), the abnormality estimating unit 17 sets the warning flag (S22). That is, the abnormality estimating unit 17 sets '1' in the information storing unit as the warning flag according to the judgment processing of whether or not any one of the processing machines 3a to 3l is in the abnormal state.

On the other hand, in case of 'NO' in the step S21, it is judged whether or not two peaks or more appear in the histogram for all the characteristic values 31 (S31).

When the warning flag is set in the step S22, the abnormality estimating unit 17 judges whether or not the result of the arithmetic operation of the equation (4) is equal to or larger than a threshold value (S23). As the judgment result, it is judged that the result of the arithmetic operation of the equation (4) is equal to or larger than the threshold value ('YES' in S23), the abnormality estimating unit 17 estimates that any one of the processing boards 3a to 3l is in the abnormal state (S24). That is, when any one of the processing boards 3a to 3l is in the abnormal state, as shown in FIG. 4, the result of the arithmetic result of the equation (4) becomes '37789', and thus is equal to or larger than the threshold value (10000).

Therefore, in case of 'YES' in the step S23, the abnormality estimating unit 17 can estimate that any one of the processing boards 3a to 3l is abnormal. In this case, in order to notify the operator of a purport that any one of the processing boards 3a to 3l is in the abnormal state, the abnormality estimating unit 17 outputs information indicating the notification of the purport of the abnormal state.

On the other hand, in case of 'NO' in the step S23, the abnormality estimating unit 17 performs a processing shown in the step S31, that is, judges whether or not two peaks or more exist in the histogram for all the measured characteristic values 31.

In such a manner, when any one of the processing boards 3a to 3l is in the abnormal state, the abnormality estimating unit 17 can specify the processing board as the device to be adjusted and notify the operator of the specified processing board.

Next, in case of 'NO' in the step S21 or in case of 'NO' in the step S23, the abnormality estimating unit 17 judges whether the number of peaks of the histogram created on the basis of all the measured characteristic values 31 is two or more, or one (S31).

As the judgment result of the step S31, when the abnormality estimating unit 17 judges that the number of peaks of the histogram is two or more ('YES' in the step S31), the warning flag is set. That is, the abnormality estimating unit 17 sets '1' in the information storing unit as the warning flag according to the judgment result of whether or not any one of the processing machines 5a and 5b is in the abnormal state.

On the other hand, in the step 531, it is judged that the number of peaks of the histogram is one, the abnormality estimating unit 17 confirms presence/absence of the warning flag recorded in the information storing unit 12 (S41).

When the warning flag is set in the step S32, the abnormality estimating unit 17 judges whether or not the result of the arithmetic operation of the equation (2) is equal to or larger than the threshold value (10000) (S33). Then, in case in which the judgment result in the step S33 is 'YES', the abnormality estimating unit 17 estimates that any one of the processing machines 5a and 5b is in the abnormal state (S34). That is, when any one of the processing machines 5a and 5b is in the abnormal state, as shown in FIG. 4, the result of the arithmetic operation of the equation (2) becomes '37789', and thus is equal to or larger than the threshold value '10000'.

On the other hand, in case of 'NO' in the step S33, the process progresses to the step S41. That is, the abnormality estimating unit 17 performs a processing for judging presence/absence of the warning flag.

Therefore, in case of 'YES' in the step S33, the abnormality estimating unit 17 can estimate that any one of the processing machines 5a and 5b is abnormal. In this case, the abnormality estimating unit 17 notifies the adjusting unit 18 of a purport that any one of the processing machines 5a and 5b is in the abnormal state. Moreover, the abnormality estimating unit 17 transmits the information of the histogram on the basis of all the measured characteristic values 31 to the adjusting unit, together with the notification.

In such a manner, when any one of the processing machines 5a and 5b is in the abnormal state, the abnormality estimating unit 17 can specify any one of the processing machines 5a and 5b as the device to be adjusted and notify the adjusting unit 18 of the specified processing machine.

In the step S31, when it is judged that the number of peaks of the histogram is one, or when it is judged that the result of the arithmetic operation of the equation (2) in the step S33 is less then the threshold value, the abnormality estimating unit 17 judges whether or not the warning flag is set (S41). That is, according to whether or not the warning flag is set, the abnormality estimating unit 17 can understand whether or not to perform the estimation processing for abnormality of any one of the measuring machines 6a to 6c, the processing boards 3a to 3l, and the processing boards 5a and 5b.

Here, when the warning flag is set, it can be understood that, as for at lease the measured characteristic values 31, the defective fraction of any one of the characteristic values 31 corresponding to the individual channel numbers of the measuring machines 6a to 6c or the defective fraction for all the characteristic values 31 is equal to or larger than the threshold value. This phenomenon indicates that the abnormal state is generated in any one of the devices included in the manufacturing line system 100, as described above.

Therefore, in case of 'YES' in the step S41, the abnormality estimating unit 17 notifies the instruction output unit of a warning indicating that the abnormal state is generated. With this notification, the operator can confirm which device is abnormal.

On the other hand, when the warning flag is not set to one ('NO' in S41), the abnormality estimating unit 17 considers that diagnosis is impossible (S43) and ends the process.

As described above, the adjusting apparatus according to the present embodiment can specify the device to be adjusted having abnormality can specified, and can instruct to notify of the specified device to be adjusted or to adjust the set value of the device to be adjusted.

(Adjustment Processing of Set Value)

Next, when a notification of a purport that any one of the processing machine 5a or the processing machine 5b is not normally operation (in the abnormal state) is received from the abnormality estimating unit 17, the adjustment processing of the set value to be performed by the adjusting unit 18 will be described with reference to FIGS. 8 and 9.

Figure 8:
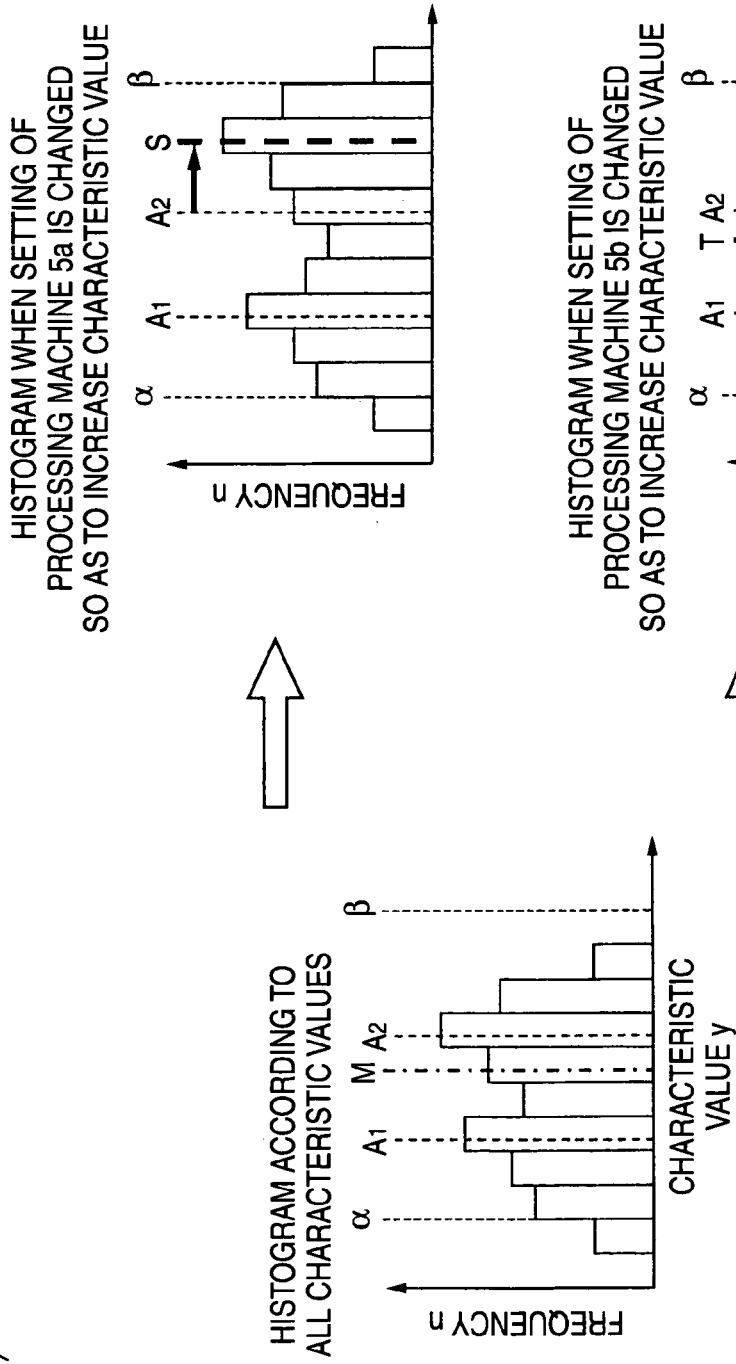
FIG. 8 is a diagram showing an example of an adjustment processing of a set value of the processing machine.
Figure 9:
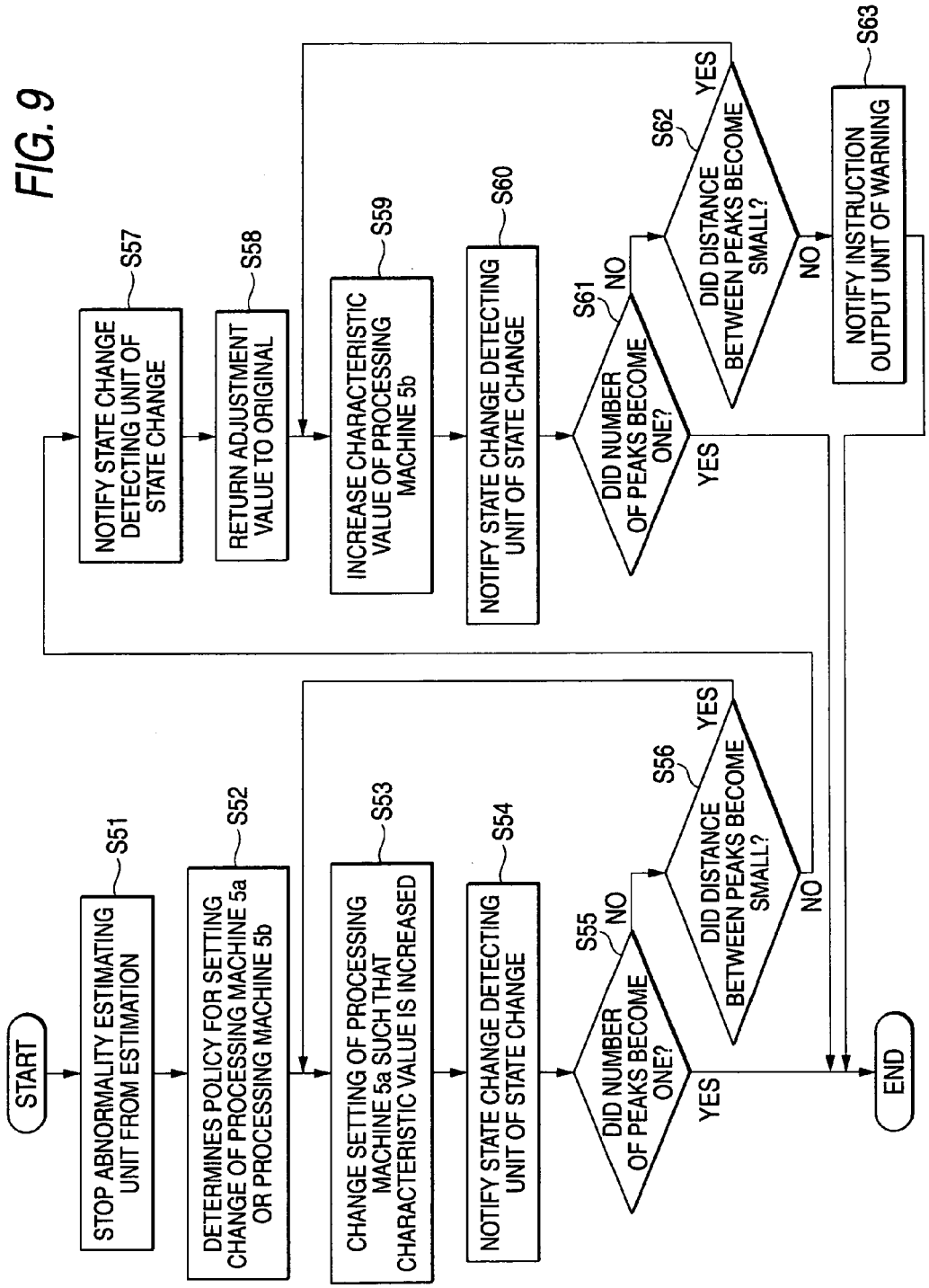
FIG. 9 is a flowchart showing an example of an adjustment processing of a set value of the processing machine.

Moreover, FIG. 8 is a diagram illustrating an example of the adjustment processing of the set value in the adjusting apparatus 7 according to the present embodiment. Further, FIG. 9 is a flowchart showing a search processing of a calibration value in the adjusting apparatus according to the present embodiment.

When any one of the processing machine 5a and the processing machine 5b is not normally operated, in the histogram on the basis of the characteristic values 31 of the articles processed by any one of the processing machines 5a and 5b, a peak section appears to be shifted from the median M of the regular range $\alpha$–$\beta$. For this reason, when any one of the processing machine 5a and the processing machine 5b is not normally operated, two peaks ($A_1$ and $A_2$) are generated in the histogram on the basis of all the measure characteristic values 31.

Here, in the adjusting apparatus 7 according to the present embodiment, the adjusting unit 18 compares the value of a section in which the peak $A_1$ appears and the value of a section in which the peak $A_2$ appears with the value of a section serving as the median M of the regular range $\alpha$–$\beta$.

Then, the set value of the processing machine is changed so as to cause the other peak value to approximate to one peak value closest to the value of the section of the median M.

That is, the articles processed by the other of the processing machine 5a and the processing machine 5b are normally processed. That is, in the distribution of the histograms on the basis of the characteristic values 31 of the articles processed by the other of the processing machines 5a and 5b, the histogram in which the peak appears in the section closest to the median M can be regarded as the histogram on the basis of the characteristic values 31 of the articles, which meet regular quality.

Then, the set value of the processing machine is changed so as to cause, from the peak $A_1$ and the peak $A_2$, the other peak value to approximate to one peak value closest to the median M of the regular range α–β. In such a manner, it is possible to approximate to the histogram on the basis of the characteristic values 31 of the articles, which meet regular quality.

Therefore, in the example of the histogram shown in FIG. 8, since the value of the section in which the peak $A_2$ appears is disposed in the vicinity of the median M, the set value of the processing machine 5a or the processing machine 5b may be changed such that the value of the section in which the peak $A_1$ appears is made larger.

Moreover, to the contrary, when the peak $A_1$ appears in the vicinity of the median M, the set value of the processing machine 5a or the processing machine 5b is changed such that the value of the section in which the peak $A_2$ appears is made smaller.

On the histogram shown in FIG. 8, as regards the peak $A_1$ and the peak $A_2$, it cannot be understood which peak value reflects the characteristic values 31 of the article processed by any processing machine.

Then, in the adjusting unit 18 according to the present embodiment, specifically, the set value of any one of the processing machine 5a and the processing machine 5b is changed such that the characteristic value 31 of the processed article is increased. Subsequently, the set value of the other of the processing machines is changed according to the change result.

For example, as shown in FIG. 8, when the set value of the processing machine 5a is first changed such that the characteristic value 31 is increased, it is assumed that, from the peak $A_1$ and the peak $A_2$ of the histogram on the basis of the measured characteristic values 31, the peak $A_2$ is moved up to a position indicated by S. That is, it is assumed that the distribution of the characteristic values 31 represented by the histogram extends beyond the upper limit value β in the regular range.

In this state, it can be understood that the variation of the distribution of the characteristic values 31 clearly extends, and the adjustment cannot be performed well. As such, when the adjustment cannot be performed, the set value of the processing machine 5a returns to the original again with reference to the apparatus initial value 32 stored in the information storing unit 12 in advance. Then, the set value of the processing machine 5b is changed with respect to the processing machine 5a. As a result, as shown in FIG. 8, it is assumed that the value of the peak $A_1$ of the histogram is moved up to the value of a section indicated by T.

That is, by changing the value of the peak $A_1$ up to the value of T, the total number of peaks in the histogram becomes one, and the peak appears in the vicinity of the median M in the regular range α–β of the characteristic values 31. Further, all the characteristic values 31 fall within the regular range α–β.

When the histogram on the basis of the characteristic values 31 measured in such a state appears, it can be judged that, by changing the set value of the processing machine 5b, the adjustment of the processing machine 5b is performed well.

In such a manner, in the manufacturing line system 100 according to the present embodiment, by changing the value where the peak appears in the histogram, the adjustment of the processing machine 5a or the processing machine 5b can be suitably performed. Hereinafter, a flow of the adjustment processing of the set value which adjusts the set value of any one of the processing machine 5a and the processing machine 5b will be described with reference to FIG. 9.

First, when receiving the notification of the purport that any one of the processing machine 5a and the processing machine 5b is not normally operated (in the abnormal state), the adjusting unit 18 instructs the abnormality estimating unit 17 to stop the estimation processing of the reason for abnormality (S51). As such, the adjusting unit 18 stops the estimation processing of the reason for abnormality by the abnormality estimating unit 17 during the adjustment processing of the set value.

Next, the adjusting unit 18 determines a policy for the setting change of the processing machine 5a or the processing machine 5b on the basis of the information of the histogram transmitted from the abnormality estimating unit 17, together with the notification (S52). The policy for the setting change determines to change the setting of the processing machine 5a or the processing machine 5b such that the characteristic value 31 of the article processed by any one of the processing machine 5a and the processing machine 5b is increased or decreased.

As described above, when the peaks appear in the two sections, the determination is performed according to whether the value of the section in which the other peak appears is increased or decreased on the basis of the section of one peak which appears in the vicinity of the median M of the regular value α–β.

In the present embodiment, as regards the determination, it is assumed that the adjusting unit 18 determines to change the set value of any one of the processing machine 5a and the processing machine 5b such that the characteristic value 31 of the processed article is increased.

Then, the adjusting unit 18 changes the set value of the processing machine 5a first such that the characteristic value 31 measured from the article processed by the processing machine 5a is increased (S53). Moreover, the change amount of the set value is a proper value, and may be a set value such that at least the characteristic value of the article processed by the processing machine having the changed set value is increased. That is, in the present embodiment, as a result, it is configured such that, by repeating the change of the set value, the shape of the histogram approximates to the histogram on the basis of the characteristic value of the processed article, which meets regular quality.

Here, if the set value of the processing machine 5a is changed, the characteristic value 31 to be obtained after the change is different from the characteristic value 13 before the change. Then, the adjusting unit 18 notifies the state change detecting unit 20 of a state change indicating that the setting of the processing machine 5a is changed (S54). According to this notification, the state change detecting unit 20 instructs the totaling unit 13 to total the characteristic values 31 once more. Next, according to the instruction from the state change detecting unit 20, the totaling unit 13 totals the characteristic values 31 of the processed articles after the set value of the processing machine 5a is changed.

Moreover, as regards the instruction to the totaling unit 13, the state change detecting unit 20 assigns and instructs the time at which the article processed by the processing machine 5a after the setting change is measured by any one of the measuring machines 6a to 6c.

That is, in the manufacturing line system 100 according to the present embodiment, it is configured such that the articles are transferred from the processing machine 5a up to the measuring machines 6a to 6c at a constant speed. For this reason, by calculating the time until the processed articles are transferred to the measuring machines 6a to 6c, the measurement time of the characteristic value 31 of the article processed by the processing machine 5a after the setting change can be understood.

Further, as described above, the characteristic values 31 measured by any one of the measuring machines 6a to 6c are stored in the information storing unit 12 in association with the measured time. For this reason, the totaling unit 13 can total the characteristic values 31 of the articles processed by the processing machine 5a having the changed set value.

In such a manner, the totaling unit 13 totals the characteristic values 31 of the articles processed by the processing machine 5a having the changed set value and creates the histogram on the basis of the characteristic values 31. Then, the totaling unit notifies the adjusting unit 18 of the information of the created histogram.

The adjusting unit 18 judges whether or not the number of peaks in the histogram becomes one on the basis of the histogram information received from the totaling unit 13 (S55). That is, the adjusting unit 18 judges whether or not the frequency of the characteristic values in the section in the vicinity of the median of the regular range $\alpha$–$\beta$ is increased and the frequency of the characteristic values in sections before and after that section is gradually decreased.

In the step S55, when the adjusting unit 18 judges that the number of peaks becomes one ('YES' in S55), the adjustment processing of the set value ends.

On the other hand, in case of 'NO' in the step S55, it is judged whether or not the distance between the two peaks which appear in the histogram of the received histogram information becomes small, as compared with the distance between the two peaks before the setting change of the processing machine 5a (S56). Moreover, the inter-peak distance can be calculated as an absolute value of the difference between the value of the section in which the peak $A_1$ appears and the value of the section in which the peak $A_2$ appears.

That is, when the setting change of the processing machine 5a is performed, though not particularly shown in FIG. 1, the adjusting unit 18 stores the values of the sections, in which the peaks appear, in the histogram on the basis of the characteristic values 31 before the setting change in the information storing unit 12. Then, the adjusting unit 18 compares the distance between the values of the sections of the individual peaks stored in the information storing unit 12 and the distance between the values of the sections of the individual peaks in the histogram received after the setting change of the processing machine 5a.

As regards this comparison, when the adjusting unit 18 judges that the inter-peak distance does not become small ('YES' in S56), the process returns to the step S53 and the change of the set value of the processing machine 5a is performed once more. Then, the steps S53 to S56 are repeated until the number of sections in which the peaks appear becomes one.

On the other hand, when the set value of the processing machine 5a is changed such that the characteristic value of the article processed by the processing machine 5a is increased, in the histogram on the basis of the characteristic values of the articles processed by the processing machine 5a or the processing machine 5b, the inter-peak distance does not become small. That is, in case of 'NO' in the step S56, the adjusting unit 18 notifies the state change detecting unit 20 of the state change indicating that the setting of the processing machine 5a is changed (S57).

The state change described herein means that the set value returns to the original set value since the result of the measured characteristic value is not favorable even when the set value of the processing machine 5a is changed. Then, the adjusting unit 18 returns the changed set value of the processing machine 5a to the original set value with reference to the apparatus initial value 32 (S58).

As such, if the set value of the processing machine 5a returns to the original value, the adjusting unit 18 changes the set value of the processing machine 5b such that the characteristic value measured from the article processed by the processing machine 5b is increased (S59). Subsequent steps S60 to S62 are the same as those performed with respect to the processing machine 5a, and the descriptions thereof will be omitted.

However, in the step S62, when the inter-peak distance does not become small even if the set value of the processing machine 5b is changed ('NO' in S62), the instruction output unit 19 is instructed to notify an warning.

That is, even if the set values of the processing machine 5a and the processing machine 5b are changed, the histogram based on the measured characteristic values does not approximate to the histogram on the basis of the characteristic values of the processed articles, which meet regular quality. For this reason, it is judged that the reason for abnormality of the measured characteristic values is not based on the mechanical error of the processing machine 5a or the processing error 5b.

Then, since the adjusting unit 18 instructs the instruction output unit 19 to notify the warning, the operator can understand that the reason for abnormality of the measured characteristic values is caused by the mechanical error of the processing machine 5a or the processing machine 5b.

Therefore, the operator can efficiently examine other reasons, for example, wear in any one of the processing machine 5a and the processing machine 5b.

As such, when the characteristic value measured from the processed article is out of the regular range, the adjusting apparatus 7 according to the present embodiment can specify the reason for abnormality on the basis of the characteristic values. That is, on the basis that the characteristic values out of the regular range appear by two cycles, three cycles, or eleven cycles, the adjusting apparatus 7 can efficiently specify any one of the processing machines 5a and 5b, any one of the measuring machines 6a to 6c, or any one of the processing boards 3a to 3l as the reason for abnormality.

In particular, the adjusting apparatus 7 can specify the reason for abnormality while processing the articles.

Further, the adjusting apparatus 7 can notify the operator of the reason for abnormality specified through the instruction to the instruction output unit 19.

In addition, when any one of the processing machines 5a and 5b is specified as the reason for abnormality, the adjusting unit 18 can adjust the set value of the processing machine 5a or 5b such that the characteristic values measured from the processed articles, which meet regular quality, are obtained.

Moreover, in the manufacturing line system 100 according to the present embodiment, the processing boards 3a to 3l, the processing machines 5a and 5b, and the measuring machines 6a to 6c are provided, but kinds of devices are not limited thereto. For example, an assembling machine may be provided. Preferably, the kinds of these devices are suitably selected according to the kinds of the articles to be processed.

Moreover, in the manufacturing line system 100 according to the present embodiment, the twelve processing boards 3a to 3l, the two processing machines 5a and 5b, and the three measuring machines 6a to 6c are provided, but the number of devices are not limited thereto. For example, any number of devices may be provided if the number of processing boards 3a to 3l, the number of the processing machines 5a and 5b, and the number of the measuring machines 6a to 6c are different from each other. The number of these devices can be determined according to the kinds of the articles to be processed, the number of articles, or the like.

Further, in the estimation processing of the reason for abnormality, the estimation processing is performed in the sequence number of presence/absence of abnormality of the measuring machines, presence/absence of abnormality of the processing boards, and presence/absence of abnormality of the processing machines, but the sequence number of the estimation processing is not limited thereto.

For example, the estimation processing may be performed from the devices having a high frequency of occurrence of an inconsistency in sequence. Alternatively, the sequence number may be determined according to a way of occurrence of an inconsistency of an individual device or a way of change of the characteristic value when the inconsistency is generated in an individual device.

Moreover, the way of occurrence of the inconsistency is, for example, a way of occurrence of the measurement error of the measuring machine or the like, a way of occurrence of looseness of the jig of the processing board or attachment of a fragment.

Further, as regards the way of change of the characteristic value, for example, when the measurement error of the measuring machine is generated, the characteristic value is gradually changed, while, when looseness of the jig of the processing board or attachment of the fragment is generated, the characteristic value is significantly changed within short time to some extent.

Further, the manufacturing line system 100 according to the present embodiment may be used for any process in a production process. Therefore, the processed articles, the characteristic values of which are measured by the measuring machines 6a to 6c, may be finished articles or articles during manufacture in the production process.

Moreover, as described above, in order to detect cyclicity of the characteristic values 31 out of the regular range, the cycle information detecting unit 16 uses the equations (2) to (4), but, the arithmetic method by the cycle information detecting unit 16 is not limited to thereto. For example, an FFT may be used.

For example, the cycle information detecting unit 16 holds the relationship (FIGS. 3B to 3D) between the transfer sequence number of the articles which are processed and the characteristic values of which are measured, and the characteristic values for each transfer sequence number of the article as time series data. That is, the transfer sequence number of the articles shown in the horizontal axis of each of FIGS. 3B to 3D is held as the value on the time axis.

Then, the cycle information detecting unit 16 may be configured to perform an arithmetic operation by the FFT (fast Fourier transformation) on time series data and to detect the cycle of occurrence of the characteristic value out of the regular range.

That is, by using power spectrums obtained as the result of the arithmetic operations by the FFT, cyclicity can be examined, like the results of the arithmetic operations of the equation (2) to (4).

For example, as described above, the relationship between the sequence number of the articles to be transferred by the transfer belt 8 and the characteristic values measured from the individual articles is set as time series data, and a range of the sequence number from 0 to 100 shown in the horizontal axis is regarded as one second. Referring to FIGS. 3B and 3C with time series data, for example, as shown in FIG. 3B, a case in which 50 characteristic values out of the regular range in the range of 0 to 100 appear can be held as a frequency of 50 Hz.

For this reason, as the result of the FFT on time series data, when an intensive wavelength appears at the position of 50 Hz, the characteristic values may be out of the regular range for every one. In this case, it can be estimated that abnormality is generated in any one of the processing machine 5a and the processing machine 5b.

Similarly, referring to FIG. 3C, as shown in FIG. 3C, a case in which 33 characteristic values exceeding the value of the regular range between 0 and 100 appear can be held as the frequency of 33 Hz.

For this reason, as the result of the arithmetic operation by the FFT on time series data, when an intensive wavelength appears at the position of 33 Hz, the characteristic values may be out of the regular range for every two. In this case, it can be estimated that abnormality is generated in any one of the measuring machines 6a to 6c.

Further, similarly, referring to FIG. 3D, as shown in FIG. 3D, a case in which 8 characteristic values exceeding the value of the regular range between 0 and 100 appear can be held as the frequency of 8 Hz.

For this reason, as the result of the arithmetic operation by the FFT on time series data, when an intensive wavelength appears at the position of 8 Hz, the characteristic values may be out of the regular range for every eleven. In this case, it can be estimated that abnormality is generated in any one of the processing board 3a to 3l.

As such, when the cycle information detecting unit 24 detects the cycle of occurrence of the characteristic values out of the regular range by the FFT arithmetic operation, cyclicity can be detected with superior precision, as compared with the arithmetic operations of the equations (2) to (4).

However, as shown in the equations (2) to (4), the sum of the sizes of the differences from the characteristic values 31 for every one, for every two, and for every eleven may be obtained. In this case, the amount of arithmetic operations becomes small, and a high-speed processing is achieved, as compared with the case in which the FFT is used.

Moreover, in the above-described adjusting apparatus 7, the configuration is described in which the device as the device to be adjusted can be estimated. Preferably, a configuration is provided in which the change state of the variation: of the characteristic values to be obtained as the adjustment result of the device specified as the device to be adjusted is displayed.

Figure 10:
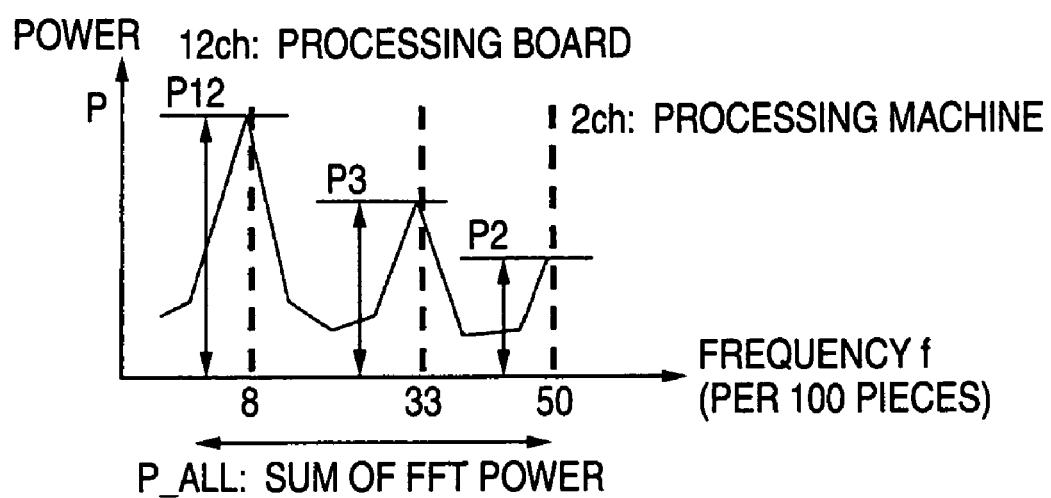
FIG. 10 is a diagram showing the results of arithmetic operations by an FFT with respect to time series data when any one of the processing boards is abnormal, when any one of the processing machines is abnormal, and when any one of the measuring machines is abnormal.

For example, it is assumed that abnormality is generated any one of the processing boards 3a to 3l, any one of the processing machines 5a and 5b, and any one of the measuring machines 6a to 6c. In this case, as the result of the arithmetic operation by the FFT on time series data, a power spectrum shown in FIG. 10 is obtained. That is, the amplitude of the wavelength becomes large at a frequency position of 8 Hz, 33 Hz, or 50 Hz.

Figure 11:
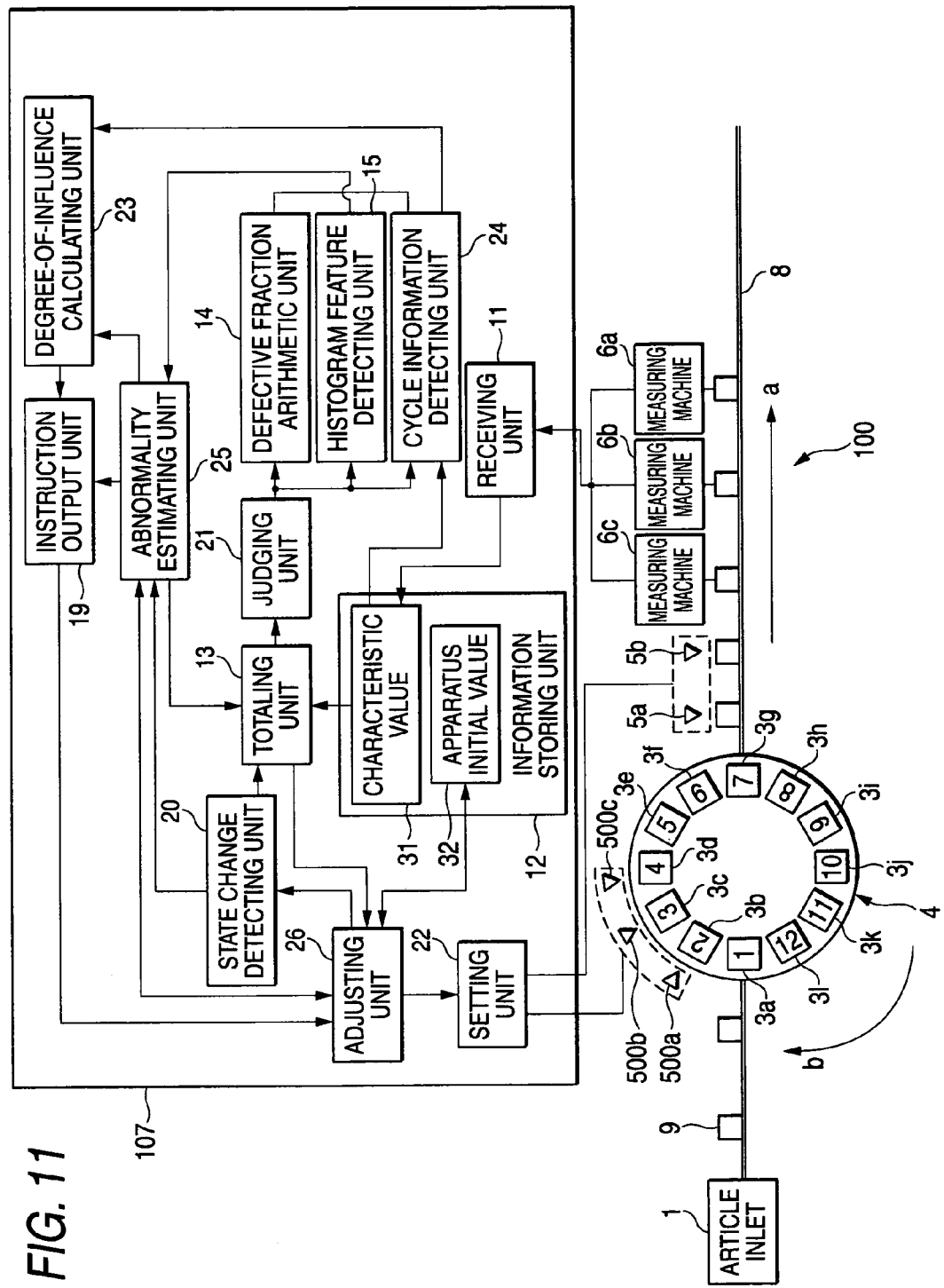
FIG. 11 is a block diagram showing an essential configuration of a manufacturing line system, which relates to a second embodiment of the present invention.
Figure 12:
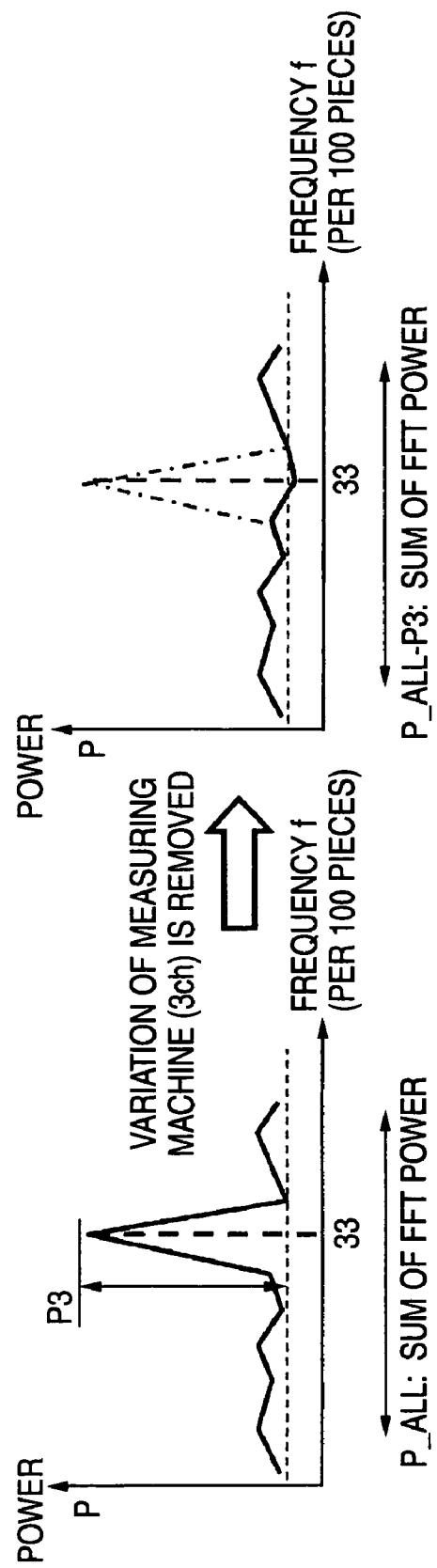
FIG. 12 is a diagram showing states of FFT power spectrums when abnormality is generated in the measuring machine and when it is assumed that the measuring machine having abnormality is adjusted.

However, when any one of the processing boards 3a to 3l is abnormal, when any one of the measuring machines 6a to 6c is abnormal, or when any one of the processing machines 5a and 5b, a degree that the characteristic values to be obtained from the articles are out of the regular range is different. That is, according to the device as the reason for abnormality, the variation of the difference between the characteristic value within the regular range and the measured characteristic value is generated. For this reason, the size of the amplitude at 8 Hz, 33 Hz, or 50 Hz shown in FIG. 11 is different.

Further, according to the kind of the reason for abnormality or the degree of abnormality in the device having the reason for abnormality, the size of the amplitude of the wavelength at the frequency position of 8 Hz, 33 Hz, or 50 Hz is different.

As such, since the degree that the measured characteristic value is shifted from the regular range is difference according to the device having the reason for abnormality and the reason for abnormality, when the device having the reason for abnormality is adjusted, the characteristic value obtained before the adjustment and the characteristic value obtained after the adjustment may be not changed so much.

In such a case, in view of working efficiency of the processing of the articles, and quality precision of the articles, the operator can judge that the adjustment of the device in the abnormal state does not need to be performed.

Hereinafter, an adjusting apparatus 107 which can display a change situation of the degree of variation in the characteristic values to be obtained as the adjustment result of the device specified as the reason for abnormality will be described.

As shown in FIG. 11, the adjusting apparatus 107 is different from the adjusting apparatus 7 in that a degree-of-influence calculating unit 23 is provided, in addition to the configuration of the above-described adjusting apparatus 7. The degree-of-influence calculating unit 23 estimates a degree of influence of the change in the characteristic value when the device to be adjusted is adjusted, on the basis of the information of the device to be adjusted notified from the abnormality estimating unit 25 and the information of the power spectrum received from the cycle information detecting unit (data collecting unit and translation calculating unit) 24.

Moreover, the degree of influence of the change in the characteristic value is an expected value of the degree of variation in the characteristic values to be obtained after the adjustment of the device to be adjusted is completed.

Further, the difference between the adjusting apparatus 107 and the adjusting apparatus 7 is as follows.

That is, the adjusting apparatus 107 is different from the adjusting apparatus 7 in that the adjustment instruction of any one of the processing machine 5a and the processing machine 5b to an adjusting unit 26 is performed from the instruction output unit 19.

Further, the adjusting unit 26 is different from the adjusting unit 18 in which the adjustment instruction of any one of the processing machine 5a and the processing machine 5b is received from the instruction output unit 19 and the policy for the setting change of the processing machine 5a or the processing machine 5b is determined on the basis of the information.

The adjusting unit 26 is different from the adjusting unit 18 in that the adjusting unit 26 acquires information of the histogram of the characteristic values 31 collected by the totaling unit 13 and determines the policy for the setting change of the processing machine 5a or the processing machine 5b based on the acquired information.

Further, a cycle information detecting unit 24 is different from the cycle information detecting unit 16 of the adjusting apparatus 7 in that, in order to detect cyclicity of the characteristic value out of the regular range, instead of the equations (2) to (4), the power spectrums obtained the results of the arithmetic operations by the FFT are used.

Further, an abnormality estimating unit 25 is different from the abnormality estimating unit 17 of the adjusting apparatus 7 in that the abnormality estimating unit 25 notifies the degree-of-influence calculating unit 23 of the information indicating the estimated device to be adjusted.

Moreover, in the adjusting apparatus 107, the same parts as those in the adjusting apparatus 7 are represented by the same reference numerals and the descriptions thereof will be omitted.

Here, in the degree-of-influence calculating unit 23, a flow of information on a calculation processing of the expected value of the degree of variation in the characteristic values to be obtained after the adjustment of the device to be adjusted is completed will be described.

First, the cycle information detecting unit 24 performs the arithmetic operation by the FFT by use of time series data on the basis of the characteristic values 31 stored in the information storing unit 12 and the transfer sequence number of the articles which are processed and the characteristic values of which are measured. Then, the obtained power spectrum and time series data are transmitted to the degree-of-influence calculating unit 23.

Further, the abnormality estimating unit 25 notifies the degree-of-influence calculating unit 23 of the result of the estimation processing of the reason for abnormality.

With respect to the device estimated as the reason for abnormality, that is, the device estimated as the device to be adjusted, the degree-of-influence calculating unit 23 calculates the change of the degree of variation in the characteristic values after the device to be adjusted is adjusted by use of the power spectrum obtained from the cycle information detecting unit 24.

Then, the information on the change of the degree of variation calculated is transmitted to the instruction output unit 19 to be displayed.

Hereinafter, the calculation processing of the change of the degree of variation in the characteristic values after the adjustment of the device to be adjusted by the degree-of-influence calculating unit 23 will be described.

(Calculation Processing of Change of Degree of Variation after Adjustment)

When a frequency to be obtained from the result of the arithmetic operation on time series data by the FFT is considered as a sine wave, the power spectrums obtained with respect to time series data by the FFT correspond to the second power of the amplitude of the frequency component of each cycle.

For this reason, the result of adding the power spectrums of the FFT, excluding an average value component (an offset component with respect to a frequency 0), is substantially proportional to the second power (that is, dispersion) of the standard deviation of time series data (excluding the influence of the average value in time series data). That is, before the calibration of an abnormal article, when the sum of all the FFT power spectrums (excluding the FFT power spectrum of the frequency 0) is 'P_all', and all the standard deviations before the calibration of the abnormal article is 'σ_all', the following equation (5) is established, where K is an arbitrary number.

$$P\_all = K \cdot (\sigma\_all)^2 \quad (5)$$

Moreover, when the result of the arithmetic operation with respect to time series data by the FFT is represented by the amplitude with 0 as the average level, the offset component with respect to the frequency 0 is a value required to reproduce time series data through a reverse Fourier translation with respect to that value again.

Here, as the reason for abnormality, it is assumed that any one of the measuring machines 6a to 6c is in the abnormal state and the measuring machine in the abnormal state is calibrated. As such, by calibrating the measuring machine in the abnormal state, the frequency component of the power spectrum, which appears at 33 Hz represented when any one of the measuring machines 6a to 6c is in the abnormal state, is decreased to approximate to about zero (white noise position) (see FIG. 12).

In this case, by deriving the standard deviation after the decreased from the standard deviation before the frequency component of the power spectrum at 33 Hz is decreased, the decrease amount of the standard deviation of time series data can be approximately estimated. That is, when the FFT power spectrum at 33 Hz before abnormality of any one of the measuring machines 6a to 6c is calibrated is 'P3' and the decrease amount of the standard deviation after abnormality of any one of the measuring machines 6a to 6c is calibrated is 'σ3', the relationship represented by the following equation (6) is established.

$$P3 = K \cdot (\sigma 3)^2 \quad (6)$$

Therefore, the degree-of-influence calculating unit 23 performs the arithmetic operations of the following equations (7) and (8) derived from the relationship of the equation (5) and the equation (6) so as to calculate the difference between all the characteristic values obtained before the calibration of the reason for abnormality and all the characteristic values obtained after the calibration.

First, the decrease amount of the standard deviation after abnormality of any one of the measuring machines 6a to 6c is calibrated is calculated by the following equation (7) obtained by use of the relationship of the equation (5) and the equation (6).

$$\sigma 3 = \sigma\_all * \sqrt{(P3/P\_all)} \quad (7)$$

σ3: the decrease amount of the standard deviation after the abnormal article (any one of the measuring machines 6a to 6c) is calibrated σ_all: all the standard deviations before the abnormal article (any one of the measuring machines 6a to 6c) is calibrated P3: the FFT power spectrum at 33 Hz before the abnormal article (any one of the measuring machines 6a to 6c) is calibrated P_all: the sum of all the FFT power spectrums (excluding the FFT power spectrum of the frequency 0) before the abnormal article (any one of the measuring machines 6a to 6c) is calibrated.

Therefore, the standard deviation of all the characteristic values measured after abnormality of any one of the measuring machines 6a to 6c is calibrated can be represented by the following equation (equation (8)).

Standard deviation of all characteristic values measured after abnormality calibration=σ_all−σ3 (8)

As such, by performing the arithmetic operations in such a manner, the degree-of-influence calculating unit 23 calculates the degree of variation of the characteristic values before and after the calibration of the reason for abnormality with respect to the characteristic values within the regular range and transmits the calculation result to the instruction output unit 19.

Moreover, all the values before the calibration of the reason for abnormality to be used for the above-described arithmetic operation can be obtained from time series data. That is, the degree-of-influence calculating unit 23 can calculate these values on the basis of the information of the power spectrums received from the cycle information detecting unit 24 and time series data.

Further, the decrease amount of the standard deviation after the calibration of the reason for abnormality can be obtained by virtually substituting the value of the power spectrum, which appears at a specified frequency, with the value of a white noise range.

For this reason, before the adjustment of the reason for abnormality, the degree-of-influence calculating unit 23 of the adjusting apparatus 107 can calculate the degree of variation of the characteristic values after the adjustment of the reason for abnormality.

Further, the adjusting apparatus 107 can output the degree of variation of the characteristic values after the adjustment of the calculated reason for abnormality to the instruction output unit 19, and thus the operator can judge whether or not to perform the adjustment of the reason for abnormality.

Further, unlike the adjusting apparatus 107 in which the degree of variation of the characteristic values after the adjustment is displayed, the adjusting apparatus 7 may be configured to judge presence/absence of necessity for the automatic adjustment of the reason for abnormality according to quality precision calculated from the article to be processed in advance and to output the judgment result to the instruction output unit 19.

Hereinafter, the configuration of an adjusting apparatus 207, which judges presence/absence of necessity of the automatic adjustment of the reason for abnormality according to quality precision calculated from the article to be processed in advance and outputs the judgment result to the instruction output unit 19, will be described.

Figure 13:
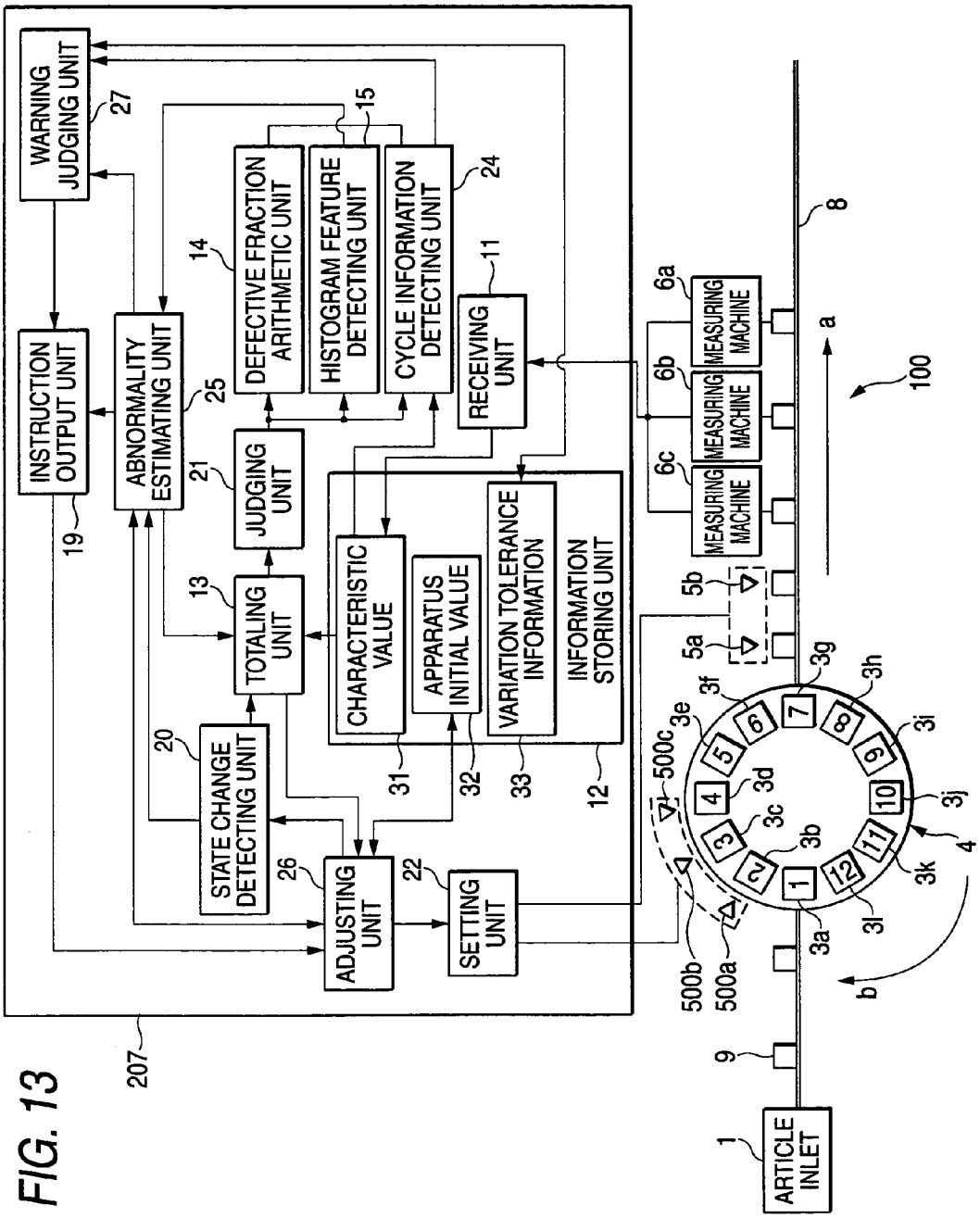
FIG. 13 is a block diagram showing an essential configuration of a manufacturing line system, which relates to a third embodiment of the present invention.

As shown in FIG. 13, the adjusting apparatus 207 is different from the adjusting apparatus 7 in that a warning judging unit 27 is provided, in addition to the configuration of the above-described adjusting apparatus 7, and the information storing unit 12 further stores variation tolerance information 33.

The variation tolerance information 33 is a decrease amount of the standard deviation after the estimation of abnormality on the device which is the reason for abnormality, and is a value which eliminates necessity for the adjustment of the reason for abnormality when at least the standard deviation is equal to or smaller than the decrease amount. This value is set in advance by the operator who operates the manufacturing line system 100.

Further, the warning judging unit 27 judges, on the basis of information of the device to be adjusted notified from the abnormality estimating unit 25, information of the power spectrum received from the cycle information detecting unit 24, and the variation tolerance information stored in the information storing unit 12, whether or not to perform the adjustment of the reason for abnormality. As the judgment result, when the adjustment of the device which is the reason for abnormality needs to be performed, the warning judging unit 27 outputs information indicating the warning to the instruction output unit 19.

Moreover, the judgment processing on whether or not to perform the adjustment of the reason for abnormality by the warning judging unit 27 will be described below.

Further, the difference of the adjusting apparatus 207 and the adjusting apparatus 7 is as follows.

That is, the adjusting apparatus 207 is different from the adjusting apparatus 7 in that the adjustment instruction of any one or the processing machine 5a or the processing machine 5b to the adjusting unit 26 is performed from the instruction output unit 19.

Further, the adjusting unit 26 is different from the adjusting unit 18 in that the adjusting unit 26 receives the adjustment instruction of the processing machine 5a or the processing machine 5b from the instruction output unit 19 and instructs the abnormality estimating unit 17 to stop the abnormality estimation processing.

Further, the adjusting unit 26 is different from the adjusting unit 18 in that the adjusting unit 26 acquires histogram information of the characteristic values 31 totaled by the totaling unit 13 and determines the policy for the setting change of the processing machine 5a or the processing machine 5b on the basis of the information.

Further, a cycle information detecting unit 24 is different from the cycle information detecting unit 16 of the adjusting apparatus 7 in that, in order to detect cyclicity of the characteristic values out of the regular range, instead of the equations (2) to (4), the power spectrums obtained as the results of the arithmetic operations by the FFT are used.

Further, an abnormality estimating unit 25 is different from the abnormality estimating unit 17 of the adjusting apparatus 7 in that the abnormality estimating unit 25 notifies the degree-of-influence calculating unit 23 of information indicating the estimated device to be adjusted.

Moreover, in the adjusting apparatus 207, the same parts as those in the adjusting apparatus 7 are represented by the same reference numerals and the descriptions thereof will be omitted.

Here, a flow of the judgment processing on whether or not to perform the adjustment of the reason for abnormality by the adjusting apparatus 207 will be described.

First, the cycle information detecting unit 24 performs the arithmetic operations by the FFT by use of time series data on the basis of the characteristic values 31 stored in the information storing unit 12 and the transfer sequence number of the articles which are processed and the characteristic values of which are measured. Then, the obtained power spectrums are transmitted to the degree-of-influence calculating unit 23.

Further, the abnormality estimating unit 25 notifies the degree-of-influence calculating unit 23 of the result of the estimation processing of the reason for abnormality.

When receiving the information of the device estimated as the reason for abnormality from the abnormality estimating unit 25, the warning judging unit 27 receives time series data on the basis of the information of the power spectrums received from the cycle information detecting unit 24 and the characteristic values 31.

Further, the warning judging unit 27 acquires the variation tolerance information 33 stored in the information storing unit 12.

Then, the warning judging unit 27 compares the threshold value obtained on the basis of time series data, the information of the power spectrums, and the variation tolerance information 33 with the power spectrums obtained by the arithmetic operations of the FFT with respect to time series data on the basis of the measured characteristic values 31. Next, the warning judging unit 27 judges whether or not to output the information indicating the warning to the instruction output unit 19.

Here, the calculation method of the threshold value, which is compared with the power spectrums obtained by the arithmetic operations of the FFT with respect to time series data on the basis of the measured characteristic values 31, will be described.

First, the warning judging unit 27 performs the arithmetic operation of the following equation (9) in order to calculate the threshold value. Moreover, here, as an example, it is assumed that the reason for abnormality is caused by any one of the measuring machines 6a to 6c.

$$Q3 = P\_all * (\gamma 3 / \sigma\_all)^2 \qquad (9)$$

Q3: the threshold value with respect to the FFT power spectrum at 33 Hz before the calibration of abnormality of any one of the measuring machines 6a to 6c.

P_all: all the FFT power spectrums (excluding the FFT power spectrum of the frequency 0) before the calibration of abnormality of any one of the measuring machines 6a to 6c.

σ_all: all the standard deviations before the calibration of abnormality of any one of the measuring machines 6a to 6c

γ3: the value which is permitted as the decrease amount of the standard deviation after the calibration of abnormality of any one of the measuring machines 6a to 6c

Here, as described above, the value of P_all can be calculated by the warning judging unit 27 which performs the arithmetic operations by the FFT with respect to time series data on the basis of the characteristic values 31 measured.

Further, as described above, the value of σ_all can be calculated by the warning judging unit 27 on the basis of time series data.

Further, as described above, the value of γ3 can be acquired by the information storing unit 12 as the variation tolerance information.

Moreover, Q3 calculated by the above-described arithmetic operation is the FFT power spectrum at 33 Hz before the calibration of abnormality in which the degree of variation of the characteristic values is permitted, and the power spectrum is set as the threshold value.

The, the warning judging unit 27 compares the threshold value (Q3) calculated by the above-described arithmetic operation with the power spectrum (P3) calculated by the FFT with respect to time series data on the basis of the actually measured characteristic values 31. As the comparison result, if the value of the former is smaller than the value of the latter (Q3<P3), the warning judging unit 27 outputs the information indicating the warning to the instruction output unit.

That is, when the relationship of 'Q3<P3' is established, the power spectrums obtained by the results of the arithmetic operations of the FFT with respect to time series data on the basis of the actually measured characteristic values 31 may be larger than the tolerance value of the power spectrum. That is, when the relationship of 'Q3<P3' is established, the degree of variation of the actually measured characteristic values 31 with respect to the characteristic values within the regular range exceeds the tolerance range.

Moreover, the variation tolerance information (γ3) 33 can be determined in advance according to quality precision calculated from the article to be processed. Therefore, when high quality precision is required, the value of the variation tolerance information (γ3) 33 becomes small.

As such, the adjusting apparatus 207 has the warning judging unit 27, thereby judging whether or not the adjustment of the reason for abnormality needs to be performed.

Therefore, in view of the change of the degree of variation of the characteristic values when the estimated device as the reason for abnormality is adjusted, it can be automatically judged whether or not to adjust the device estimated as the reason for abnormality.

Moreover, the warning judging unit 27 judges whether or not to calculate the threshold value through the arithmetic operation of the equation (9) and to output the warning. However, for ease of understanding, it can be configured such that the threshold value is displayed onto the instruction output unit 19 while translating all the measured characteristic values 31 into the standard deviation, instead of the power spectrums calculated by the FFT, thereby setting the threshold value.

Further, the individual parts included in each of the adjusting apparatus 7, the adjusting apparatus 107, and the adjusting apparatus 207 according to the present embodiment may be implemented by hardware logics or software logics.

That is, in case of the implementation by hardware, the individual parts or steps of each of the adjusting apparatus 7, the adjusting apparatus 107, and the adjusting apparatus 207 according to the present embodiment can be implemented by executing a program stored in a storage unit, such as the ROM (Read Only Memory) (not shown) or the RAM (not shown) and by controlling an input unit, such as a keyboard or the like, an output unit, such as a display or the like, and a communication unit, such as an interface circuit or the like, with an arithmetic unit, such as the CPU (not shown) or the like.

Therefore, only when a computer having these units reads a recording medium, on which the program is recorded, and executes the program, various kinds of functions and processings of the adjusting apparatus of the present embodiment are implemented. Further, by recording the program onto a removable recording medium, various kinds of functions and processings can be implemented on a certain computer.

As the recording medium, a program medium, such as a memory (not shown), for example, ROM, may be used for the processing of the microprocessor. Further, a program medium may be used in which a program reading apparatus may be provided as an external storage device (not shown), and the recording medium may be inserted therein so as to read the program.

Further, in any case, the stored program is preferably executed through an access of a microprocessor. In addition, preferably, the program is read out, the read program is downloaded in a program storage area of a micro computer, and then the program is executed. Moreover, it is assumed that the program for the download is stored in a main body apparatus in advance.

Further, the program medium includes a recording medium, which is configured to be removed from the main body, and which fixedly carries the program, for example, tapes, such as magnetic tapes or cassette tapes, discs, such as magnetic discs of flexible discs or hard discs, or discs, such as CD, MO, MD, DVD, or the like, cards, such as IC cards (including memory cards), or semiconductor memories, such as mask ROM, EPROM (Erasable Programmable Read Only memory) EEPROM (Electronically Erasable Programmable Read Only Memory), flash ROM, or the like.

Further, in case of a system configuration which can be connected to a communication network including Internet, it is preferable to use a recording medium which fluidly carries the program such that the program can be downloaded from the communication network.

In addition, when the program is downloaded from the communication network in such a manner, preferably, the program for the download is stored in the main body apparatus in advance or is installed from an individual recording medium.

In addition, when the program is downloaded from the communication network in such a manner, preferably, the program for the download is stored in the main body apparatus in advance or is installed from an individual recording medium.

The adjusting apparatus 7 according to the present embodiment can judge which device from various kinds of devices has abnormality in the manufacturing line system 100 in which various kinds of a plurality of devices are provided and the articles are processed by any one of various kinds of devices. For this reason, the present invention can be widely applied to a manufacturing line which performs mass production of various kinds of articles.

Figure 14:
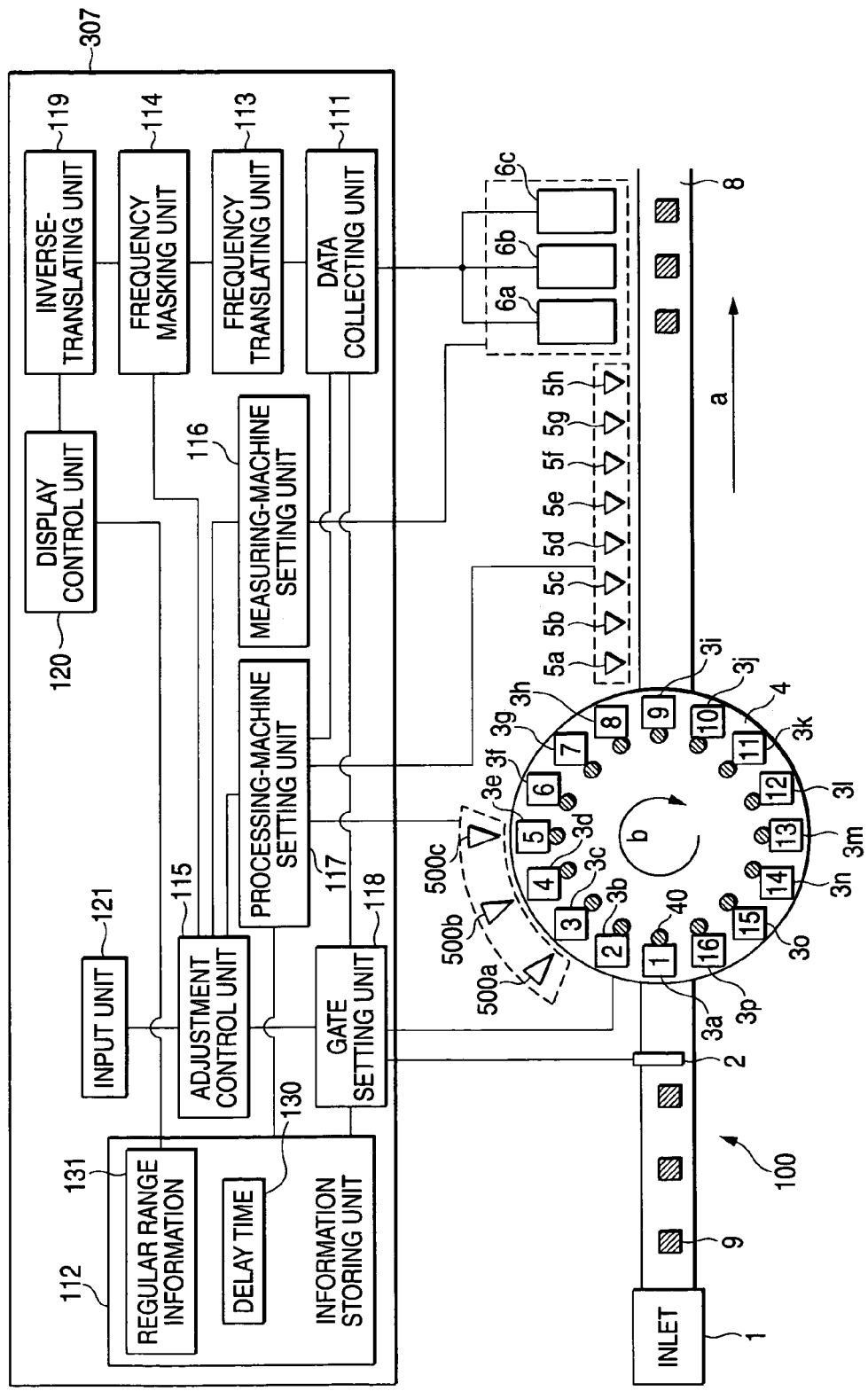
FIG. 14 is a block diagram showing an essential configuration of an adjusting apparatus, which relates to a fourth embodiment of the present invention.

Hereinafter, a fourth embodiment of the present invention will be described with reference to FIGS. 14 to 29. As shown in FIG. 14, a manufacturing line system 100 according to the present embodiment executes a first processing by three first processing machines 500a to 500c, which perform different processings on an article 9 to be processed (article to be produced). Further, the manufacturing line system 100 executes a second processing by any one of eight second processing machines 5a to 5h, which execute the same processing on the article 9.

Further, the manufacturing line system 100 is configured to examine quality of the article 9 processed by any one of three measuring machines 6a to 6c.

That is, in the manufacturing line system 100, different processings are executed by the first processing machines 500a to 500c. Then, eight second processing machines 5a to 5h can process eight articles 9 in parallel, and three measuring machines 6a to 6c can measure the characteristic values of three articles 9 in parallel. Moreover, the first processing machines 500a to 500c are referred to as the first processing machine 1500 when the descriptions thereof do not need to be distinguishably given. Further, the second processing machines 5a to 5h are referred to as the second processing machine 5 when the descriptions thereof do not need to be distinguishably given. Further, the measuring machines 6a to 6c are referred to as the measuring machine 6 when the descriptions thereof do not need to be distinguishably given.

Further, as for different processings, for example, the first processing machine 500a performs a processing for inserting parts into the article 9, the first processing machine 500b performs a processing for bending the article 9, and the first processing machine 500c performs a processing for welding the article 9.

Moreover, FIG. 14 is block diagram showing an essential configuration of the manufacturing line system 100, which relates to the embodiment of the present invention.

As shown in FIG. 14, the manufacturing line system (production system) 100 according to the present embodiment has an article inlet 1, a gate 2, a transfer belt 8, the first processing machines 500a to 500c, the second processing machines (production processing device, first production processing device, or second production processing device) 5a to 5h, processing boards (production processing device, first production processing device, or second production processing device) 3a to 3p, a turntable 4, the measuring machines (production processing device, first production processing device, or second production processing device) 6*a* to 6*c*, and an adjusting apparatus 307.

The function and structure of the article inlet 1, the transfer belt 8, the first processing machines 500*a* to 500*c*, the second processing machines 5*a* to 5*h*, the processing boards 3*a* to 3*p*, the turntable 4, and the measuring machines 6*a* to 6*c* are the same as those of the first embodiment as shown in FIG. 1, and thus the details of these members will be omitted.

The gate 2 adjusts the timing such that the articles 9 to be transferred by the transfer belt 8 are correspondingly housed in the processing boards 3*a* to 3*p*.

The processing boards 3*a* to 3*p* are provided to fix the articles so as to be processed by the first processing machines 500*a* and 500*c*. In the manufacturing line system 100 according to the present embodiment, the sixteen processing boards 3*a* to 3*p* are provided along the outer circumference of the circular turntable 4, as shown in FIG. 14. Then, the processing boards 3*a* to 3*p* are configured to be moved in a direction of an arrow b (a clockwise direction) according to the rotation of the turntable 4.

As such, in the manufacturing line system 100 according to the present embodiment, the three first processing machines 500*a* to 500*c* can execute a single first processing, and the eight second processing machines 5*a* to 5*h* can simultaneously perform the processing on eight articles 9.

Moreover, in the manufacturing line system 100 according to the present embodiment, the turntable 4 is provided so as to collect the installment places of the devices, such as the first processing machines 500*a* to 500*c* and the like.

Further, the turntable 4 has light-emitting portions (information output units) 40 . . . , such as LEDs (light emitting diodes) or the like, at positions corresponding to the processing boards 3*a* to 3*p*. Then, the light-emitting portions 40 . . . are set to be turned on when the processing board 3 is operated with the article 9 housed therein. For this reason, an administrator who manages the manufacturing line system 100 according to the present embodiment can easily grasp the operation state of the processing board 3. For this reason, for example, when a restoration working of the processing board 3 is required, a used can select the processing board 3, in which the light-emitting portion 40 is turned on, and perform the working, such that the user can easily perform a safe working.

Moreover, the light-emitting portion 40 is not limited to be provided corresponding to the processing boards 3*a* to 3*p*, but may be provided corresponding to other devices (the first processing machine 500, the second processing machine 5, or the measuring machine 6).

The adjusting apparatus 307 specifies a device to be adjusted on the basis of the characteristic values measured by the individual measuring machines 6*a* to 6*c* and instructs adjustment with respect to the device or changes setting of the device.

Moreover, in the manufacturing line system 100 according to the present embodiment, the device to be adjusted is one of the processing machines 5*a* to 5*h*, one of the processing boards 3*a* to 3*p* provided in the turntable 4, or one of the measuring machines 6*a* to 6*c*. Moreover, the detailed configuration of the adjusting apparatus 307 will be described below.

(Configuration of Adjusting Apparatus)

As shown in FIG. 14, the adjusting apparatus 307 according to the present embodiment has a data collecting unit 111, an information storing unit (storage device) 112, a frequency translating unit (translation calculating unit) 113, a frequency masking unit (extracting unit, masking unit) 114, an adjustment control unit (specifying unit, number-of-devices instruction unit) 115, a measuring-machine setting unit (setting unit) 116, a processing-machine setting unit (setting unit) 117, a gate setting unit (setting unit) 118, a inverse-translating unit (inverse-translating unit) 119, a display control unit (information output unit, first data output unit, second data output unit) 120, and an input unit 121.

The data collecting unit 111 receives the characteristic values of articles measured by the measuring machine 6 and creates time series data on the basis of the characteristic values.

When receiving start signals from the measuring-machine setting unit 116, the processing-machine setting unit 117, and the gate setting unit 118, which are described below, the data collecting unit 111 acquires the measurement results of the characteristic values of the predetermined number of articles 9 from a point of time at which the start signals are received. Then, the data collecting unit 111 creates time series data according to a transfer sequence number of the articles 9 on the basis of the acquired measurement results.

Moreover, as described above, the data collecting unit 111 receives the channel numbers for specifying the individual measuring machines 6*a* to 6*c* from the measuring machines 6*a* to 6*c*. Therefore, even when the characteristic values are simultaneously measured by the three measuring machines 6*a* to 6*c*, by referring to the channel numbers, time series data according to the transfer sequence number can be collected. Moreover, the data collecting unit 111 transmits created time series data to the frequency translating unit 113.

The frequency translating unit 113 performs frequency translation by an FFT (fast Fourier translation) on the basis of time series data of the characteristic values created by the data collecting unit 111. The frequency translating unit 113 transmits the translation result to the frequency masking unit 114 as frequency data.

When time series data is frequency-translated by the FFT, frequency data of the translation result is divided into a sine component and a cosine component on a frequency axis. Moreover, the sum of the second power of the sine component and the second power of the cosine component becomes a power spectrum at that frequency.

Moreover, the frequency translating unit 113 is configured to perform frequency translation by the FFT, but is not limited thereto. For example, frequency translation may be performed by other translation methods, such as wavelet translation or the like.

The frequency masking unit 114 divides frequency data (mask component) corresponding to the individual devices and other data (non-mask component) from frequency data received from the frequency translating unit 113. Moreover, the mask component is frequency data in the vicinity of a basic component and an aliasing component corresponding to the individual devices. That is, the mask component is a data stream (collection of frequency power) according to the result of frequency translation by the FFT. Further, frequency power is an integral value of power spectrums of a frequency corresponding to an individual device. That is, frequency power is single data of a specifying point of the result of frequency translation by the FFT.

The frequency masking unit 114 receives information indicating the number of individual devices in the operation state, together with information for specifying the individual devices (the measuring machine 6, the processing board 5, and the second processing machine 5) received from the adjustment control unit 115, and divides frequency data on the basis of the information. Then, divided frequency data is transmitted to the inverse-translating unit 119, which is described below. Moreover, the detailed description of the division processing of data by the frequency masking unit 114 will be described below.

Further, the frequency masking unit 114 transmits the integral value of the power spectrums of the frequency corresponding to each device to the adjustment control unit 115. The integral value of the power spectrums of the frequency is used for the adjustment control unit 115 described below to specify the device to be adjusted or to determine whether or not to end the adjustment processing of the device specified as the device to be adjusted.

The adjustment control unit 115 controls the individual parts included in the adjusting apparatus 307 according to the present embodiment. Specifically, the adjustment control unit 115 outputs instructions to the measuring-machine setting unit 116, the processing-machine setting unit 117, and the gate setting unit 118 to adjust the number of devices in the operation state of each of the measuring machine 6, the processing board 3, the second processing machine 5, and the first processing machine 1500 or to adjust setting.

Further, the adjustment control unit 115 outputs the number of devices in the operation state to the frequency masking unit 114, together with identification information for specifying the second processing machine 5, the measuring machine 6, and the processing board 3, and receives the integral value of the power spectrums of the frequency of each of the measuring machine 6, the processing board 3, and the second processing machine 5 from the frequency masking unit 114. Then, the adjustment control unit 115 calculates the standard deviations of the individual devices (the measuring machine 6, the processing board 3, and the second processing machine 5) on the basis of the received integral value of the power spectrums Next, the adjustment control unit 115 specifies a device having abnormality from the calculated standard deviations.

That is, the power spectrum obtained according to the arithmetic result of time series data by the FFT corresponds to the second power of the amplitude of the frequency component of each cycle. Then, the sum of the power spectrums is substantially proportional to the second power of the standard deviation of time series data. Therefore, the following relationship is established.

$$P\_all = K(\sigma\_all)^2 \quad (1)$$

(P_all is the sum of the power spectrums)
(K is an arbitrary constant)
($\sigma$_all is the standard deviation in time series data)

Therefore, the adjustment control unit 115 calculates the standard deviations of the individual devices from the power spectrums corresponding to the individual devices received from the frequency masking unit 114 by use of the relationship of the equation (1) and specifies the device to be adjusted on the basis of the standard deviations.

Further, in 'an adjustment processing of the device' described below, the adjustment control unit 115 performs the determination that the adjustment of the device specified as the reason for abnormality ends according to whether or not the size of the standard deviation is equal to or less than a predetermined position.

The information storing unit 121 is a readable/writable recording medium, and stores delay time 130 from the point of time at which the device is adjusted up to the time when the characteristic value of the article 9 processed by the device after the adjustment is measured by the measuring machine 6.

Figures 15, 16:
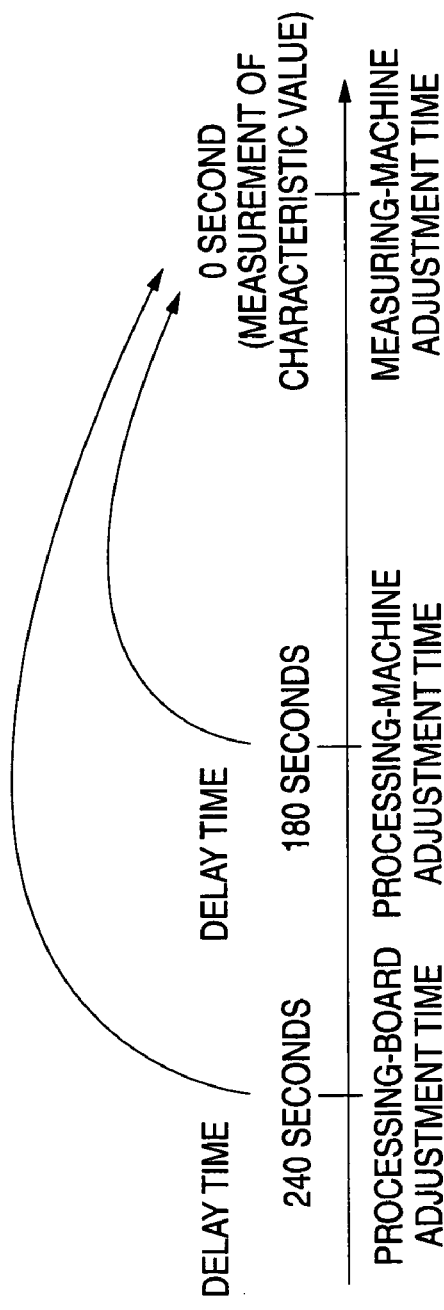
FIG. 15 is a diagram showing an example of delay time from adjustment time of a processing board, adjustment time of a processing machine, and adjustment time of a measuring machine up to measurement timing of a characteristic value, which relates to the embodiment of the present invention.
FIG. 16 is a diagram showing an example of reasons for abnormality which occur in the processing machine, the processing board, and the measuring machine according to the present embodiment.

As shown in FIG. 15, the delay time 130 represents the time until the article 9 processed by the adjusted device reaches the measuring machine 6. Then, by storing the delay time 130 in the information storing unit 121 for each device, the data colleting unit 111 can be prevented from confusedly collecting the characteristic values of the article 9 processed before the adjustment of the device and the article 9 processed after the adjustment.

In addition, the information storing unit 121 further stores regular range information 131. The regular range information 131 is information indicating a range of the characteristic values when the processed article 9 meets regular quality.

The measuring-machine setting unit 116 acquires information indicating operation states from the individual measuring machines 6a to 6c and notifies the adjustment control unit 115 of the acquired result or controls ON/OFF of the operations of the measuring machines 6a to 6c according to the instruction from the adjustment control unit 115.

The processing-machine setting unit 117 acquires information indicating operation states from the individual second processing machines 5a to 5h and notifies the adjustment control unit 115 of the acquired result or controls ON/OFF of the operations of the second processing machines 5a to 5h according to the instruction from the adjustment control unit 115. If ON/OFF is adjusted according to the instruction from the adjustment control unit 115, the processing-machine setting unit 117 instructs the data collecting unit 111 to collect data while being delayed from the adjustment time by the time (the delay time 130) until the characteristic value of the article 9 processed by the second processing machine 5 after the adjustment is measured by the measuring machine 6. Moreover, information indicating the delay time 130 is stored in the information storing unit 121 in advance, and the processing-machine setting unit 117 instructs the data collecting unit 111 to collect data with reference to the delay time 130 stored in the information storing unit 12.

Further, the processing-machine setting unit 117 is configured to control ON/OFF of the operations of the individual first processing machines 500a to 500c according to the instruction from the adjustment control unit 115.

The gate setting unit 118 adjusts the article 9 to be housed in any one of the processing boards 3a to 3p according to the instruction from the adjustment control unit 115. Further, the gate setting unit 118 manages information on which processing board 3 houses the article 9.

Specifically, the gate setting unit 118 controls the gate 2 in connection with the rotation of the turntable 4 so as to adjust whether or the article 9 is housed in the processing board 3. For example, when receiving from the adjustment control unit 115 the instruction of a purport that the article 9 is not housed in the processing board 3a, the gate setting unit 118 specifies the timing at which the article 9 is housed in the processing board 3, in connection with the rotation of the turntable 4. Then, at that timing, the gate 2 is put down on the transfer belt 8, and then the adjustment is performed such that the article 9 is not housed in the processing board 3a.

Further, in such a manner, when the processing board 3 is changed so as to house the article 9, the gate setting unit 118 instructs the data collecting unit 111 to collect data after the delay time 130 lapses from the point of time at which the change is made.

Further, when a failure occurs in the first processing machine 500, the second processing machine 5, the processing board 3, or the measuring machine 6 during the data collecting unit 111 collects the characteristic values, each of the measuring-machine setting unit 116, the processing-machined setting unit 117, and the gate setting unit 118 can instruct the data collecting unit 111 to stop the collection of data.

The inverse-translating unit 119 receives frequency data of the mask component or the non-mask component from the frequency masking unit 114 and performs a reverse Fourier translation (hereinafter, referred to as reverse FFT) on received frequency data. With the reverse FFT processing, the inverse-translating unit 119 generates time series data on the basis of frequency data of the mask component or time series data on the basis of frequency data of the non-mask component. Then, the inverse-translating unit 119 transmits generated time series data to the display control unit 120.

The display control unit 120 displays time series data received from the inverse-translating unit 119. Since the display control unit 120 displays time series data of the mask component from time series data, a cycle of occurrence of an abnormal characteristic value can be clearly represented.

That is, though described below, the mask component does not include an offset component, and shows only a variation of the characteristic value corresponding to a frequency band extracted as the mask component. Therefore, with time series data obtained as the result of the reverse FFT of the mask component, only a shift of the characteristic value caused by abnormality of the device is shown.

Moreover, the variation represents a distribution of the shift from an ideal value in a regular range. Further, the regular range is a range of the characteristic values when the processed article 9 meets regular quality. In the present embodiment, the regular range can be represented by an upper limit regular value and a lower limit regular value.

Further, the shift represents the difference between the measured characteristic value and the ideal value in the regular range. Moreover, the ideal value is a median between the upper limit regular value and the lower limit regular value.

On the other hand, when it is assured that the adjustment of the device estimated that abnormality occurs is completed, by causing the display control unit 120 to display time series data of the non-mask component, time series data of the characteristic value can be represented. Accordingly, after the adjustment of the device estimated that abnormality occurs, the shift of the characteristic value from the regular range can be represented.

Further, the display control unit 120 can also output the number of values out of the regular range from the values of time series data obtained through the reverse FFT of the non-mask component on the basis of the regular range information 131 stored in the information storing unit 12.

Further, the display control unit 120 can also calculate the standard deviation on the basis of time series data obtained through the reverse FFT of the non-mask component and output the standard deviation.

The input unit 121 receives an instruction from the user and transmits the received instruction to the adjustment control unit 115. For example, the instruction from the user can include instruction information for selecting a number-of-devices adjustment processing, an improvement prediction processing of abnormality of the characteristic value after the device adjustment, and the adjustment processing of the device as the reason for abnormality of the characteristic value, which are described below. Alternatively, if necessary, information, such as parameters or the like, required for the above-described individual processings is included.

(Reason for Device Abnormality)

Here, in the manufacturing line system 100 according to the present embodiment, the reason for abnormality in which the characteristic value measured from the article 9 is out of the regular range will be described with reference to FIG. 16. Moreover, FIG. 16 is a diagram showing the second processing machines 5a to 5h, the processing boards 3a to 3p, the measuring machines 6a to 6c, and the reasons for abnormality in the individual devices.

As described above, the manufacturing line system 100 according to the present embodiment has the first processing machines 500a to 500c, the second processing machines 5a to 5h, the processing boards 3a to 3p, and the measuring machines 6a to 6c. For this reason, when any one of the individual members is not normally operated, the measured characteristic value becomes abnormal. As the reason when the first processing machine 500 and the second processing machine 5 are not normally operated, a mechanical error in the first processing machine 500 or the second processing machine 5 or wear caused by the processing can be exemplified. Further, as the reason when the processing board 3 is not normally operated, looseness of a jig, which is a member used to install the article on the processing board 3, and attachment of a fragment to an installment portion of the article can be exemplified. Further, as the reason when the measuring machine 6 is not normally operated, a measurement error in the measuring machine 6, a shift of a measurement position, and the like can be exemplified.

Therefore, in a state in which any one of the second processing machines 5a to 5h, the processing boards 3a to 3p, or the measuring machines 6a to 6c is not normally operated, when the article 9 is processed, for example, the following phenomena shown in FIGS. 17A to 17C are observed in the characteristic value measured from the article 9.

Moreover, in FIGS. 17A to 17C, as an example of the measured characteristic value, 'an interval between parts' is used. Therefore, in FIGS. 17A to 17C, a vertical axis is set to mm (millimeter), which is a unit indicating 'the interval between parts', and a horizontal axis is set to the number of articles 9, the characteristic values of which are measured.

That is, when any one of the eight second processing machines 5a to 5h is not normally operated, as for the relationship between a sequence number of the articles 9 to be transferred and the characteristic values measured from the articles 9, as shown in FIG. 17A, the characteristic value is out of the regular range one time for every eight.

Further, when any one of the processing boards 3a to 3p is not normally operated, as for the relationship between the sequence number of the articles 9 to be transferred and the characteristic values measured from the articles 9, as shown in FIG. 17B, the characteristic value is out of the regular range one time for every sixteen.

Further, when any one of the measuring machines 6a to 6c is not normally operated, as for the relationship between the sequence number of the articles 9 to be transferred and the characteristic values measured from the articles 9, as shown in FIG. 17C, the characteristic value is out of the regular range one time for every three. As such, when any one of the second processing machine 5, the processing board 3, or the measuring machine 6 is not normally operated, it can be understood that the obtained characteristic value cyclically becomes a value out of the regular range.

Moreover, when abnormality occurs in any one of the first processing machines 500*a* to 500*h*, quality of all the articles 9 processed by the first processing is abnormal. That is, since all the characteristic values measured from the articles 9 exceed the regular range, cyclicity described above is not observed.

Therefore, in the present embodiment, as for the relationship between the transfer sequence number of the articles 9 and the characteristic values measured from the articles 9, time series data is considered with the sequence number as an time axis. Then, the adjusting apparatus 307 according to the present embodiment calculates frequency data through frequency translation of time series data by the FFT, specifies the device to be adjusted on the basis of frequency data, or adjusts the device.

Here, first, the relationship between time series data and data of time series data after the frequency translation will be described with reference to FIGS. 18A, 18B to 20A, and 20B. It is assumed that, as for the articles 9, the characteristic values of which are measured, the number of samples is 1024.

Figure 18A:
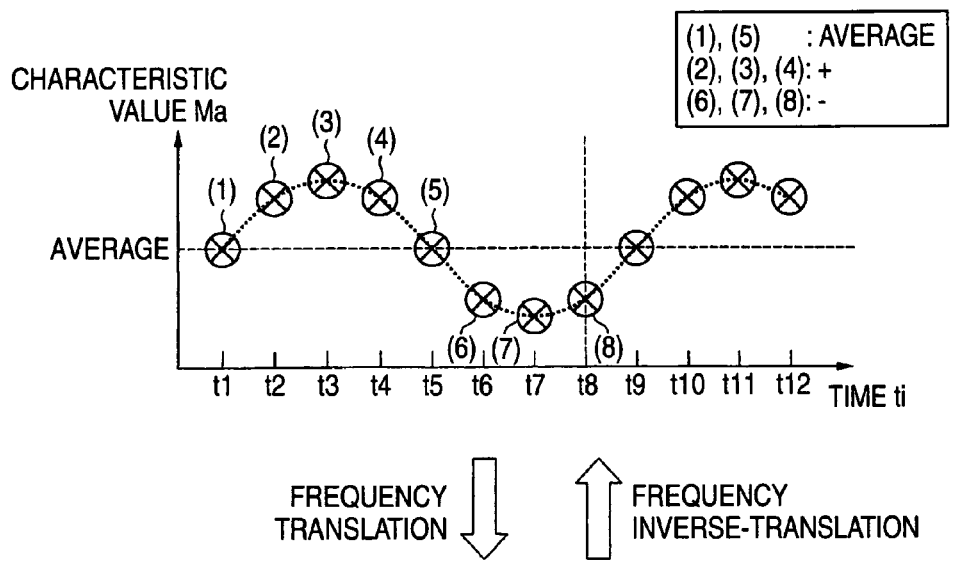
FIGS. 18A and 18B are diagrams showing an example of a degree of variation with respect to an average value of the characteristic values. Specifically.
Figure 18B:
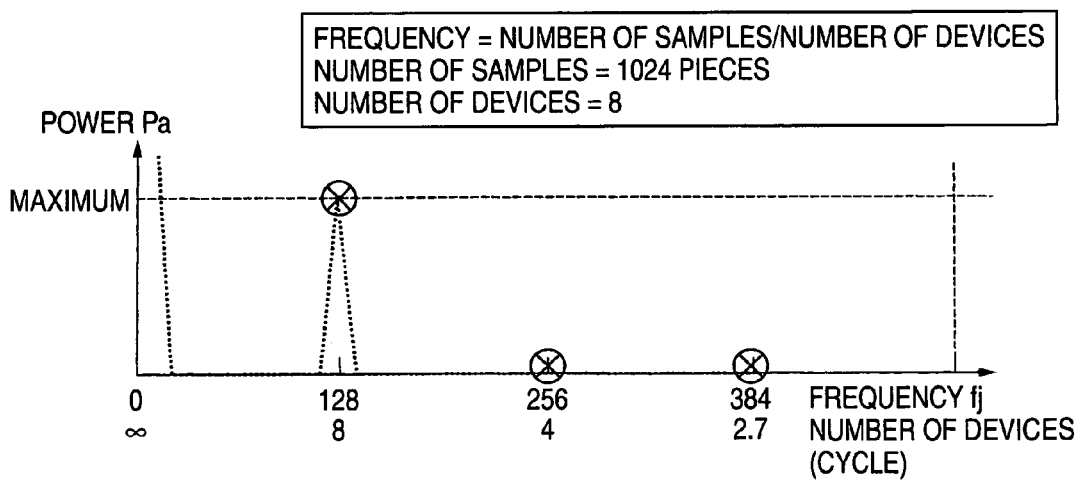

For example, as shown by time series data of FIG. 18A, when the waveform of time series data is a sine wave on the basis of the average value, that is, from the first to eighth articles, the characteristic values of the first and fifth articles become the average value, the characteristic values of the second to fourth articles 9 are equal to or more than the average value, and the characteristic values of the sixth to eighth articles 9 are equal to or less than the average value, in data of time series data before the frequency translation, as shown in FIG. 18B, a power spectrum is generated only at a frequency corresponding to the number of devices, which perform the processing.

In this case, the offset component (average) appears at a frequency fj=0 (infinite cycle), only the change component appears in the individual frequency components of fj=(1, 2, 3, . . . , 1023). For this reason, in this example, the frequency fj becomes 128 which is the value obtained by dividing the number of samples 1024 collected as time series data by the number of devices 8. That is, the power spectrum occurs at a position of the frequency fj=128.

Figure 19A:
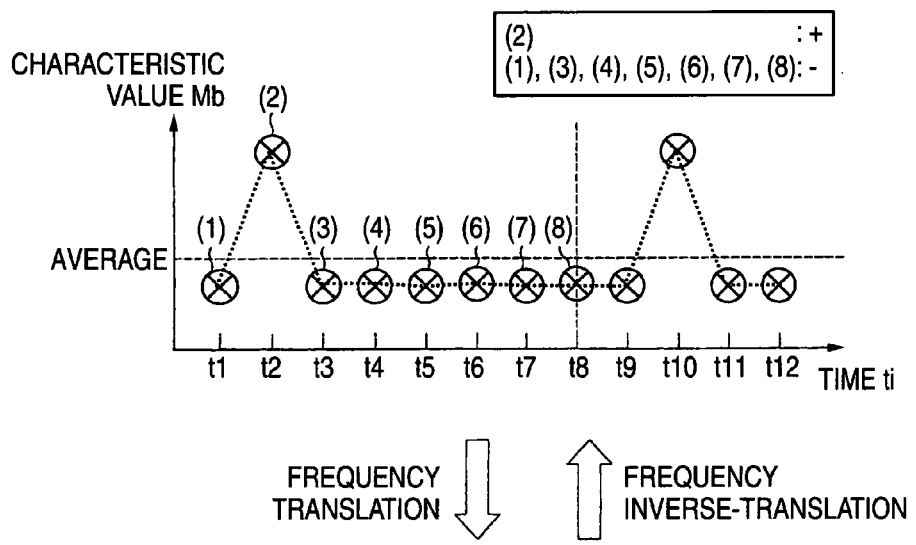
FIGS. 19A and 19B are diagrams showing an example of the degree of variation with respect to the average value of the characteristic values. Specifically.
Figure 19B:
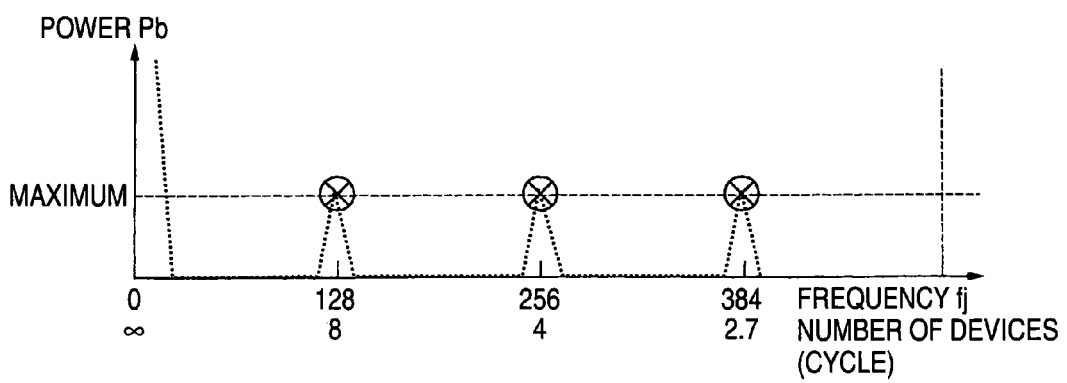

On the other hand, as shown in FIG. 19A, as for the first to eighth articles 9, time series data when only the characteristic value of the article 9 processed by the second device significantly exceeds the average value is in an impulse shape of the cycle 8. When the frequency translation is performed on such time series data, as shown in FIG. 19B, there occurs the power spectrum, which has the same size in the frequency component (basic component) corresponding to the number of devices 8 and the integer multiple thereof. Moreover, as described above, since the standard deviation is made small, as compared with the case in which time series data becomes the sine wave, the size of the generated power spectrum is made small.

Figure 20A:
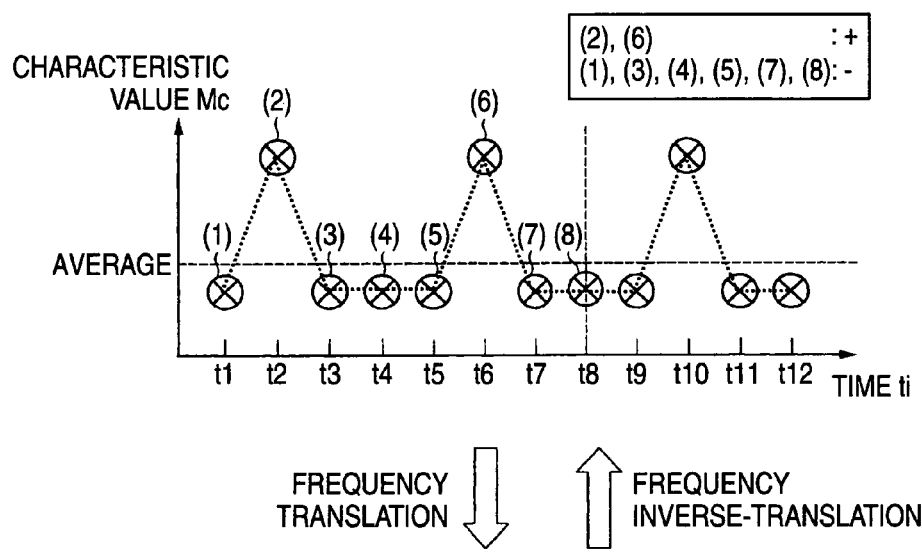
FIGS. 20A and 20B are diagrams showing an example of the degree of variation with respect to the average value of the characteristic values. Specifically.
Figure 20B:
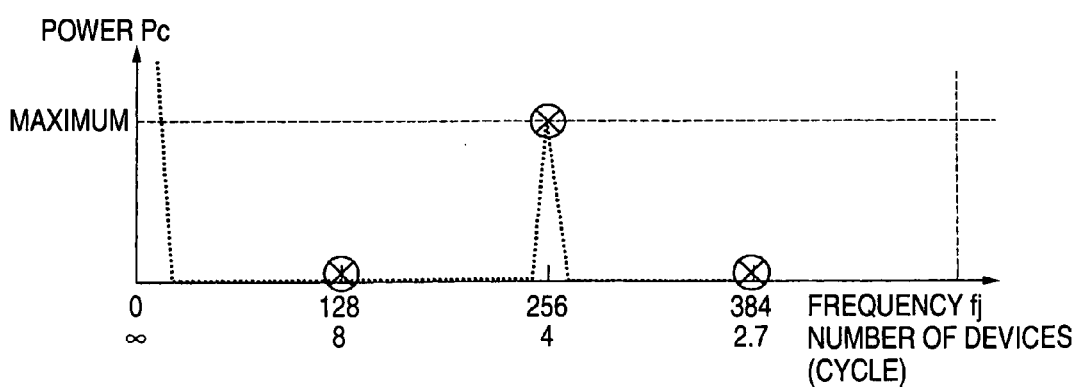

Further, as shown in FIG. 20A, as for the first to eighth articles 9, time series data when only the characteristic values of the second and sixth articles 9 significantly exceed the average value can be considered as an impulse shape of a cycle 4. That is, as such, in case of time series data when only the second and sixth characteristic values significantly exceed the average value, time series data is simultaneously processed by the four devices, and it can be considered as time series data when only the characteristic value of the article 9 processed by one from the devices significantly exceeds the average value.

Therefore, the power spectrums having the same height occur at the frequency (basic component) fj=256 corresponding to the number of device 4 and the frequency corresponding to the integer multiple thereof (aliasing component) However, the double of the frequency of the cycle 4 becomes the cycle 2, but, when the cycle is equal to or less than two, it is impossible to distinguish the difference in frequency according to a sampling theorem. As a result, in FIG. 20B, a single apparent power spectrum appears.

Further, when time series data shown in FIG. 20A and time series data shown in FIG. 19A have the same amplitude, the standard deviation of the former is made larger. For this reason, the size of the power spectrum obtained through the frequency translation of time series data shown in FIG. 20A is larger than the size of the power spectrum obtained through the frequency translation of time series data shown in FIG. 19A.

Moreover, as for the first to eighth articles 9, for example, when the characteristic values of the second and fifth articles 9 significantly exceed the average value, a small frequency power, other than the basic component and/or the aliasing component, is generated. However, as long as the number of devices for sampling is not changed, there is no case in which the frequency power does not occur in the basic component and/or the aliasing component.

With the relationship between time series data and frequency data after the frequency translation, the number-of-devices adjustment processing, the improvement expectation processing, and the adjustment processing of the device which are executed in the adjusting apparatus 307 according to the present embodiment will be described.

(Number-of-Devices Adjustment Processing)

Figure 21:
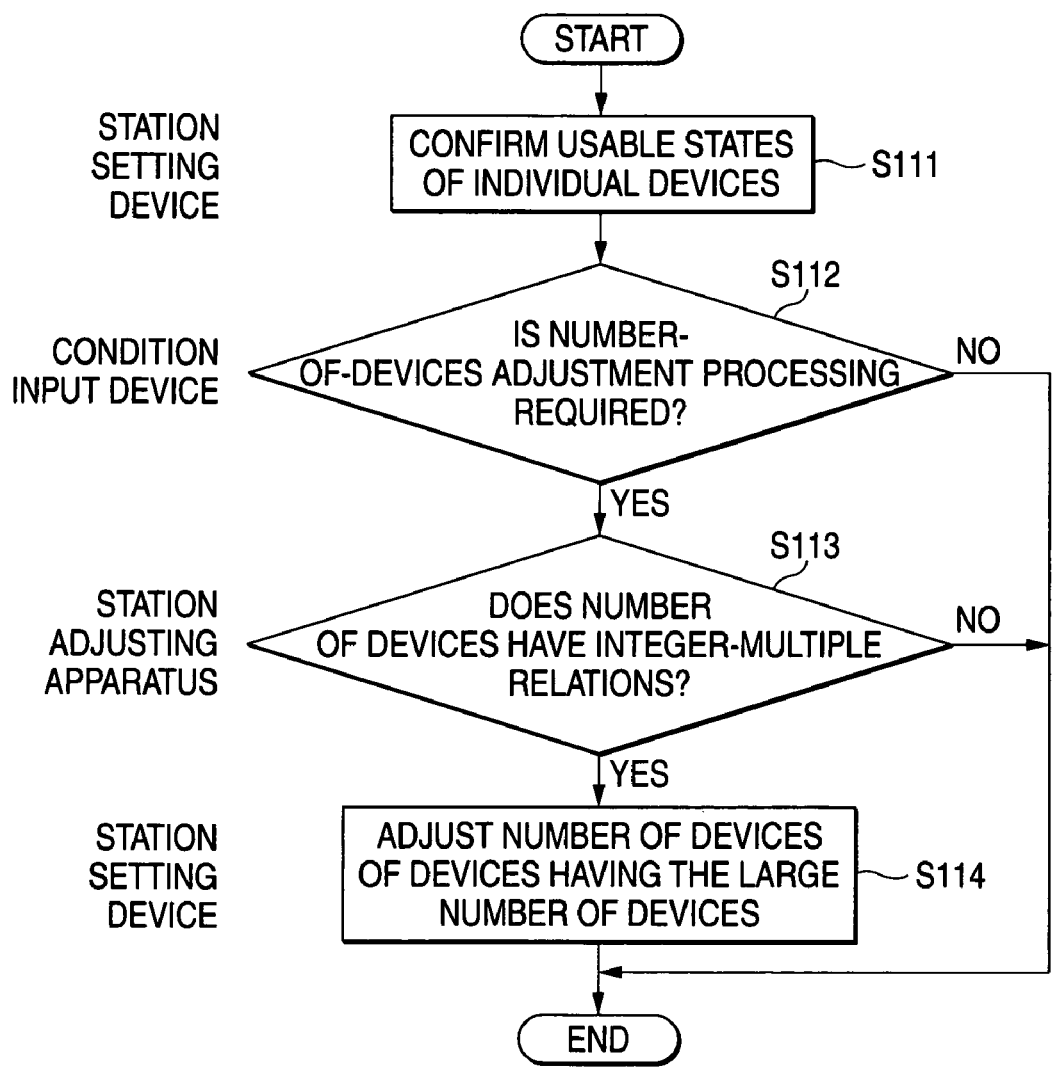
FIG. 21 is a flowchart of a flow of a number-of-devices adjustment processing in an adjusting apparatus according to the present embodiment.

Here, first, 'the number-of-devices adjustment processing' will be described with reference to FIG. 21. Moreover, as for 'the number-of-devices adjustment processing', the adjustment is performed such that, from the number of devices used for a production process of each of the second processing machine 5, the processing board 3, and the measuring machine 6, one does not become the double of the others, prior to the device as the reason for abnormality is specified.

That is, as described above, as for the relationship between the measured characteristic values and the transfer sequence number of the articles 9, the characteristic values of which are measured, when the transfer sequence number is considered as the time axis, the adjusting apparatus 307 according to the present embodiment creates time series data. Then, it is configured to perform the frequency translation on time series data and to specify the device as the reason for abnormality.

In such a case, when the following conditions are established, there is a problem in that the device as the reason for abnormality cannot be accurately specified.

That is, as for the operation number of the second processing machines 5, the operation number of the processing board 3, and the operation number of the measuring machine 6, when the relationship of the double to each other exists, one basic component overlaps the other aliasing component, the frequency may be confused. For this reason, there is a problem in that the adjusting apparatus 307 cannot accurately specify the device as the reason for abnormality from the result of the frequency translation of time series data of the obtained characteristic values.

Therefore, in the present embodiment, in order not to cause one basic component to overlap the other aliasing component, the number of devices in the operation state used for the production process of each of the second processing machine 5, the processing board 3, and the measuring machine 5 is configured to be adjusted.

Specifically, first, the measuring-machine setting unit 116, the processing-machine setting unit 117, and the gate setting unit 118 confirm the number of devices used for the production process of each device (Step S111) (hereinafter, referred to as S111). Moreover, the number of devices used for the production process is the number of devices in an operation state (ON state) at the time of the second processing machine 5 and the measuring machine 5, and is the number of devices, on which the articles can be installed, at the time of the processing board 3.

For example, the processing-machine setting unit 117 confirms whether power is the ON state or the OFF state in each of the second processing machines 5a to 5h, thereby confirming the number of device in the operation state used for the production process of the second processing machine 5. Further, for example, the measuring-machine setting unit 116 confirms whether power is the ON state or the OFF state in each of the measuring machines 6a to 6h, thereby confirming the number of device in the operation state used for the production process of the measuring machine 6. Further, for example, the gate setting unit 118 manages to open/close the gate 2 at which timing, thereby adjusting the number of device in the operation state of the processing boards 3a to 3p in which the articles 9 are housed.

Then, the measuring-machine setting unit 116, the processing-machine setting unit 117, and the gate setting unit 118 notify the adjustment control unit of the confirmed number of devices in the operation state used for the production process.

Here, it is judged whether or not the input unit 2 receives a request for the number-of-devices adjustment processing (S112). Then, when it is judged that the input unit 2 receives the request for the number-of-devices adjustment processing ('YES' in S112), the second processing machine 5, the number of devices used for the production process of each of the processing board 3, and the measuring machine 6, it is judged whether or not there is the combination of the devices having the double relationship (S113).

That is, the adjustment control unit 115 judges whether or not there is the combination of the devices having the double relationship on the basis of the information indicating the number of devices used for the production process received from each of the measuring-machine setting unit 116, the processing-machine setting unit 117, and the gate setting unit 118.

Then, in case of 'YES' in the step S113, the adjustment control unit 115 adjusts the number of devices for the device having the largest number of devices (S114).

In the manufacturing line system 100 according to the present embodiment, the number of processing boards 3 is sixteen, the number of second processing machines 5 is eight, the number of measuring machines 6 is three, and thus the number of processing boards 3 is the double of the number of second processing machines 5. Therefore, the adjustment control unit 115 determines to adjust the number of processing boards 3 in view of processing efficiency of the articles 9.

Specifically, the adjustment control unit 115 instructs the gate setting unit 118 to change the number of devices used for the production process of the processing board 3 from sixteen to fourteen. Moreover, as the result of the judgment of the step s13, in case of 'NO', the process ends as it is.

As such, by changing the number of devices used for the production process from sixteen to fourteen, the number of processing boards 3 is fourteen, the number of second processing machines 5 is eight, the number of measuring machines 6 are three, and thus there is no combination having the integer multiple relationship with respect to the number of devices in the operation state. That is, as for the number of processing boards 3 in the operation state, the number of second processing machine 5 in the operation state, and the number of measuring machines 6 in the operation state, the relationship in which one does not become the double of the other is established.

Therefore, when the device as the reason for abnormality is specified on the basis of the result of the frequency translation of time series data, in the adjusting apparatus 307 according to the present embodiment, the basic component and the aliasing component does not overlap each other, and thus the frequency can be prevented from being confused. For this reason, the adjusting apparatus according to the present embodiment can specify the device as the reason for abnormality with superior accuracy.

Moreover, as described above, when the number of devices used for the production process is changed, in the manufacturing line system 100 according to the present embodiment, the individual devices are operated as follows. For example, when the number of processing boards 3 in the operation state is changed, as described above, it can be implemented by causing the gate setting unit 118 to control open/close of the gate 2. More specifically, for example, when the processing board 3a cannot be used, the gate setting unit 118 controls open/close the gate 2 such that the article 9 is not housed in the processing board 3a.

Further, when the number of second processing machines 5 in the operation state is changed, as described above, it can be implemented by causing the processing-machine setting unit 117 to power off the second processing machine 5 to be stopped and to power on the second processing machine 5 in a power-off state. For example, when power of the second processing machine 5a is OFF, the processing-machine setting unit 117 instructs the transfer belt 8 to move the article 9 disposed to face the second processing machine 5a up to a position facing the second processing machine 5h by next movement.

Moreover, in the manufacturing line system 100 according to the present embodiment, as the second processing machine 5a to be powered off, for example, the second processing machine 5a or the second processing machine 5h is used. That is, it is preferable that one adjacent to another second processing machine 5 on only one side be selected.

That is, from a viewpoint that the number of second processing machines 5 used for the production process is adjusted, at least one of the second processing machines 5a to 5h may be powered off. Therefore, for example, the transfer speed of the article 9 may be adjusted by the transfer belt 8 or a gate (not shown) may be provided to adjust a transfer interval of the articles 9 such that the article 9 does not face the second processing machine 5 to be powered off. As for such adjustment on the transfer of the article 9, a case in which any one of the second processing machines 5b to 5g is powered off is more complicated than a case in which the second processing machine 5a or the second processing machine 5h is powered off.

For this reason, in view of ease of control on the transfer of the article 9, the configuration in which the second processing machine 5a or the second processing machine 5h is powered off is desirable.

Further, when the number of measuring devices 6 in the operation state is changed, as described above, it can be implemented by causing the measuring-machine setting unit 116 to power off the measuring machine 6 to be unusable or to power on the measuring machine 6 in the power-off state.

For example, when the measuring machine 6a is powered off, the transfer belt 8 adjusts the movement of the article 9 such that the article 9 facing the measuring machine 6a is moved to face the next measuring machine 6c. Moreover, when the measuring machine 6b is powered off, the transfer belt 8 adjusts the transfer interval of the article 9 to be transferred, such that, when one article 9 is disposed to face the measuring machine 6a, the other article 9 is disposed to face the measuring machine 6c. This adjustment can be implemented by providing a plurality of gates on the transfer belt 8 and by causing the other article 9 to face the measuring machine 6a at the timing at which one article 9 is disposed to face the measuring machine 6c.

Here, when any one of the second processing machines 5 or any one of the measuring machines 6 stops, a control method on the transfer of the article 9 will be specifically described with reference to FIG. 28. Moreover, here, the description will be given by way of an example in which any one of the measuring machines 6 stops.

Figure 28:
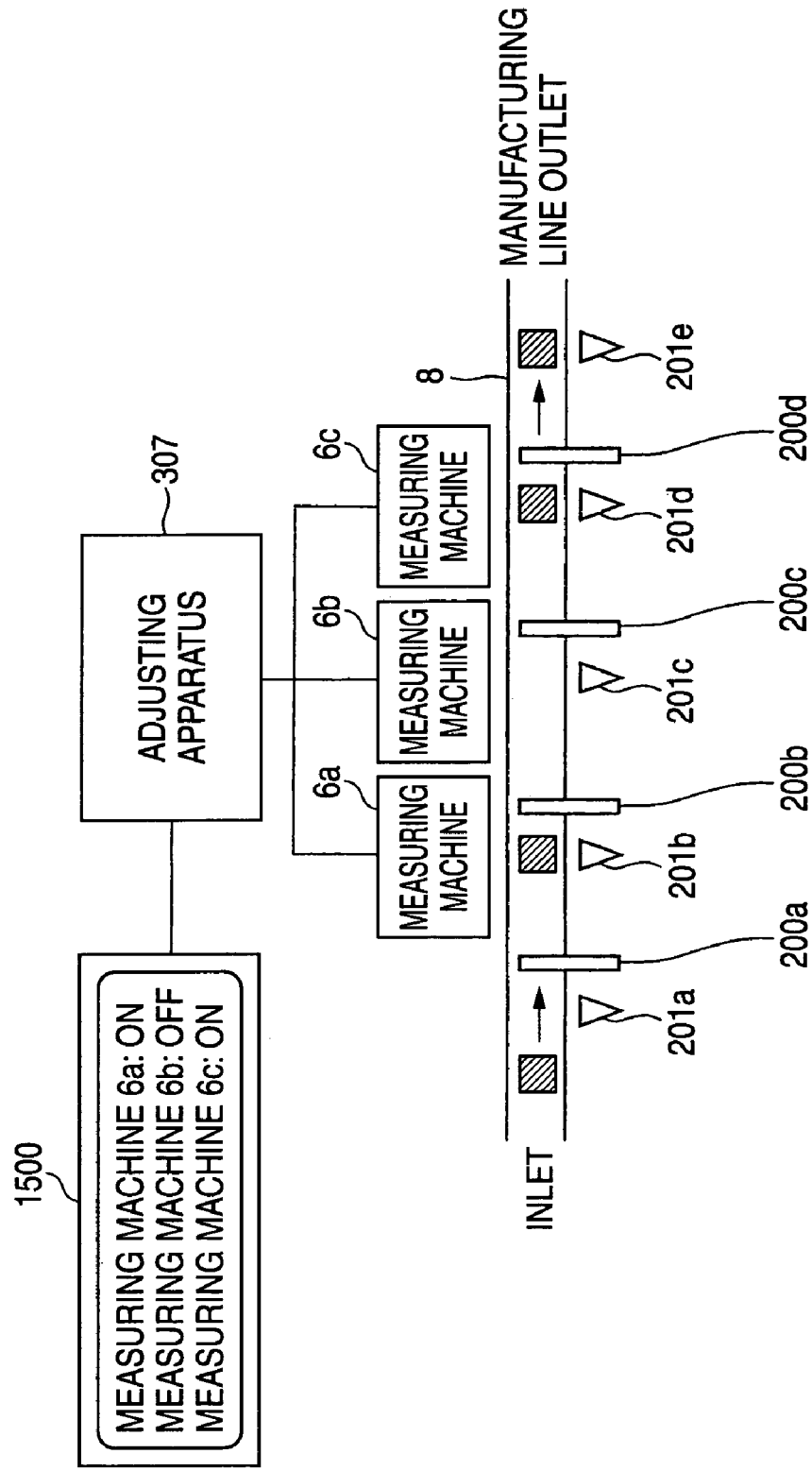
FIG. 28 is a diagram showing an example of a manufacturing line system according to the present embodiment and is a diagram showing an arrangement relationship between the measuring machines in the operation state and the article to be transferred by a transfer belt.

In the present embodiment, as shown in FIG. 28, a plurality of gates 200a to 200e are provided on the transfer belt 8. Further, on the inlet side of the gate on the transfer path of the article 9, sensors 201a to 201e are provided. Moreover, the gates 200a to 200d are simply referred to as the gate 200 when the descriptions thereof do not need to be distinguishably given. On the other hand, the sensors 201a to 201e are simply referred to as the sensor 201 when the descriptions thereof do not need to be distinguishably given.

Moreover, the gate 200 opens/closes to control passing of the article 9. On the other hand, the sensor 201 detects passing of the article 9 and can be implemented by, for example, an infrared sensor or the like.

The gate 200 opens/closes in connection with the detection result of the sensor 201. The relationship between the open/close of the gate 200 and the detection result of the sensor 201 will be described below with reference to FIG. 29.

Moreover, though not particularly shown in FIG. 28, the sensor 201, the gate 200, and the adjusting apparatus 307 are connected to one another, and it is configured such that the adjusting apparatus 307 can manage the open/close state of the gate 200 and the detection result of the sensor 200. That is, the adjusting apparatus 307 is configured to perform an open/close instruction to the gate 200, thereby managing the open/close state of the gate. Further, the adjusting apparatus 307 also manages ON/OFF of the measuring machine 6, thereby grasping the number of measuring machines 6 in the operation state.

First, as for the open/close state of the gate 200, it is assumed that the gate 200a and the gate 200d open, and the gate 200b and the gate 200c close (S141). In such an open/close state of the gate 200, the adjusting apparatus 307 judges whether or not the measuring machine 6c is in the ON state (S142).

Here, when the measuring machine 6c is in the ON state, the adjusting apparatus 307 sends an instruction to open the gate 200a. With this instruction, if the gate 200a opens (S143), at this point of time, the gates 200a to 200c are in the close state. Next, the adjusting apparatus 307 maintains the open/close state of the gate 200 at the current state until information indicating passing of the article 9 is detected from the sensor 201d, that is, when it is judged as NO in the step S144. Then, if the detection result indicating passing of the article 9 is received from the sensor 201d ('YES'0 in the S144), the adjusting apparatus 307 sends an instruction to the individual gates 200 so as to close the gate 200a and the gate 200c.

According to the instruction from the adjusting apparatus 307, if the gate 200a and the gate 200c close (S145), the open/close state of the gate, the gate 200a, the gate 200c, and the gate 200d are in the close state. That is, the article 9 is interposed between the gate 201d and the gate 201c, and only the interposed article 9 can be disposed to face the measuring machine 6c in the ON state.

Moreover, when the measuring machine 6c is not in the ON state ('NO' in S142), as for the open/close state of the gate, the gate 200c is in the close state, in addition to the gate 200a and the gate 200d.

Next, the adjusting apparatus 307 judges whether or not the measuring machine 6b is in a powered-on state (S146). As the result of the judgment, if it is judged that the measuring machine 6b is ON ('YES' in S146), the adjusting apparatus 307 sends an instruction to close the gate 200a. According to this instruction, the gate 200a opens (S147). At the point of time, as for the open/close state of the gate 200, the gate 200c and the gate 200d are in the close state.

Next, until the information indicating passing of the article 9 is detected from the sensor 201c, that is, when it is judged as NO in the step S148, the adjusting apparatus 307 maintains the open/close state of the gate 200 at the current state. Then, if the detection result indicating passing of the article 9 is received from the sensor 201c ('YES' in S148), the adjusting apparatus 307 sends an instruction to the individual gates 200 to close the gate 200a and the gate 200b.

According to the instruction from the adjusting apparatus 307, if the gate 200a and the gate 200b close (S149), as for the open/close state of the gate 200, all the gates 200a to 200d are in the close state. Further, the article 9 is interposed between the gate 200b and the gate 200c, and only the interposed article 9 can be disposed to face the measuring machine 6b in the ON state.

Moreover, when the measuring machine 6b is not in the ON state ('NO' in S146), as for the open/close state of the gate, the gate 200b is in the close state, in addition to the gate 200c and the gate 200d.

Next, the adjusting apparatus 307 judges whether or not the measuring machine 6a is in the powered-on state (S150). As the result of the judgment, when it is judged that the measuring machine 6a is ON ('YES' in S150), the adjusting apparatus 307 sends an instruction to close the gate 200a. According to this instruction, the gate 200a opens (S151). At this point of time, as for the open/close state of the gate 200, the gates 200b to 200d are in the close state.

Next, until the information indicating passing of the article 9 is detected from the sensor 201b, that is, when it is judged as NO in the step S152, the adjusting apparatus 307 maintains the open/close state of the gate 200 at the current state. Then, if the detection result indicating passing of the article 9 is received from the sensor 201b ('YES' in S152), the adjusting apparatus 307 sends an instruction to close the gate 200a.

According to the instruction from the adjusting apparatus 307, if the gate 200a close (S153), as for the open/close state of the gate 200, all the gates 200a to 200d are in the close state. Further, the article 9 is interposed between the gate 200a and the gate 200b, and only the interposed article 9 can be disposed to face the measuring machine 6a in the ON state.

Moreover, when the measuring machine 6b is not in the ON state ('NO' in S150), as for the open/close state of the gate, all the gates 200 from the gate 200a to the gate 200d are in the close state.

Then, in the open/close state of the gate 200 and the arrangement state of the article 9, the characteristic values of the articles 9 are measured by the individual measuring machines 6a to 6c. Next, if the measurement of the characteristic values is completed, the adjusting apparatus 307 sends an instruction to open the gates 200b to 200d, such that gates 200b to 200d are in the open state. As a result, the articles 9, which are interposed between the gate 200a and the gate 200b, the gate 200b and the gate 200c, and/or the gate 200c and the gate 200d, and are stopped, are moved by the transfer belt 8 again. Then, until the individual sensors 201b to 201d are continued in a non-detection state for predetermined time ('NO' in S155), the current open/close state 200 is maintained, and, if predetermined time lapses from the non-detection state ('YES' in S155), the process returns to the step S144.

As such, by controlling the open/close of each gate, the articles 9 can be properly arranged at positions facing the individual measuring machines 6a to 6c in the powered-on state.

Moreover, in the adjusting apparatus 307 according to the present embodiment, when the number of measuring machines 6 in the operation state is adjusted, the measuring machine 6 is powered on or off. Alternatively, by the control of the open/close state of the gate 200, as described above, the article 9 may be arranged to face a specified measuring machine 6.

Moreover, in the adjusting apparatus 307, in view of the processing efficiency of the articles 9, it is preferably configured such that the number of devices (the minimum number of devices in the operation state), which can be set as unusable devices, can be inputted by the input unit 121. Further, the adjusting apparatus 307 may be configured to store the minimum number of devices in the operation state in the information storing unit 121 in advance.

When the adjusting apparatus 307 is configured in such a manner, in 'the number-of-devices adjustment processing', the number of unusable devices can be limited, and thus processing efficiency of the articles 9 can be prevented from being drastically degraded.

(Improvement Expectation Processing)

Next, 'an improvement expectation processing' will be described with reference to FIG. 22. The improvement expectation processing is a processing for representing expectation how much the shift of the measured characteristic value from the ideal value is improved by adjusting the device specified that abnormality occurs. Moreover, the ideal value is the median between the upper limit regular value and the lower limit regular value.

When data created by arranging the measured characteristic values in the transfer sequence of the articles 9 is considered as time series data, 'the improvement expectation processing' is performed by use of frequency data obtained through the frequency translation of time series data by the FFT. For this reason, in order to execute the improvement expectation processing, the frequency translation needs to be performed on the basis of time series data.

That is, the data collecting unit 111 acquires a plurality of measured characteristic values from the measuring machine 6 according to the transfer sequence number of the articles 9. Moreover, it a predetermined number of characteristic values are acquired, the data collecting unit 111 is configured to stop the collection of the characteristic values.

Then, on the basis of data of the predetermined number of acquired characteristic values, the data collecting unit 111 creates time series data with the transfer sequence number of the articles 9 as the time axis (S121). Next, the data collecting unit 111 transmits created time series data to the frequency translating unit 113.

Figure 23A:
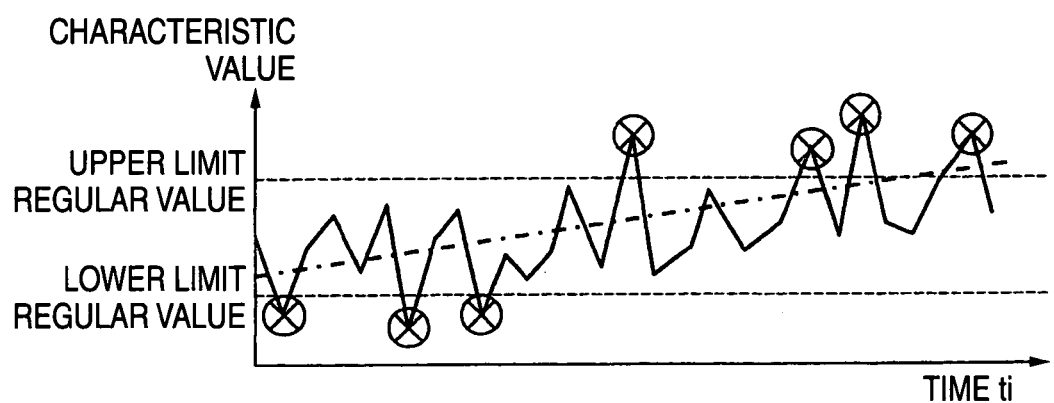
FIGS. 23A and 23B are diagrams showing a measurement result of the characteristic values by the measuring machine according to the present embodiment. Specifically.

Moreover, in the manufacturing line system 100 according to the present embodiment, it is assumed that, through 'the number-of-devices adjustment processing' described above, as for the number of devices in the operation state used for the production process of each device, the processing boards 3 is fourteen, the second processing machines 5 is eight, and the measuring machines 6 is three. Under this assumption, it is assumed that time series data obtained with the number of samples of 1024 for the article 9 is, for example, as shown in FIG. 23A. Then, in time series data, seven characteristic values are out of the regular range, that is, abnormal.

Figure 23B:
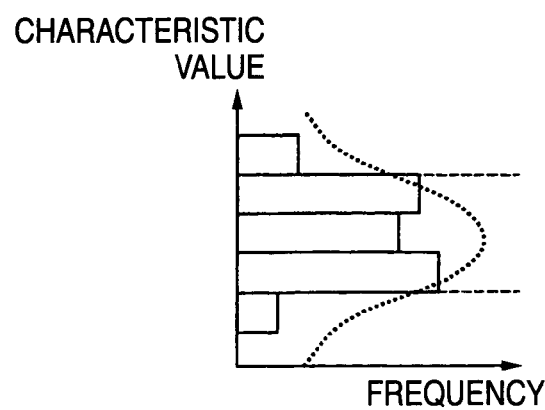

In time series data shown in FIG. 23A, a flag tends to significantly be increased as a whole. For this reason, when time series data is shown by a histogram, as shown in FIG. 23B, a data distribution is close to a rectangular shape. For this reason, time series data shown in FIG. 23B cannot approximate to a regular distribution. Accordingly, when the number of characteristic values out of the regular range is calculated by use of the average or the standard deviation with respect to such data, an apparent standard deviation is made large, and thus the number of characteristic values out of the regular range is calculated to be larger than the real number of characteristic values out of the regular range.

Accordingly, in order to accurately calculate the number of characteristic values out of the regular range, in time series data of FIG. 23A, the number of characteristic values out of the regular range is directly counted.

In the frequency translating unit 113, on the basis of time series data received from the data collecting unit 11, the frequency translation by the FFT is performed so as to calculated frequency data (S122).

Figure 24:
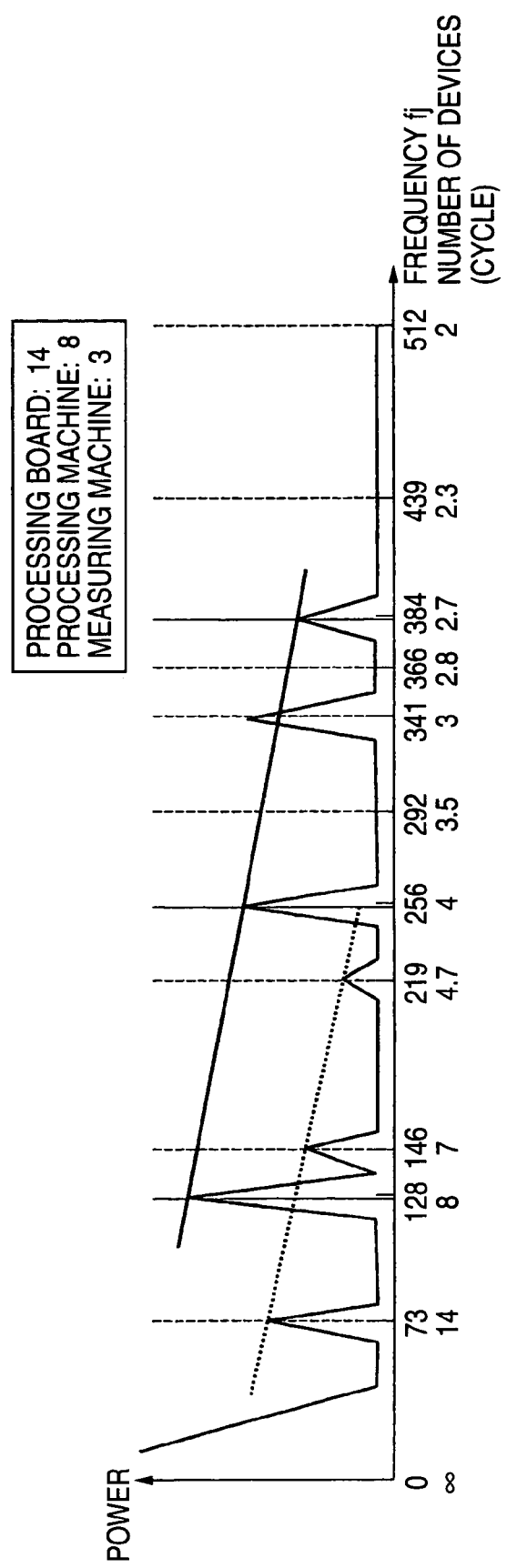
FIG. 24 is a diagram showing an example of frequency data obtained from the result of frequency translation when the characteristic values measured by the measuring device according to the present embodiment and the transfer sequence number of the articles corresponding to the characteristic values.

Here, calculated frequency data is as shown in FIG. 24. For example, when abnormality occurs in any one of the fourteen processing boards 3, the variation of the characteristic values can be represented by a power spectrum in which the number of devices is 14 and the position of the frequency fj=73 becomes the basic component. Further, the aliasing component can be represented by a power spectrum at a position of the frequency fj=146 and 219.

On the other hand, for example, when abnormality occurs in any one of the eight second processing machines 5, the variation of the characteristic values can be represented by a power spectrum in which the number of devices is 8 and the position of the frequency fj=128 becomes the basic component. Further, the aliasing component can be represented by a power spectrum at a position of the frequency fj=256 and 384.

Further, for example, when abnormality occurs in any one of the three measuring machines 6, the variation of the characteristic values can be represented by a power spectrum in which the number of measuring devices is 3 and the position of the frequency fj=341 becomes the basic component. In this case, however, the aliasing component becomes the double (fj=682) and the triple (fj=1023) of the frequency fj=341, and thus the cycle is equal to or less then 2. For this reason, it is impossible to distinguish the difference in frequency according to a sampling theorem. As a result, a single power spectrum appears only at a position of the frequency fj=341.

Moreover, in general, it is substantially impossible that time series data on the basis of the measured characteristic values has a regular sine curve shown in FIG. 18A or an impulse shape shown in FIG. 19A. For this reason, as shown in FIG. 24, the power spectrum of the basis component becomes a peak value, and the aliasing component tends to become a waveform which the size of the power spectrum is gradually decreased. Further, actually, according to other reasons than the reasons caused by the device, the variation of the measured characteristic values occurs, and thus white noise occurs, other than the frequency component corresponding to each device.

The frequency translating unit 113 calculates frequency data shown in FIG. 24 and transmits calculated frequency data to the frequency masking unit 114. Then, the frequency masking unit 114 divides frequency data (mask component) indicating the frequency component corresponding to a specified device and data other than frequency data on the basis of frequency data received from the frequency translating unit 113 (S123).

That is, the frequency masking unit 114 receives the actual number of devices in the operation state used for the production process for the individual devices from the adjustment control unit 115, together with the identification information of the individual devices (the measuring machine 6, the processing board 3, and the second processing machine 5). Then, the frequency masking unit 114 divides frequency data in the vicinity of the basis component corresponding to each device and the aliasing component, that is, frequency data, excluding the mask component, on the basis of the received information. That is, the frequency masking unit 114 performs the division of frequency data on the frequency components corresponding to the processing board 3, the second processing machine 5, and the measuring machine 6.

Moreover, when the division of frequency data is performed, the characteristic value measured by the measuring machine 6 includes the measurement error, and thus frequency data of a frequency according to the number of devices and a frequency of the integer multiple thereof, and frequency data in its periphery are divided as the mask component together.

Here, if a display instruction of expectation of a shift state of the characteristic value after the improvement is received through the input unit 121 ('YES' in S124), the frequency masking unit 114 transmits frequency data other than the divided mask component to the inverse-translating unit 119.

That is, when receiving the display instruction of state expectation after the improvement, the input unit 121 notifies the adjustment control unit 115 of the instruction. When receiving the notification from the input unit 121, the adjustment control unit 115 requests the frequency masking unit 114 to transmit the integral value of the power spectrums corresponding to the frequencies of the individual devices.

On the other hand, according to the request from the adjustment control unit 115, the frequency masking unit 114 transmits the integral value of the power spectrums of the individual devices to the adjustment control unit 115. Then, the adjustment control unit 115 calculates the standard deviation from the integral value of the power spectrums of the individual devices and specifies the device having the maximum standard deviation as the device to be adjusted. Next, information indicating the device specified as the device to be adjusted is transmitted to the frequency masking unit 114.

In the present embodiment, as shown in FIG. 24, since the power spectrum occurring in the frequency corresponding to the second processing machine 5 is larger than the power spectrum occurring in the frequency corresponding to another device, the adjustment control unit 115 specifies the second processing machine 5 as the device to be adjusted.

Then, the adjustment control unit 115 transmits information indicating the second processing machine 5 to the frequency masking unit 114.

When receiving the information indicating the device to be adjusted from the adjustment control unit 115, the frequency masking unit 114 transmits, to the inverse-translating unit 119, frequency data, excluding the mask component corresponding to the device to be adjusted, that is, frequency data in which the mask component corresponding to the second processing machine 5 is 'zero'.

Figure 25A:
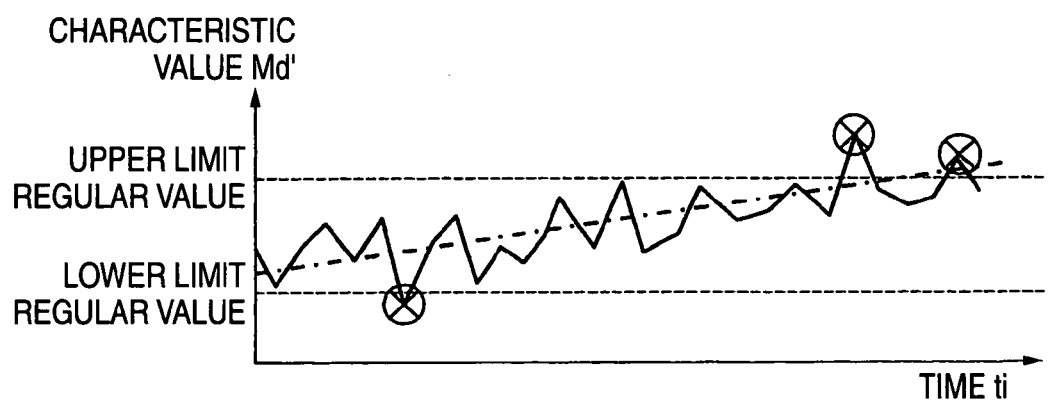
FIG. 25A shows an example of time series data of the characteristic values obtained from frequency data in which only mask component is removed according to the present embodiment.

On the other hand, the inverse-translating unit 119 inverse-translates frequency data received from the frequency masking unit 114 and creates time series data on the basis of frequency data other than the mask component shown in FIG. 25A (S125). Then, the inverse-translating unit 119 transmits created time series data, for example, shown in FIG. 25A to the display control unit 120, and the display control unit 120 displays time series data.

Moreover, in time series data shown in FIG. 25A, it can be understood that the number of characteristic values out of the regular range is decreased, as compared with time series data shown in FIG. 23A. However, in time series data shown in FIG. 25A, a graph further rises due to an influence of increase tendency of a low frequency component.

Figure 25B:
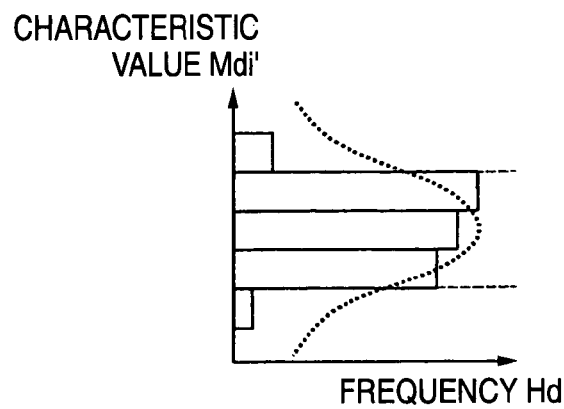
FIG. 25B is a histogram showing the variation rating of the characteristic values.

For this reason, when time series data shown in FIG. 25A is represented by a histogram, a shape shown in FIG. 25B is obtained, and is further close to the rectangular shape, as compared with the case of FIG. 23B in which time series data of FIG. 23A is represented by the histogram. Further, in the variation of the characteristic values obtained on the basis of time series data shown in FIG. 23A, the number of characteristic values out of the regular range is not different from the number of characteristic values out of the regular range obtained on the basis of time series data shown in FIG. 25A so much.

Accordingly, in order to perform accurate improvement expectation, the display control unit 120 calculates and outputs the number of characteristic values out of the regular range from time series data of FIG. 23A with reference to the regular range information 131 stored in the information storing unit 112. Therefore, the adjusting apparatus 307 according to the present embodiment can accurately grasp the number of abnormal characteristic values before the adjustment of the device.

Further, the display control unit 120 calculates and outputs the number of characteristic values out of the regular range from time series data shown in FIG. 25A, in which the non-mask component is subjected to the reverse FFT, with reference to the regular range information 131. For this reason, the adjusting apparatus according to the present embodiment can grasp the number of abnormal characteristic values to be expected after the device adjustment and examine the change of the number of abnormal characteristic values before and after the device adjustment.

As such, in the adjusting apparatus 307 according to the present embodiment, time series data on the basis of frequency data (non-mask component) other than the mask component can be displayed on the display control unit 120. Further, when the device specified as the reason for abnormality is adjusted, the adjusting apparatus 307 can calculate and display the number of characteristic values out of the regular range on the basis of the time series data on the basis of frequency data of the non-mask component and the regular range information 131.

For this reason, by adjusting the device specified as the reason for abnormality, the user can grasp how much the number of characteristic values out of the regular range is decreased. That is, in an example shown in FIG. 25, when it is assumed that the second processing machine 5 as the reason for abnormality, it can be understood that the number of characteristic values out of the regular range is reduced from seven initially to three. Therefore, it can be understood that, by adjusting the second processing machine 5, the user can perform the processing of the articles 9 with higher precision.

As such, in the adjusting apparatus 307 according to the present embodiment, before the adjustment of the device specified as the reason for abnormality is performed, it can be seen that, by adjusting the device, how much the number of characteristic values out of the regular range is decreased. For this reason, in view of productivity of the articles 9, the user can easily judge whether or not the adjustment of the device specified as the reason for abnormality is performed. Further, even when the device is adjusted, when it is judged that the improvement is not significantly made, the user can determine so as not to perform the adjustment.

Further, in the adjusting apparatus 307, the configuration is disclosed in which time series data generated through the inverse-translation of frequency data of the non-mask component, excluding the mask component, corresponding to the device specified as the device to be adjusted is displayed. Alternatively, in the adjusting apparatus 307, the configuration may be provided in which the number of values of time series data out of the regular range is displayed on the basis of the time series data generated through the inverse-translation of frequency data of the non-mask component and the regular range information 131.

However, the adjusting apparatus 307 may have the configuration in which the standard deviation on the basis of the values of time series data through the inverse-translation of frequency data of the non-mask component is displayed, instead of the number of values of time series data out of the regular range.

As such, in a case in which the standard deviation is displayed, in the adjusting apparatus 307, the variation of the characteristic values when it is assumed that the adjusting apparatus 307 specified as the reason for abnormality is adjusted can be displayed.

Further, in the adjusting apparatus 307, the configuration is disclosed in which time series data generated through the inverse-translation of frequency data of the non-mask component, excluding the mask component corresponding to the device specified as the device to be adjusted is displayed. To the contrary, time series data, for example, shown in FIG. 26, may be generated through the inverse-translation of only frequency data of the mask component and may be displayed.

Figure 26:
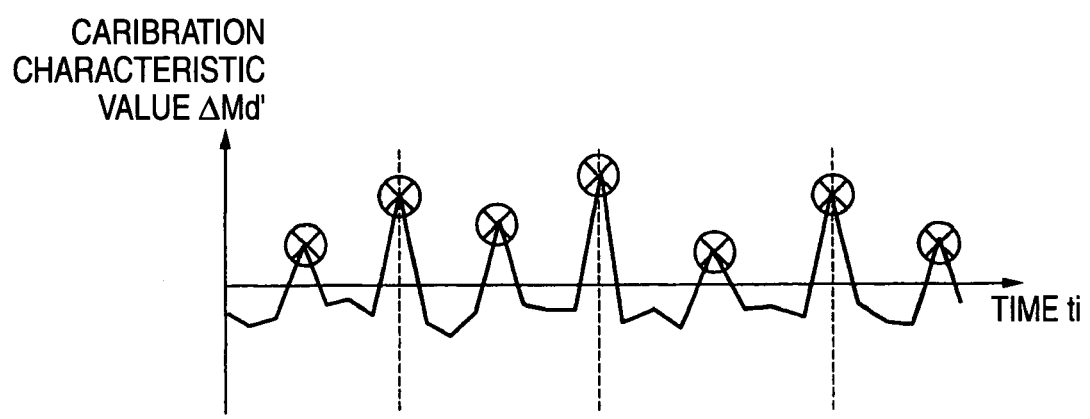
FIG. 26 is a diagram showing an example of time series data of the characteristic values obtained from frequency data of the mask component according to the present embodiment.

Moreover, in FIG. 26, a horizontal axis is the time axis, and a vertical axis is a calibrated characteristic value. Moreover, the calibrated characteristic value shows the shift of the characteristic value from the ideal value in the regular range. In FIG. 26, only a component in a vicinity of a frequency according to the number of devices in the operation state specified as the device to be adjusted is inverse-translated into time series data.

As described above, when the adjusting apparatus 307 displays time series data of the mask component corresponding to the device specified as the device to be adjusted, the user can visually grasp the shift of the characteristic value caused by abnormality of the device to be adjusted. That is, in case of FIG. 26, the significant shift occurs in the characteristic value by one per eight and the shift also occurs at a ratio of one to four. From this, it can be seen that abnormality occurs in at least one of the eight second processing machines 5. Further, since the change also occurs at the ratio of one to four, it can be sufficiently considered that abnormality is likely to occur in two of the eight second processing machines 5.

As described above, by outputting data generated by the inverse-translation of only frequency data of the mask component, the administrator of the manufacturing line system 100 can specify the device having abnormality. That is, the manufacturing line system 100 according to the present embodiment can represent the mode of the shift of each device with high precision. For this reason, in the manufacturing line system 100, the administrator can visually represent the reason for the shift occurring in the characteristic value.

Further, the adjusting apparatus 307 may display time series data of mask components corresponding to other devices as well as the device specified as the device to be adjusted by the adjustment control unit 115.

As described above, when time series data on the basis of the mask components of the individual components are displayed, the user can easily specify the device, which the reason for the variation of the characteristic values. Then, when the device specified as the device to be adjusted needs to be notified, the user inputs the notification through the input unit 121. Moreover, as such, when the device as the device to be adjusted is specified by the used, the specification processing of the device to be adjusted by the adjustment control unit 115 can be omitted. For this reason, the configuration of the adjustment control unit 115 can be further simplified.

(Adjustment Processing of Device)

Figure 27:
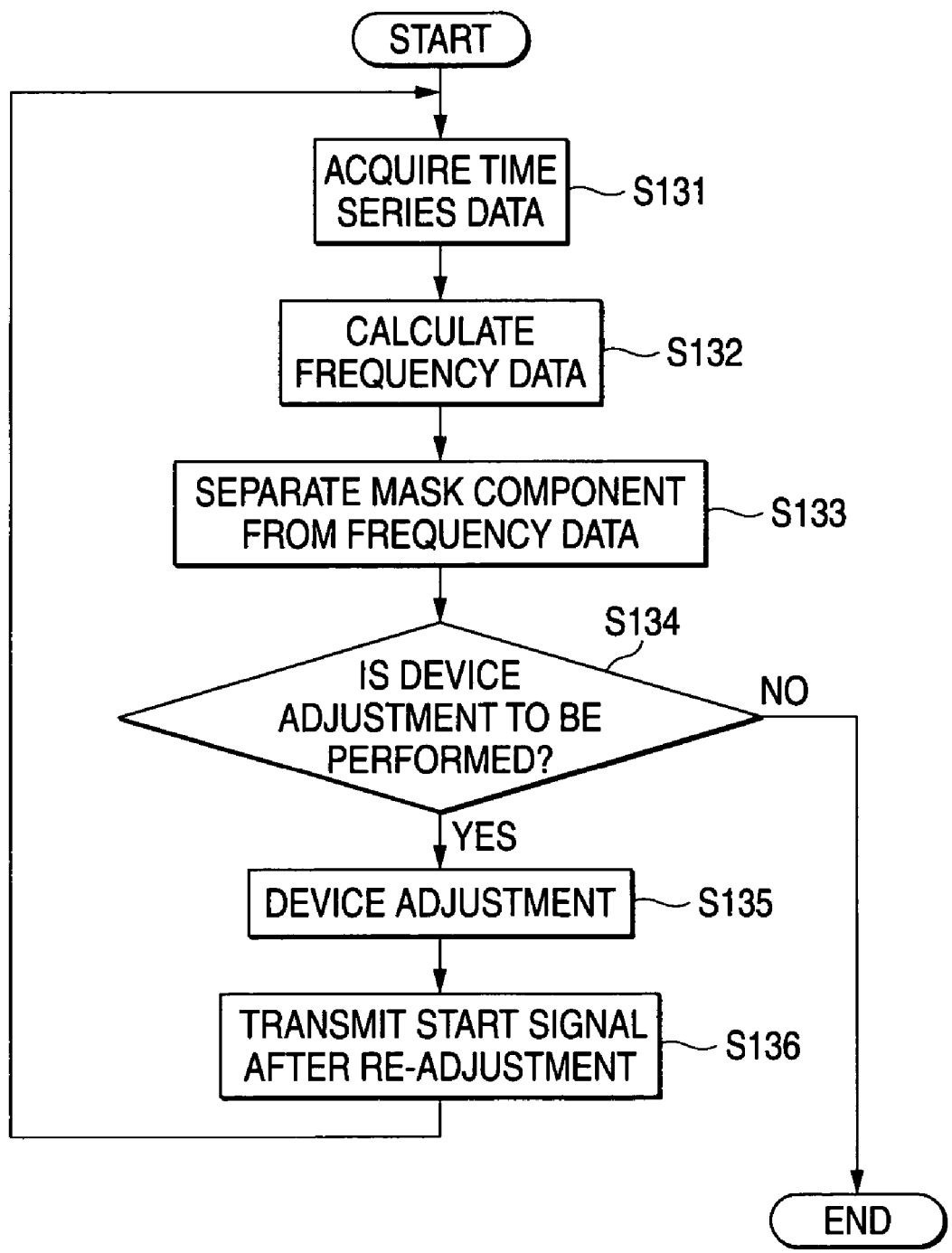
FIG. 27 is a flowchart showing a flow of an adjustment processing of a device in the adjusting apparatus according to the present embodiment.

Next, the adjustment processing of the device specified as the reason for abnormality by the adjusting apparatus according to the present embodiment will be described with reference to FIG. 27.

Figure 22:
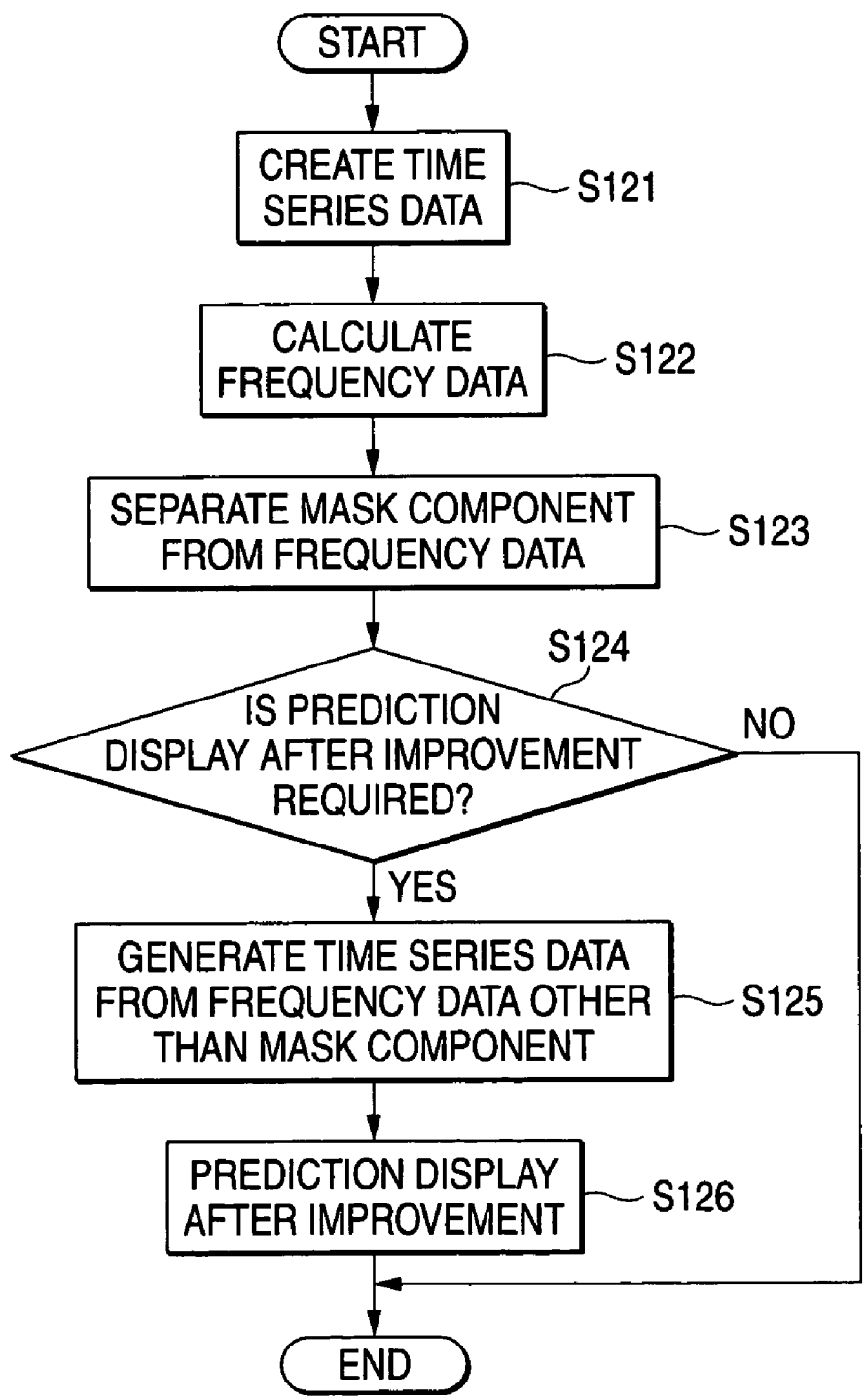
FIG. 22 is a flowchart of a flow of an improvement expectation processing in the adjusting apparatus according to the present embodiment.

Moreover, the processing of acquiring time series data, calculating frequency data from time series data, and dividing frequency data into the mask component and others (in FIG. 27, the step S131 to the step S133) is the same as that of the step s21 to the step S123 of FIG. 22, and thus the descriptions thereof will be omitted.

In the step S134, if the input unit 121 receives the instruction of a purport of adjusting the device ('YES' in S134), the adjustment control unit 115 instructs the measuring-machine setting unit 116, the processing-machine setting unit 117, and the gate setting unit 118 to perform the adjustment of the device specified as the device to be adjusted. Then, according to the instruction from the adjustment control unit 115, the measuring-machine setting unit 116, the processing-machine setting unit 117, or the gate setting unit 118 performs the adjustment of the device (S135).

That is, when receiving the execution instruction of the adjustment processing of the device, the input unit 121 notifies the adjustment control unit 115 of the instruction when receiving the instruction, the adjustment control unit 115 requests the frequency masking unit 114 to transmit the integral value of the power spectrums of the frequency corresponding to each device.

On the other hand, the frequency masking unit 114 transmits the integral value of the power spectrums of the frequency corresponding to each device according to the request from the adjustment control unit 115. Then, the adjustment control unit 115 calculates the standard deviation from the integral value of the power spectrums of the individual devices and specifies the device having the maximum standard deviation as the device to be adjusted.

Here, it is assumed that the adjustment control unit 115 specifies the second processing machine 5 as the device to be adjusted. In this case, the adjustment control unit 115 instructs the processing-machine setting unit 117 to turn off the operation of one of the second processing machines 5a to 5h.

Figure 29:
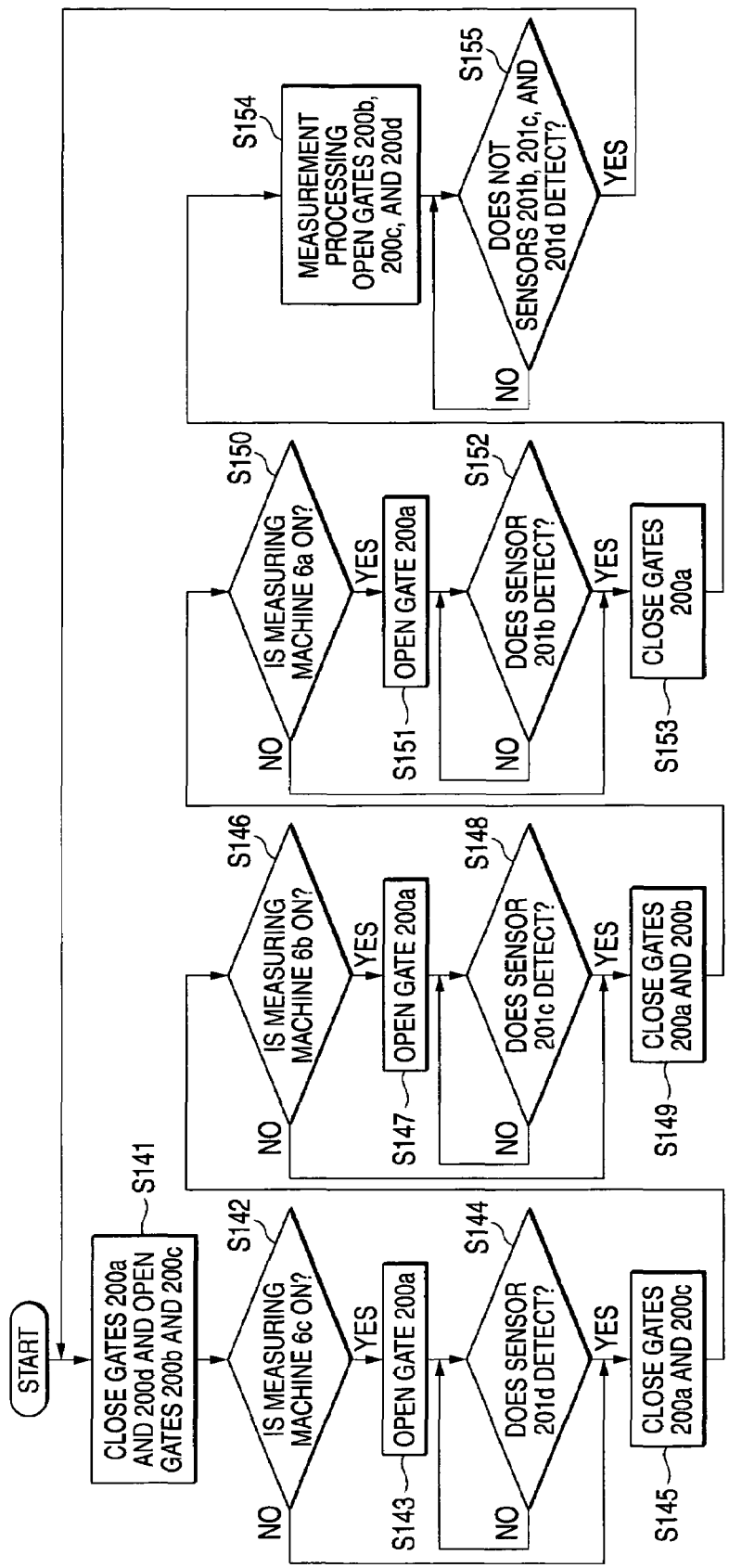
FIG. 29 is a flowchart showing a sequence of positioning of the article with respect to the measuring device in the manufacturing line system according to the present embodiment.

Further, the adjustment control unit 115 controls the transfer belt 8 such that the article 9 is not disposed to face the second processing machine 5 in the powered-off state. Moreover, as for the control of the transfer belt 8, for example, the transfer speed of the article 9 by the transfer belt 8 is changed, or a plurality of gates shown in FIG. 29 are provided between the turntable 4 and the second processing machine and the open/close states of the gates are controlled. That is, as described above, the open/close of the gate is controlled by use of the detection result of the sensor.

As described above, if any one of the second processing machines 5a to 5h is set to be powered-off, and the number of second processing machines 5 in the operation state is changed, the processing-machine setting unit 117 transmits the start signal to the data collecting unit 111 while being delayed from the setting change completion time by the processing-machine setting unit 117 by the delay time 130, with reference to the delay time 130 stored in the information storing unit 121 (S136).

When receiving the start signal from the processing-machine setting unit 117, the data collecting unit 111 returns to the step S131 so as to acquire a predetermined number of characteristic values measured by the measuring machines 6 again and to create time series data. Then, the processing from the step S131 to the step S133 is repeated. Then, the judgment on whether or not to perform the adjustment of the device in the step S134 from second times is performed by the adjustment control unit 115 as follows.

That is, from frequency data obtained through the frequency translation of time series data created on the basis of the characteristic values obtained after the device adjustment, the adjustment control unit 115 receives, from the frequency masking unit 114, the integral value of the power spectrums corresponding to the second processing machine 5 specified as the device to be adjusted. Then, on the basis of the received integral value of the power spectrums, the adjustment control unit 115 calculated the standard deviation of the second processing machine 5 specified as the device to be adjusted. Then, the adjustment control unit 115 judges whether or not the size of the calculated standard deviation is equal to or less than the predetermined value. Moreover, the predetermined value may be given from the user through the input unit 121 or may be stored in the information storing unit 121 in advance.

Then, when it is judged that the size of the standard deviation is equal to or more then the predetermined value, the adjustment control unit 115 judges that the device adjustment is required and progresses to the step S135. Then, the adjustment control unit 115 instructs the processing-machine setting unit 117 to power on the second processing machine 5 in the previously powered-off state and to power off a separate second processing machine 5. Then, according to the instruction from the adjustment control unit 115, the processing-machine setting unit 117 powers on the second processing machine 5 in the previously powered-off state and powers off the separate second processing machine 5 from the second processing machine 5.

Further, at this time, the adjustment control unit 115 controls the transfer belt 8 such that the transferred article 9 is not disposed to face the second processing machine in the powered-off state.

Then, the process progresses to the step S136, and the processing-machine setting unit 117 transmits the start signal to the data collecting unit 111 again while being delayed from the setting change completion time by the processing-machine setting unit 117 by the interval of the delay time 130, with reference to the delay time 130 stored in the information storing unit 112. Further, the processing from the step S131 is repeated until the adjustment control unit 115 judges in the step S134 that the size of the standard deviation is equal to or less than the regular value.

Moreover, in the above description, a case in which the device to be adjusted is the second processing machine 5 is described, but, the same processing is performed when the device to be adjusted is the processing board 3 or the measuring machine 6. Further, when the device to be adjusted is the processing board 3, the change of a use state of the processing board 3 can be implemented by controlling the open/close of the gate 2 according to the instruction from the gate setting unit 118, like the above-described number-of-devices adjustment processing.

That is, in order to specify an arbitrary processing board 3, in the above-described manufacturing line system 100, identification tag numbers (ID numbers) are allocated to the individual processing boards 3a to 3p or the deviation amount of the rotation of the turntable 4 is managed by use of a rotary encoder.

Then, while monitoring the position of the processing board 3 with the ID numbers allocated to the individual processing boards 3a to 3p, the adjusting apparatus 307 connects the open/close of the gate 2 to the rotation of the turntable 4. For example, in order that the article 9 is not housed in the processing board 3a with the ID number (1) allocated thereto, the gate 2 is controlled to close at the timing at which the article 9 transferred by the transfer belt 8 is housed in the processing board 3a. As such, by controlling the turntable 4 and the gate 2, it can be controlled such that the article 9 is not housed in the processing board 3 in a non-operation state.

Moreover, as described above, by limiting housing of the article 9 in the processing board 3, it can be adjusted such that the variation of the characteristic values is reduced. Moreover, when the number of processing boards 3 in the operation state is changed in such a manner, it can be implemented only by controlling the open/close of the gate 2 and the rotation of the turntable 4. Therefore, in the manufacturing line system 100, the adjustment can be easily performed such that the variation of the characteristic values is reduced.

Further, when the device to be adjusted is the measuring machine 6, the change of the use state of the measuring machine 6 can be implemented by controlling the open/close of the gate 200 according to an ON/OFF instruction of power from the measuring-machine setting unit 116 and the detection of the gate 200 and the sensor 201.

Moreover, when the device to be adjusted is the measuring machine 6, the adjusting apparatus 307 has the configuration in which the variation of the characteristic values is reduced to fall within the regular range with the ON/OFF control of power of the measuring machine 6. However, by controlling open/close timing of the gate 200 and by changing the measurement position of the article 9, for example, by causing the article 9 to be not disposed at the measurement position of a specified measuring machine 6, the adjustment may be performed such that the variation of the characteristic values is reduced.

As described above, the adjusting apparatus 307 according to the present embodiment controls such that the device having abnormality is not used for the device as the device to be adjusted by the ON/OFF control of power of the second processing machine 5 and the measuring device 6 and the open/close control of the gate 2. Then, the adjusting apparatus 307 controls the device having abnormality, thereby reducing the variation occurring in the characteristic values of the processed articles 9.

That is, the adjusting apparatus 307 according to the present embodiment specifies the device becoming the subject that generates the characteristic value significantly shifted from the regular range and changes the operation state of the corresponding device, so that the shift of the characteristic value from the regular range value can be reduced. For this reason, the adjusting apparatus 307 can improve the quality of an article 9 to be processed after processing.

Further, as described above, the adjusting apparatus does not require the structure in which the specific adjusting unit is provided for each of the second processing machine 5, the processing board 5, and the measuring machine 6 and the minute adjustment is repeatedly performed, and performs simple control such as switching on and switching off of the power supply of the adjusting apparatus so as to reduce the shift of the characteristic value from the regular range value.

Further, the adjusting apparatus 307 according to the present embodiment may have the structure in which the adjustment processing of the apparatus described above is performed by associating it with the improvement prediction processing. In a case in which the adjustment processing of the apparatus described above is performed by associating it with the improvement prediction processing, a step S134 is executed after the step S126. In addition, if a step S136 illustrated in FIG. 27 is executed, the process returns to the step S121 illustrated in FIG. 22.

Further, in the step S134, if the shift of the characteristic value due to the abnormality of the device specified as the device to be adjusted (a degree of the standard deviation of the characteristic values) is equal to or less then the predetermined value, the adjustment processing of the device is continuously performed until the adjustment control unit determines it.

However, examples of the completion condition of the adjustment processing of the apparatus may include a structure in which the maximum value of the power spectrum of the frequency corresponding to the device specified as the device to be adjusted is used. In addition, the structure in which it is determined using the maximum value of the power spectrum whether the adjustment processing is necessary or not is very advantageous because of the following reason. That is, for example, in devices other than the device which has become the adjustment subject, even when a factor of the shift of the other characteristic values is generated, it does not affect the shift of the other characteristic value in the structure in which the determination is performed using the maximum value of the power spectrum.

Further, in the adjusting apparatus 307 according to the present embodiment, in 'the improvement prediction processing' and 'the adjusting processing of the device', the adjustment control unit 115 calculates the standard deviation from the integral value of the power spectrum of the frequency corresponding to each device and specifies the device having the largest standard deviation as the subject to be adjusted.

However, the method of specifying the subject to be adjusted is not limited thereto, but may have the following structure.

The adjustment control unit 115 receives the time series data of the characteristic value created by the data collection unit 111 and calculates the standard deviation on the basis of the received time series data. The adjustment control unit 115 may specify the device becoming the abnormality factor on the basis of the shift of the standard deviation calculated in this way.

In the case of the structure in which the device becoming the abnormality factor is specified, the adjustment processing of the device is completed according to the following condition. That is, in the device specified as the abnormality factor, when the operated device is changed and the standard deviation based on the time series data received from the data collection unit 111 is equal to or greater than the predetermined value, the adjustment control unit 115 completes the adjustment processing of the device. According to this structure, since it is not necessary to perform the FFT with respect to the time series data created by the data collection unit 11, it is possible to reduce the amount of operation in the adjusting apparatus 307.

Alternatively, time series data in which mask components of frequencies corresponding to the number of machines to be operated in each apparatus are inverted FFTs may be received from the inverse-translating unit 119, and an apparatus in which the adjustment control unit 115 has a trouble may be specified.

As such, in the case of the structure in which an apparatus having a trouble is specified on the basis of the inverted-FFT time series data, the adjustment process of the apparatus is completed under the following conditions. That is, when a variation in the characteristic value of the inverted-FFT time series data is smaller than a predetermined value, or when the number of characteristic values larger than a predetermined value is below a predetermined number, the adjustment process of the device is completed.

In the manufacture line system 100 according to this embodiment, in the 'number-of-devices adjusting process' and the 'adjustment process of the device', the adjusting apparatus 307 changes the number of devices used for the manufacturing process. Therefore, information indicating the usage state of the device after change may be displayed by the display control unit 120. When the information indicating the usage state of the device is displayed, the adjustment control unit 115 acquires the information indicating the usage state of the device from the gate setting unit 118, the processing-machine setting unit 117, and the measuring-machine setting unit 116, and the acquired information is transmitted to the display control unit 120. The display control unit 120 performs display on the basis of the received information.

The user can acquire useful information from a maintaining process, such as which device is turned on or off and which device is not used, by displaying the information indicating the usage state of the device.

Further, each device is provided with a light-emitting portion (not shown) using, for example, an LED (light emitting diode), and the light emitting portion may be turned on to display that the device is in use. As such, the usage state of the device can be visually displayed, and thus it is possible to effectively perform the maintaining process on devices included in the manufacture line system 100 according to this embodiment.

In the manufacture line system 100 according to this embodiment, the turn table 4 is provided to aggregate mounting places of devices, such as the processing board 3 and the second processing machine 4. Therefore, the turn table 4 may be used to change a direction in which the processing target 9 is carried in the manufacture line system 100. In this case, in the manufacture line system 100, a transferring path is further provided after the turn table 4.

Further, the manufacturing method of the adjusting apparatus 307 according to this embodiment includes the following steps. That is, the manufacturing method of the adjusting apparatus 307 according to this embodiment is a method of controlling the adjusting apparatus 307 provided in a manufacture line system (production producing system) including processing boards 3a to 3p (production producing devices) and second processing machines 5a to 5h that perform on a manufacturing process (production process) on an article to be processed (an article to be produced), and a measuring machine 6 that measures characteristic values indicating the quality of the article processed (produced) by the second processing machines 5a to 5h and the processing boards 3a to 3p.

Therefore, the manufacturing method of the adjusting apparatus 307 according to this embodiment includes: a step of acquiring characteristic values from the measuring machine 6; when the transfer sequence of processing targets corresponding to the acquired characteristic values is considered as a time axis, a step of creating frequency data by frequency-translating time series data indicating the change of the characteristic value according to the time axis; a step of specifying a device to be adjusted, on the basis of the created frequency data; and a step of setting the second processing machines 5a to 5h and the processing boards 3a to 3p to be operated, among the second processing machines 5a to 5h and the processing boards 3a to 3p corresponding to each manufacturing process.

According to the method of controlling the adjusting apparatus 307, in the step of setting the second processing machines 5a to 5h and the processing boards 3a to 3p to be operated, if the number of the operated second processing machines 5a to 5h and the number of the processing boards 3a to 3p are respectively set to m and n (m<n), when n becomes a multiple of m, a value of n and/or a value of m are controlled so as to be changed.

As described above, according to the method of controlling the adjusting apparatus 307 according to the present embodiment, in the step of setting the second processing machines 5a to 5h and the processing boards 3a to 3p, which are operated, if the number of the operated second processing machines 5a to 5h is set to n and the number of the processing boards 3a to 3p is set to m, when n becomes a multiple of m, a value of n and/or a value of m can be controlled so as to be changed. That is, the number of the operated second processing machines 5a to 5h and the number of the processing boards 3a to 3p can be adjusted and controlled such that any one of them does not become a multiple of the other.

Accordingly, in a case in which cyclicity of the change of the characteristic value is analyzed by use of frequency data obtained by translating time series data through a fast Fourier translation (FFT) or the like, it is possible to resolve the problems in that frequency components in frequency data overlap each other and the device to be adjusted cannot be specified. Accordingly, according to the method of controlling the adjusting apparatus 307 according to the present embodiment, the device to be adjusted can be specified with more accuracy.

Further, the method of controlling the adjusting apparatus 307 according to the present embodiment includes the following processes.

That is, the method of controlling the adjusting apparatus 307 according to the present embodiment is a method of controlling the adjusting apparatus 307 included in the manufacturing line system 100. Here, the manufacturing line system 100 includes the second processing machines 5a to 5h or the processing boards 3a to 3p that execute processing (production process) on an article to be processed (article to be produced) and the measuring machines 6a to 6c that measure a characteristic value indicating a quality of the article processed by the second processing machines 5a to 5h or the processing boards 3a to 3p.

In addition, the method of controlling the adjusting apparatus 307 includes a step of receiving the characteristic values from the measuring machines 6a to 6c, a step of calculating frequency data by setting a transfer sequence number of the articles corresponding to the received characteristic values as a time axis and subjecting time series data indicating the change of the characteristic value according to the time axis to frequency translation; a step of specifying a device to be adjusted on the basis of the calculated frequency data; a step of setting the operated second processing machine 5 or the operated processing board 3 among the second processing machines 5a to 5h or the processing boards 3a to 3p (production processing devices), and a step of setting the operated measuring machine 6.

In addition, according to the method of controlling the adjusting apparatus 307, in the step of setting the operated second processing machine 5 or the operated processing board 3 and in the step of setting the operated measuring machine 6, if the number of the operated second processing machine 5 or the number of the operated processing board 3 and the number of the operated measuring machine 6 are respectively set to m and n (m<n), when n becomes a multiple of m, a value of n and/or a value of m are controlled so as to be changed.

As described above, according to the method of controlling the adjusting apparatus 307 according to the present embodiment, in the step of setting the operated second processing machine 5 or the operated processing board 3 and in the step of setting the operated measuring machine 6, if the number n of the operated second processing machine 5 or the operated processing board 3 becomes a multiple of the number m of the operated measuring machine 6, a value or n and/or a value of m are controlled so as to be changed. To the contrary, if the number m of the operated measuring machine 6 becomes a multiple of the number n of the operated second processing machine 5 or the operated processing board 3, a value of n and/or a value of m can be controlled so as to be changed.

That is, the number of the operated second processing machine 5 and the operated processing board 3 or the number of the operated measuring machine can be adjusted and controlled such that any one of them does not become a multiple of the other.

Accordingly, in a case in which cyclicity of the change of the characteristic value is analyzed by use of the frequency data obtained by translating the time series data through a fast Fourier translation (FFT) or the like, it is possible to resolve the problems in that frequency components in frequency data overlap each other and the device to be adjusted cannot be specified. As a result, according to the method of controlling the adjusting apparatus according to the present embodiment, the device to be adjusted can be specified with more accuracy.

Further, the method of controlling the adjusting apparatus 307 according to the present embodiment includes the following processes. That is, the method of controlling the adjusting apparatus 307 according to the present embodiment is a method of controlling the adjusting apparatus 307 included in the manufacturing line system (production system). Here, the manufacturing line system includes the second processing machines 5a to 5h and the processing boards 3a to 3p (production processing device) that execute processing (production process) on an article to be processed (article to be produced) and the measuring machine 6 that measure characteristic values indicating a quality of the article processed (produced) by the second processing machines 5a to 5h or the processing boards 3a to 3p.

In addition, the method of controlling the adjusting apparatus 307 according to the present embodiment includes a step of receiving the characteristic values from the measuring machine 6, a step of calculating frequency data by setting a transfer sequence number of the articles corresponding to the received characteristic values as a time axis and subjecting time series data indicating the change of the characteristic values according to the time axis to frequency translation; a step of extracting a power spectrum of a frequency according to the number of each of the second processing machine 5 and the processing board to be operated on the basis of the calculated frequency data; a step of specifying the device to be adjusted on the basis of the power spectrum of the frequency according to the number of each of the second processing machine 5 and the processing board 3 extracted by the extracting unit; and a step of setting the operated second processing machine 5 or the operated processing board 3 among the second processing machine 5 and the processing board 3 corresponding to the processing, and a step of setting the operated measuring machine 6.

In addition, according to the method of controlling the adjusting apparatus 307, stopped is sequentially the operation of any one of the second processing machines 5a to 5h and any one of the processing boards 3a to 3p (second production processing devices) until the integral value of the power spectrum of the frequency corresponding to the second processing machine 5 (first production processing device) or the processing board 3 (second production processing device) specified by the specifying unit as the device to be adjusted is equal to or less than a predetermined value.

As described above, according to the method of controlling the adjusting apparatus 307 according to the present embodiment, it is possible to sequentially stop the operation of any one of the second processing machines 5a to 5h and any one of the processing boards 3a to 3p until the integral value of the power spectrum of the frequency corresponding to the second processing machines 5a to 5h (first production processing devices) or the processing boards 3a to 3p (second production processing devices) specified by the specifying unit as the device to be adjusted is equal to or less than a predetermined value.

That is, according to the method of controlling the adjusting apparatus 307 according to the present embodiment, in the second processing machines 5a to 5h or the processing boards 3a to 3p specified by the specifying unit as the device to be adjusted, the second processing machine 5 or the processing board 3 can be specified with high precision in which an abnormality occurs, so that it is possible to stop the operation of the abnormal device.

For this reason, according to the method of controlling the adjusting apparatus 307, the deviation of a defined value of the characteristic value can be adjusted and reduced without repeating the minute adjustment and the specific adjusting unit.

Further, the adjustment device 7 according to the present embodiment can have the following steps. That is, the method of controlling the adjusting apparatus 307 according to the present embodiment is a method of controlling the adjusting apparatus 307 included in the manufacturing line system 100. Here, the manufacturing line system 100 includes the second processing machines 5a to 5h or the processing boards 3a to 3p that execute processing on an article to be processed and the measuring machines 6a to 6c that measure a characteristic value indicating a quality of the article processed by the second processing machines 5a to 5h or the processing boards 3a to 3p.

A method of controlling the adjusting apparatus 307 includes a step of acquiring characteristic values from the measuring machine 6; when the transfer sequence of processing targets corresponding to the acquired characteristic values is considered as a time axis, a step of creating frequency data by frequency-translating time series data indicating the change of the characteristic value according to the time axis; a step of extracting a power spectrum of a frequency according to the number of machines, such as the measuring machine 6 and the second processing machine 5 or the processing board 2 to be operated, on the basis of the calculated frequency data; a step of specifying a device to be adjusted, on the basis of the power spectrum of the frequency according to the number of machines such as the measuring machine 6 and the second processing machine 5 or the processing board 2 to be operated, which is extracted by the extracting unit; and a step of setting the second processing machine 5 or the processing board 2 to be operated; and a step of setting the measuring machine 6 to be operated.

In the control method of the adjusting apparatus 307, in the step of setting the second processing machine 5 or the processing board 2 or the step of setting the measuring machine 6, until an integral value of the frequency power spectrum corresponding to the second processing machine 5, the processing board 2, or the measuring machine 6, which is specified as a target to be adjusted, is smaller than a predetermined value, control is performed such that the operation of one of the second processing machines 5a to 5h or the processing boards 3a to 3p or one of the measuring machines 6a to 6c sequentially stops.

As described above, according to the control method of the adjusting apparatus 307 according to this embodiment, it is possible to sequentially stops the operation of one of the second processing machines 5a to 5h or the processing boards 3a to 3p or one of the measuring machines 6a to 6c, until an integral value of the frequency power spectrum corresponding to the second processing machine 5, the processing board 2, or the measuring machine 6, which is specified as a target to be adjusted, is smaller than a predetermined value.

That is, in the control method of the adjusting apparatus 307 according to this embodiment, it is possible to accurately specify a machine having a trouble from the second processing machine 5, the processing board 2, and the measuring machine 6 and to stop the operation thereof.

Further, the control method of the adjusting apparatus 307 makes it possible to reduce a difference between the characteristic value and a predetermined value, without repeatedly performing minute adjustment or providing a special adjusting unit.

The adjusting machine 7 of this embodiment has the following characteristic structure.

Finally, the respective blocks of the adjusting machine 7, such as the frequency translating unit 113, the frequency masking unit 114, the adjustment control unit 115, the measuring-machine setting unit 116, the processing-machine setting unit 117, the gate setting unit 118, the inverse-translating unit 119, the display control unit 120, and the input unit 121, may be constituted by hardware logics, and they may be realized by software using a CPU.

That is, the adjusting apparatus 307 includes, for example, a CPU (central processing unit) which executes instructions of a control program for performing each function, a ROM (read only memory) for storing the program, a RAM (random access memory) for developing the program, and a storage unit (storage medium), such as a memory for storing the program and various data. An article of the invention can be achieved by supplying, to the adjusting apparatus 307, a storage medium in which a program code (an executable program, an intermediate code program, and a source program) of the control program for the adjusting apparatus 307, which is software for realizing the functions, is stored such that the computer can read it, and by allowing the computer (or a CPU or an MCU) to read out the program stored in the storage medium and to execute it.

The storage medium includes, for example, a tape-type medium, such as a magnetic tape or a cassette tape, a disc-type medium including a magnetic disc, such as a floppy (a registered trademark) disc or a hard disc, and an optical disc, such as CD-ROM/MO/MD/DVD/CD-R, a card-type medium, such as an IC card (including a memory card) or an optical card, and a semiconductor memory, such as a mask ROM, an EPROM, an EEPROM, or a flash ROM.

Further, the adjusting apparatus 307 may be constituted such that it can be connected to a communication network, and the program may be supplied thereto through the communication network. The communication network includes, for example, the Internet, the Intranet, an intranet, an extranet, a LAN, an ISDN, a VAN, a CATV communication network, a virtual private network, telephone lines, a mobile communication network, and a satellite communication network. A transmission medium for constituting the communication network includes, for example, wire lines, such as IEEE1394, USB, power lines, cable TV lines, telephone lines, and ADSL lines, infrared rays, such as XrDA or a remote controller, and wireless lines, such as Bluetooth (a registered trademark), 802.11 Wireless, HDR, a mobile communication network, satellite lines, and a terrestrial digital broadcasting network. In addition, the program may be incorporated into carrier waves and then transmitted in the form of computer data signals.

Moreover, the present invention is not limited to the above-described embodiment, and various changes can be made within the range read on the claims. That is, embodiments which are obtained by incorporating technical units suitably changed within the range read on the claims are also the technical range of the present invention.

The adjusting apparatus 307 according to the present embodiment can judge which device from various kinds of devices has abnormality in the manufacturing line system 100 in which various kinds of a plurality of devices are provided and the articles are processed by any one of various kinds of devices. For t his reason, the present invention can be widely applied to a manufacturing line which performs mass production of various kinds of articles.

It will be apparent to those skilled in the art that various modifications and variations can be made to the described preferred embodiments of the present invention without departing from the spirit or scope of the invention. Thus, it is intended that the present invention cover all modifications and variations of this invention consistent with the scope of the appended claims and their equivalents.

We claim:

1. An adjusting apparatus which receives characteristic values indicating quality of articles produced by one of m production processing devices from one of n measuring devices and specifies a device to be adjusted, where m and n are natural numbers different from each other, the adjusting apparatus comprising:
    a judging unit that, on the basis of the characteristic values received from the measuring device, judges whether or not the produced articles meet regular quality;
    a storage device that stores the characteristic values received from the measuring device in association with a sequence number in which the articles having the characteristic values are produced;
    a cycle detecting unit that, if the judging unit judges that the produced articles do not meet regular quality, on the basis of the characteristic values stored in the storage device, detects cyclicity of the abnormal characteristic value, which is a characteristic value out of a range of characteristic values when the produced article meets regular quality, indicating whether the abnormal characteristic value appears by m cycles or n cycles; and
    a specifying unit that specifies the device to be adjusted on the basis of the detection result by the cycle detecting unit.

2. The adjusting apparatus according to claim 1, further comprising:
    a calculating unit that calculates a statistical feature of the characteristic values associated with cyclicity of the abnormal characteristic value on the basis of the characteristic values stored in the storage device,
    wherein on the basis of the statistical feature calculated by the calculating unit, the cycle detecting unit determines to detect either the m cycles or the n cycles from cyclicity of the abnormal characteristic value to be detected.

3. The adjusting apparatus according to claim 2,
    wherein the characteristic values stored in the storage device are also stored in association with a number allocated to the measuring device which measures the characteristic values,
    the calculating unit has a distribution feature calculating unit that, on the basis of the characteristic values stored in the storage device, divides the range of the characteristic values into predetermined sections and calculates distribution feature information indicating a feature of frequency distribution information of characteristic values included in a range of each section, and
    an individual defective fraction calculating unit that calculates an individual defective fraction, which is the ratio of the abnormal characteristic value with respect to the characteristic values measured by each of the measuring devices.

4. The adjusting apparatus according to claim 3, further comprising:
    a changing unit that, when the production processing device is specified by the specifying unit as the device to be adjusted, changes a set value for defining the operation of the production processing device; and
    a change instructing unit that instructs the changing unit to change the set value so as to cause the frequency distribution information to approximate to frequency distribution information in accordance with the characteristic values of the articles which meet regular quality, wherein the changing unit changes the set value of one of the m production processing devices in accordance with the change instruction by the change instructing unit, wherein the change instructing unit instructs the changing unit to change the set value until frequency distribution information in accordance with a post-change characteristic value of an article produced after the set value is changed by the changing unit approximates to the frequency distribution information in accordance with the characteristic values to be obtained from the produced articles which meet regular quality.

5. The adjusting apparatus according to claim 1, further comprising:

a data collecting unit that, when a transfer sequence number of the articles corresponding to the characteristic values measured by the measuring device is considered as a time axis, creates time series data indicating the change of the characteristic values according to the time axis;

a translation calculating unit that performs frequency translation on time series data created by the data collecting unit so as to calculate frequency data;

a degree-of-variation calculating unit that calculates a change amount of a degree of variation of the characteristic values before and after the adjustment of the device to be adjusted on the basis of a sum of power spectrum values and a power spectrum value in a frequency band corresponding to a specified cycle in which the abnormal characteristic value appears, based on the frequency data calculated by the translation calculating unit, and a value indicating the degree of variation of all the characteristic values; and an output unit which outputs information indicating the change amount of the degree of variation calculated by the degree-of-variation calculating unit.

6. The adjusting apparatus according to claim 1, wherein the storage device also stores variation tolerance information indicating a degree of variation which is judged that the adjustment of the device to be adjusted does not need to be preformed with respect to the characteristic values measured by the measuring device, the adjusting apparatus further comprising:

a data collecting unit that, when a transfer sequence number of the articles corresponding to the characteristic values measured by the measuring device is considered as a time axis, creates time series data indicating the change of the characteristic values according to the time axis;

a translation calculating unit that performs frequency translation on time series data created by the data collecting unit so as to calculate frequency data;

an adjustment executing judging unit that, on the basis of the variation tolerance information stored in the storage device, a value indicating a degree of variation of all the characteristic values measured by the measuring devices, and the sum of power spectrum values based on the frequency data calculated by the translation calculating unit, calculates a threshold value for judging whether or not the device to be adjusted specified by the specifying unit needs to be adjusted, compares the size of a spectrum at a specified frequency, at which the abnormal characteristic value appears based on the frequency data calculated by the translation calculating unit, with the threshold value, and judges whether or not to perform the adjustment of the device specified by the specifying unit as the device to be adjusted.

7. The adjusting apparatus according to claim 1, further comprising:

a data collecting unit that, when a transfer sequence number of the articles corresponding to the characteristic values measured by the measuring device is considered as a time axis, creates time series data indicating the change of the characteristic value according to the time axis;

a translation calculating unit that performs frequency translation on time series data created by the data collecting unit so as to calculate frequency data;

a setting unit that sets at least one production processing device and at least one measuring device in an operation state from among the m production processing devices and the n measuring devices; and a number-of-devices control unit that, when the number of production processing devices in an operation state and the number of measuring devices in an operation state are a and b, respectively, where one of a and b is multiples of the other, controls the setting unit so as to change the number of a and/or the number of b, wherein the specifying unit specifies the production processing device or the measuring device as a device to be adjusted on the basis of frequency data calculated by the translation calculating unit.

8. The adjusting apparatus according to claim 7, wherein the setting unit manages setting information indicating the number of production processing devices in the operation state and the number of measuring devices in the operation state, and the number-of-devices control unit acquires the setting information from the setting unit and controls to change the number of production processing devices in the operation state and/or the number of measuring devices in the operation state on the basis of the acquired setting information.

9. The adjusting apparatus according to claim 7, wherein, when the change of the number of production processing devices or the number of measuring devices is controlled by decreasing the number of devices in the operation state, the number-of-devices control unit controls the change of the number of devices having a larger number of devices in the operation state from among the production processing devices and the measuring devices, and when the change of the number of production processing devices or the number of measuring devices is controlled by increasing the number of devices in the operation state, the number-of-devices control unit controls the change of the number of devices having a smaller number of devices in the operation state from among the production processing devices and the measuring devices.

10. The adjusting apparatus according to claim 7, wherein the data collecting unit receives the characteristic values of the article produced after change measured by the measuring devices while delaying by the amount of time lapse from a point of time, at which the number of the production processing devices in the operation state is changed according to an instruction from the setting unit, until the articles are produced by the production processing device in the operation state after the change and then its characteristic values are measured, and creates time series data on the basis of the characteristic values.

11. The adjusting apparatus according to claim 1, further comprising:
- a data collecting unit that, when a transfer sequence number of the articles corresponding to the characteristic values measured by the measuring device is considered as a time axis, creates time series data indicating the change of the characteristic value according to the time axis;
- a translation calculating unit that performs frequency translation on time series data created by the data collecting unit so as to calculate frequency data;
- an extracting unit that extracts a power spectrum of a frequency according to the number of production processing devices and the number of measuring devices in the operation state on the basis of frequency data calculated by the translation calculating unit;
- a setting unit that sets at least one production processing device and at least one measuring device in the operation state from among the m production processing devices and the n measuring devices; and
- a number-of-devices control unit that controls the setting unit on the basis of time series data created by the data collecting unit,
- wherein the specifying unit specifies the production processing device or the measuring device as a device to be adjusted on the basis of the power spectrum of the frequency according to the number of production processing devices and the number of measuring devices in the operation state, which are extracted by the extracting unit.

12. The adjusting apparatus according to claim 11,
- wherein the number-of-devices control unit sequentially stops the operation of any one of the production processing devices or the measuring device specified as the device to be adjusted until the integral value of the power spectrum of the frequency corresponding to the production processing device or the measuring device specified by the specifying unit as the device to be adjusted is equal to or less than a predetermined value.

13. The adjusting apparatus according to claim 7,
- wherein the number-of-devices control unit calculates a standard deviation of the characteristic values on the basis of time series data created by the data collecting unit and sequentially stops the operation of any one of the production processing devices or the measuring devices specified by the specifying unit as the device to be adjusted until the calculated standard deviation is equal to or less then a predetermined value.

14. The adjusting apparatus according to claim 7, further comprising:
- a masking unit that divides a mask component which is a power spectrum of a frequency according to a or b or a power spectrum of a frequency of an integer multiple of the frequency according to a or b from frequency data, and a non-mask component which is a power spectrum excluding the power spectrum of the mask component, from frequency data; and
- a inverse-translating unit that performs frequency inverse-translation on any one of the mask component and the non-mask component divided by the masking unit so as to calculate the value of time series data,
- wherein the number-of-devices control unit sequentially stops the operation of any one of the production processing devices or the measuring devices specified by the specifying unit as the device to be adjusted until the value of time series data obtained by performing frequency inverse-translation on the mask component by the inverse-translating unit is equal to or less than a predetermined value.

15. The adjusting apparatus according to claim 14, further comprising:
- a first data output unit that outputs a value obtained by the inverse-translating unit on the basis of the non-mask component,
- wherein the value outputted from the first data output unit is the number of values out of a regular range of characteristic values, in which the produced articles meet regular quality, from among the values of time series data obtained on the basis of the non-mask component, or a standard deviation of the values of time series data obtained on the basis of the non-mask component.

16. A production processing system comprising:
- the adjusting apparatus according to claim 1; further comprising
- m production processing devices, each of which produces the article; and
- n measuring devices, each of which measures characteristic values indicating quality of the articles produced by one of the production processing devices.

17. A production processing system comprising:
- the adjusting apparatus according to claim 7; further comprising
- m production processing devices each of which produces articles; and
- n measuring devices each of which measures characteristic values indicating quality of the articles produced by the production processing devices.

18. A production processing system comprising:
- the adjusting apparatus according to claim 11; further comprising
- m production processing devices each of which produces the articles; and
- n measuring devices each of which measures characteristic values indicating quality of the articles produced by the production processing devices.

19. A method of controlling an adjusting apparatus, which receives characteristic values indicating quality of articles produced by one of m production processing devices from one of n measuring devices, and specifies a device to be adjusted, where m and n are natural numbers different from each other, the method comprising:
- a step of, on the basis of the characteristic values received from the measuring device, judging whether or not the produced articles meet regular quality; and
- a step of, if it is judged in the judging step that the produced article does not meet regular quality, specifying the device to be adjusted according to whether an abnormal characteristic value, which is a characteristic value out of a range of characteristic values when the produced articles meet regular quality, appears by m cycles or n cycles.

20. The method of controlling an adjusting apparatus according to claim 19, further comprising:
- a step of when a transfer sequence number of the articles corresponding to the characteristic values is considered as a time axis, creating time series data indicating the change of the characteristic values according to the time axis;

a step of performing frequency translation on created time series data so as to calculate frequency data;

a step of setting at least one production processing device and at least one measuring device in the operation state from among the production processing devices and measuring devices; and a step of, when the number of production processing devices in the operation state and the number of measuring devices in the operation state are a and b, respectively, where one of a and b is multiples the other, controlling so as to change the number of a and/or the number of b, Wherein the specifying step specifies the production processing device or the measuring device as a device to be adjusted on the basis of calculated frequency data.

* * * * *